US011078207B2

(12) United States Patent
Nakamura et al.

(10) Patent No.: US 11,078,207 B2
(45) Date of Patent: Aug. 3, 2021

(54) SUBSTITUTED PYRROLO[2,3-D]PYRIMIDINES AS HER2 INHIBITORS

(71) Applicant: TAIHO PHARMACEUTICAL CO., LTD., Tokyo (JP)

(72) Inventors: Masayuki Nakamura, Ibaraki (JP); Takahiro Asai, Ibaraki (JP); Satoru Iguchi, Ibaraki (JP); Kei Oguchi, Ibaraki (JP)

(73) Assignee: TAIHO PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 17/065,642

(22) Filed: Oct. 8, 2020

(65) Prior Publication Data
US 2021/0024530 A1 Jan. 28, 2021

Related U.S. Application Data

(63) Continuation of application No. PCT/JP2020/000592, filed on Jan. 10, 2020.

(30) Foreign Application Priority Data

Jan. 11, 2019 (JP) .............................. JP2019-003403

(51) Int. Cl.
*A61K 31/519* (2006.01)
*C07D 487/04* (2006.01)
*A61P 35/04* (2006.01)
*A61K 9/00* (2006.01)

(52) U.S. Cl.
CPC ............ *C07D 487/04* (2013.01); *A61P 35/04* (2018.01); *A61K 9/0053* (2013.01)

(58) Field of Classification Search
CPC ............................ A61K 31/519; C07D 487/04
USPC ........................................ 514/265.1; 544/280
See application file for complete search history.

(56) References Cited

U.S. PATENT DOCUMENTS

| 2010/0144705 A1 | 6/2010 | Miller |
| 2017/0217970 A1 | 8/2017 | Kawai et al. |
| 2018/0009818 A1 | 1/2018 | Miyazaki et al. |
| 2019/0119284 A1 | 4/2019 | Novotny et al. |

FOREIGN PATENT DOCUMENTS

| WO | WO 2010/065898 A2 | 6/2010 |
| WO | WO 2017/038838 A1 | 3/2017 |
| WO | WO 2017/146116 A1 | 8/2017 |
| WO | WO 2017/184775 A1 | 10/2017 |

OTHER PUBLICATIONS

Witzel et al., "Breast cancer brain metastases: biology and new clinical perspectives", Breast Cancer Research 18:8, pp. 1-9, (2016).
Yan et al., "HER2 aberrations in cancer: Implications for therapy", Cancer Treatment Reviews, 40, pp. 770-780, (2014).
Abdallah et al., "Brain metastases in non-small-cell lung cancer: are tyrosine kinase inhibitors and checkpoint inhibitors now viable options?", Current Oncology, vol. 25, pp. S103-S114, (2018).
Lin et al., "Phase II Trial of Lapatinib for Brain Metastases in Patients With Human Epidermal Growth Factor Receptor 2-Positive Breast Cancer", Journal of Clinical Oncology, vol. 26, pp. 1993-1999, 2008.
Kennecke et al., "Metastatic Behavior of Breast Cancer Subtypes", Journal of Clinical Oncology, vol. 28, pp. 3271-3277, 2010.
Burstein et al., "Neratinib, an Irreversible ErbB Receptor Tyrosine Kinase Inhibitor, in Patients With Advanced ErbB2-Positive Breast Cancer", Journal of Clinical Oncology, vol. 28, pp. 1301-1307, 2010.

(Continued)

*Primary Examiner* — Douglas M Willis
(74) *Attorney, Agent, or Firm* — Oblon, McClelland, Maier & Neustadt, L.L.P.

(57) ABSTRACT

Provided are a novel pyrimidine compound that inhibits HER2 activity and exhibits brain penetration properties, or a salt thereof, and a pharmaceutical composition comprising the same.

A compound represented by the following formula (I), or a salt thereof:

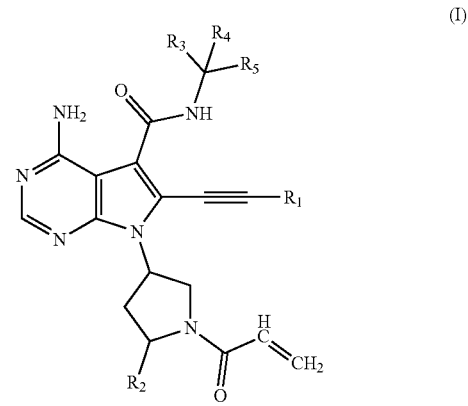

(I)

wherein $R_1$ represents a C1-C4 alkyl group optionally having a C1-C4 alkoxy group as a substituent, or a C3-C4 cycloalkyl group;
$R_2$ represents a hydrogen atom, a halogen atom, a C1-C6 alkyl group optionally having 1 to 5 C1-C4 alkoxy groups or fluorine atoms each as a substituent(s), or a C1-C6 alkoxy group;
$R_3$ represents a hydrogen atom, or a C1-C4 alkyl group optionally having 1 to 5 fluorine atoms as a substituent(s);
$R_4$ represents a hydrogen atom or a C1-C4 alkyl group; and
$R_5$ represents a phenyl group optionally having 1 to 3 substituents selected from fluorine atoms and chlorine atoms.

19 Claims, 3 Drawing Sheets

Specification includes a Sequence Listing.

(56) References Cited

OTHER PUBLICATIONS

Freedman et al., "Translational Breast Cancer Research Consortium (TBCRC) 022: A Phase II Trial of Neratinib for Patients With Human Epidermal Growth Factor Receptor 2-Positive Breast Cancer and Brain Metastases", Journal of Clinical Oncology, vol. 34, pp. 945-952 (2016).

Gomez et al., "Efficacy and Safety of Lapatinib as First-Line Therapy for ErbB2-Amplified Locally Advanced or Metastatic Breast Cancer", Journal of Clinical Oncology, vol. 26, pp. 2999-3005, 2008.

Timothy P. Heffron, "Small Molecule Kinase Inhibitors for the Treatment of Brain Cancer", Journal of Medicinal Chemistry, 59, pp. 10030-10066, (2016).

Perera et al., "HER2$^{YVMA}$ drives rapid development of adenosquamous lung tumors in mice that are sensitive to BIBW2992 and rapamycin combination therapy", Proc Natl Acad Sci USA., vol. 106, pp. 474-479, (2009).

[Figure 1]
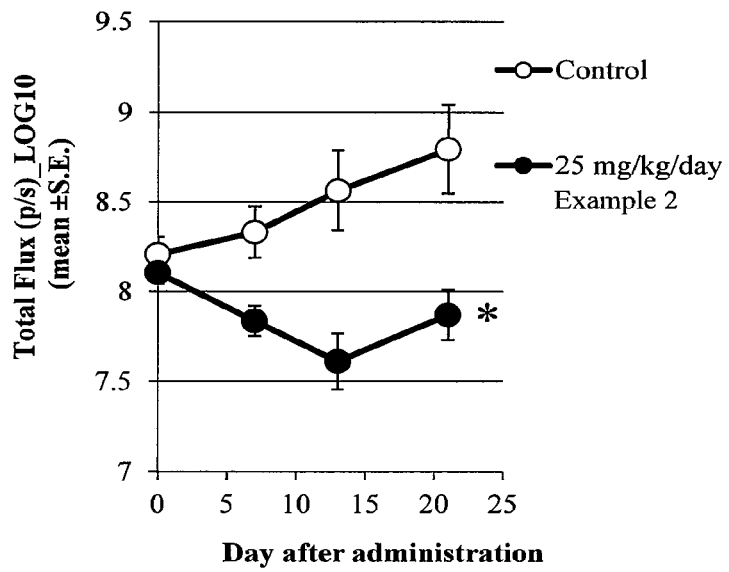
∗ : P=0.0077
[Figure 2]
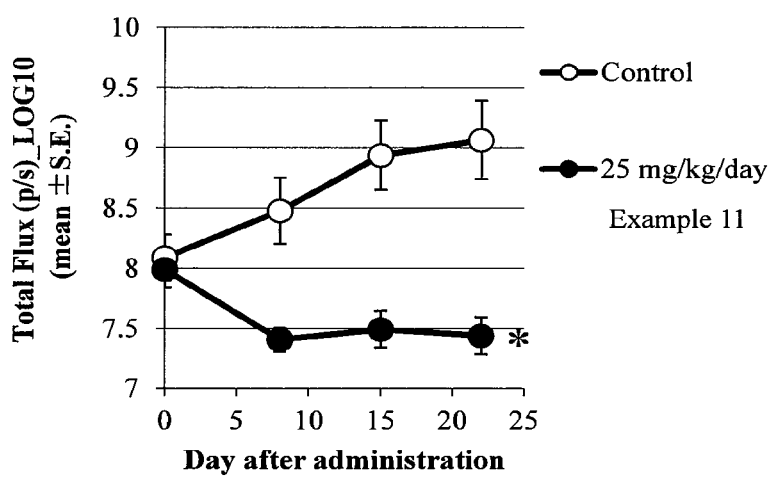
∗ : P=0.0007

[Figure 3]
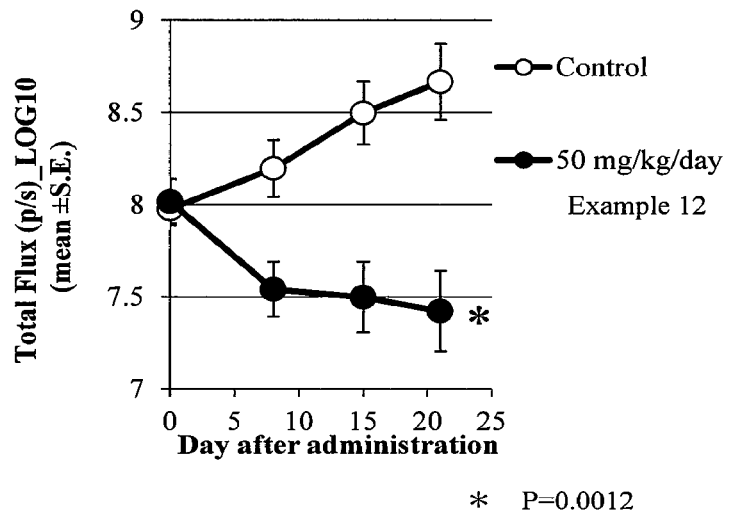
* P=0.0012
[Figure 4]
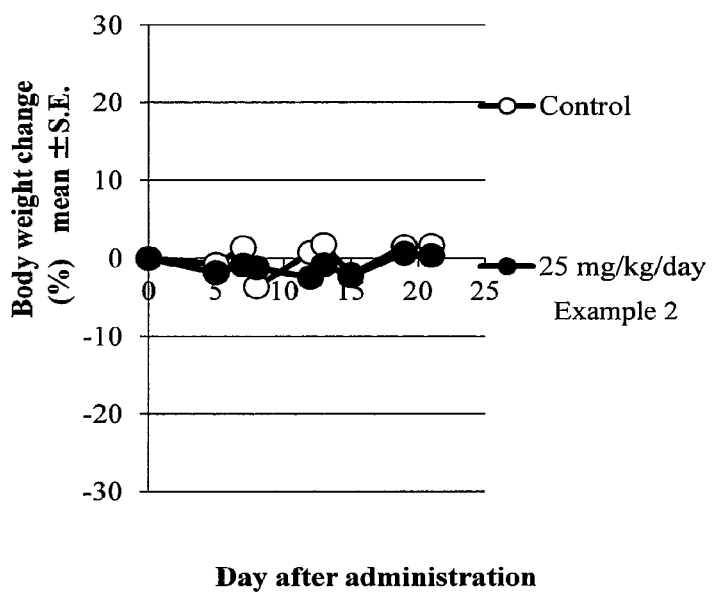
Day after administration

[Figure 5]
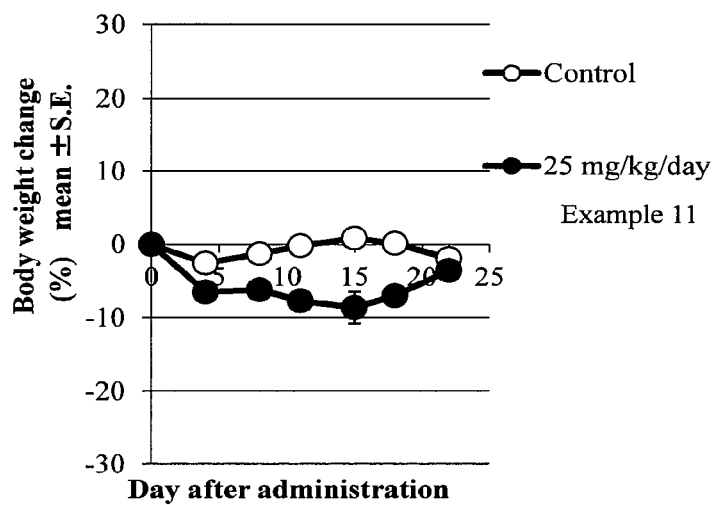
[Figure 6]
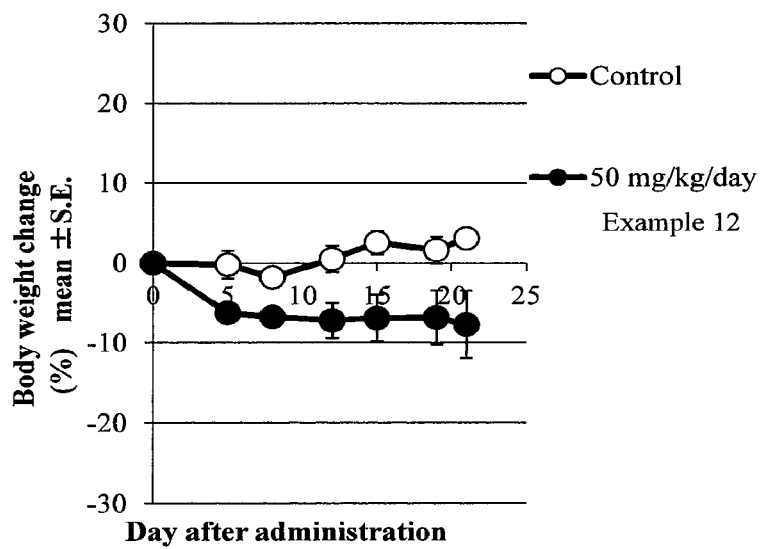

SUBSTITUTED PYRROLO[2,3-D]PYRIMIDINES AS HER2 INHIBITORS

CROSS-REFERENCE TO RELATED APPLICATIONS

The present application is a continuation of International Application No. PCT/JP2020/000592, filed Jan. 10, 2020, which is based upon and claims the benefits of priority to Japanese Application No. 2019-003403, filed Jan. 11, 2019. The entire contents of all of the above applications are incorporated herein by reference.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

Field of the Invention

The present invention relates to a novel pyrimidine compound having HER2 inhibitory activity, or a salt thereof, and a pharmaceutical composition comprising the same as an active ingredient.

Description of Related Art

HER2 (which is also referred to as "ErbB2") is receptor tyrosine kinase belonging to the ErbB family.

HER2 is considered to be a proto-oncogene. It has been reported that HER2 gene amplification, overexpression, mutation and the like occur in various types of cancers. From non-clinical and clinical research data, it is considered that activation of HER2 and downstream signals plays an important role in the survival and/or proliferation, etc. of cancer cells associated with the genetic abnormality, overexpression and the like of HER2 (Non Patent Literature 1).

Accordingly, an inhibitor capable of regulating the kinase activity of HER2 is assumed to inhibit HER2 and downstream signals in cancer cells having HER2 gene amplification, overexpression or mutation, so as to exhibit antitumor effects on the cancer cells. Therefore, such an inhibitor is considered to be useful for the treatment, life-prolonging, or QOL improvement of cancer patients.

It has been reported that brain metastasis occurs in approximately 25% to 40% of lung cancer cases, in approximately 15% to 30% of breast cancer cases, and in certain percentages of other multiple cancer cases (Non Patent Literatures 2 and 3). As a matter of fact, it has been reported that brain metastasis occurs in approximately 20% to 30% of HER2-positive breast cancer cases (Non Patent Literature 4).

Compounds having HER2 inhibitory activity, such as Lapatinib and Neratinib, have been approved as therapeutic agents against HER2-positive breast cancer. However, it has been reported that since all of these therapeutic agents are substrates of p-gp or Bcrp, the brain penetration properties of these agents are limited in non-clinical tests (Non Patent Literature 5). In fact, in clinical tests using Lapatinib or Neratinib, sufficient effects of these agents could not be obtained against brain metastatic cancer (Non Patent Literatures 6, 7, 8, and 9).

From the viewpoint of the control of pathological conditions including brain metastasis nidus, it has been desired to develop a HER2 inhibitor having inhibitory activity against HER2 and also having brain penetration properties.

One of HER2 mutations, HER2ex20ins mutation has been reported to be an activating mutation in lung cancer, etc. (Non Patent Literature 10), and regarding such HER2ex20ins mutation, multiple clinical trials have been carried out. However, under the current circumstances, a therapeutic method therefor has not yet been established. Therefore, it has been desired to develop a HER2 inhibitor having inhibitory activity against HER2ex20ins mutation.

CITATION LIST

Patent Literature

Patent Literature 1: International Publication No. WO 2017/146116
Patent Literature 2: International Publication No. WO 2017/038838

Non Patent Literature

Non Patent Literature 1: Cancer Treatment Reviews, 40, pp. 770-780 (2014)
Non Patent Literature 2: Current Oncology, 25, pp. S103-S114 (2018)
Non Patent Literature 3: Breast Cancer Research, 18(1), 8, pp. 1-9 (2016)
Non Patent Literature 4: Journal of Clinical Oncology, 28, pp. 3271-3277 (2010)
Non Patent Literature 5: Journal of Medicinal Chemistry, 59, pp. 10030-10066 (2016)
Non Patent Literature 6: Journal of Medicinal Chemistry, 26, pp. 2999-3005 (2008)
Non Patent Literature 7: Journal of Clinical Oncology, 26, pp. 1993-1999 (2008)
Non Patent Literature 8: Journal of Clinical Oncology, 28, pp. 1301-1307 (2010)
Non Patent Literature 9: Journal of Clinical Oncology, 34, pp. 945-952 (2016)
Non Patent Literature 10: Proc Natl Acad Sci USA., 106, pp. 474-479 (2009)

BRIEF SUMMARY OF THE INVENTION

It is an object of the present invention to provide a novel pyrimidine compound that inhibits HER2 activity and exhibits brain penetration properties, or a salt thereof, and a pharmaceutical composition comprising the same.

As a result of intensive studies, the present inventors have found a novel compound represented by the following formula (I) having pyrimidine as a basic skeleton. This is a novel compound characterized in that it has a structure, in which pyrrolo[2,3-d]pyrimidine is a basic skeleton, the position 5 thereof is substituted with carboxamide, the position 6 thereof is substituted with alkyne, and further a pyrrolidine group substituted with acrylamide is present at the position 7 thereof.

Specifically, one embodiment of the present invention provides the following [1] to [25]:

[1] A compound represented by the following formula (I), or a salt thereof:

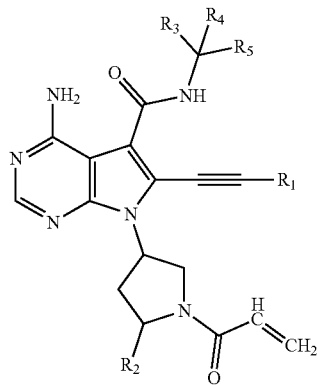
(I)

wherein $R_1$ represents a C1-C4 alkyl group optionally having a C1-C4 alkoxy group as a substituent, or a C3-C4 cycloalkyl group;
$R_2$ represents a hydrogen atom, a halogen atom, a C1-C6 alkyl group optionally having 1 to 5 C1-C4 alkoxy groups or fluorine atoms each as a substituent(s), or a C1-C6 alkoxy group;
$R_3$ represents a hydrogen atom, or a C1-C4 alkyl group optionally having 1 to 5 fluorine atoms as a substituent(s);
$R_4$ represents a hydrogen atom or a C1-C4 alkyl group; and
$R_5$ represents a phenyl group optionally having 1 to 3 substituents selected from fluorine atoms and chlorine atoms.

[2] The compound according to the above [1] represented by the following formula (II), or salt thereof:

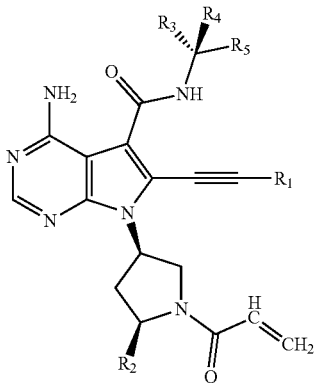
(II)

wherein $R_1$ represents a C1-C4 alkyl group optionally having a C1-C4 alkoxy group as a substituent, or a C3-C4 cycloalkyl group;
$R_2$ represents a hydrogen atom, a halogen atom, a C1-C6 alkyl group optionally having 1 to 5 C1-C4 alkoxy groups or fluorine atoms each as a substituent(s), or a C1-C6 alkoxy group;
$R_3$ represents a hydrogen atom, or a C1-C4 alkyl group optionally having 1 to 5 fluorine atoms as a substituent(s);
$R_4$ represents a hydrogen atom or a C1-C4 alkyl group; and
$R_5$ represents a phenyl group optionally having 1 to 3 substituents selected from fluorine atoms and chlorine atoms.

[3] The compound according to the above [1] or [2], or a salt thereof, wherein $R_2$ is a C1-C6 alkyl group optionally having 1 to 5 C1-C4 alkoxy groups as a substituent(s).

[4] The compound according to any one of the above [1] to [3], or a salt thereof, wherein $R_3$ is a C1-C4 alkyl group optionally having 1 to 5 fluorine atoms as a substituent(s).

[5] The compound according to any one of the above [1] to [4], or a salt thereof, wherein $R_5$ is a phenyl group optionally having 1 or 2 substituents selected from the group consisting of fluorine atoms and chlorine atoms.

[6] The compound according to any one of the above [1] to [5], or a salt thereof, wherein $R_1$ is a methyl group, a tert-butyl group, or a cyclopropyl group.

[7] The compound according to any one of the above [1] to [6], or a salt thereof, wherein $R_2$ is a methyl group, an ethyl group, a methoxymethyl group, or an ethoxymethyl group.

[8] The compound according to any one of the above [1] to [7], or a salt thereof, wherein $R_3$ is a methyl group.

[9] The compound according to any one of the above [1] to [8], or a salt thereof, wherein $R_4$ is a hydrogen atom.

[10] The compound according to any one of the above [1] to [9], or a salt thereof, wherein $R_5$ is a phenyl group.

[11] The compound according to any one of the above [1] to [10], or a salt thereof, wherein the compound is selected from the following (1) to (3):
(1) 7-((3R,5S)-1-acryloyl-5-methylpyrrolidin-3-yl)-4-amino-N—((R)-1-phenylethyl)-6-(prop-1-yn-1-yl)-7H-pyrrolo[2,3-d]pyrimidine-5-carboxamide,
(2) 7-((3R,5S)-1-acryloyl-5-methylpyrrolidin-3-yl)-4-amino-6-(cyclopropylethynyl)-N—((R)-1-phenylethyl)-7H-pyrrolo[2,3-d]pyrimidine-5-carboxamide, and
(3) 7-((3R,5S)-1-acryloyl-5-methylpyrrolidin-3-yl)-4-amino-6-(3,3-dimethylbut-1-yn-1-yl)-N—((R)-1-phenylethyl)-7H-pyrrolo[2,3-d]pyrimidine-5-carboxamide.

[12] A pharmaceutical composition comprising the compound according to any one of the above [1] to [11] or a salt thereof.

[13] An antitumor agent comprising, as an active ingredient, the compound according to any one of the above [1] to [11] or a salt thereof.

[15] An antitumor agent for oral administration, comprising, as an active ingredient, the compound according to any one of the above [1] to [11] or a salt thereof.

[15] Use of the compound according to any one of the above [1] to [11] or a salt thereof for the production of a pharmaceutical composition.

[16] Use of the compound according to any one of the above [1] to [11] or a salt thereof for the production of an antitumor agent.

[17] Use of the compound according to any one of the above [1] to [11] or a salt thereof for the production of an antitumor agent for oral administration.

[18] The compound according to any one of the above [1] to [11] or a salt thereof, for use as a medicament.

[19] The compound according to any one of the above [1] to [11] or a salt thereof, for use in the prevention and/or treatment of tumor.

[20] The compound according to any one of the above [1] to [11] or a salt thereof, for use in the prevention and/or treatment of tumor by oral administration thereof.

[21] A method for preventing and/or treating tumor, comprising administering an effective amount of the compound according to any one of the above [1] to [12] or a salt thereof to a subject in need thereof.

[22] The compound according to any one of the above [1] to [11]. or a salt thereof, for use in the prevention and/or treatment of primary brain tumor or metastatic brain tumor (e.g., brain metastasis of lung cancer, breast cancer, stomach cancer, colorectal cancer, bladder cancer, biliary tract cancer, uterine cancer, esophageal cancer, head and neck cancer, etc.).

[23] Use of the compound according to any one of the above [1] to [11] or a salt thereof for the production of a pharmaceutical composition used in the prevention and/or treatment of primary brain tumor or metastatic brain tumor (e.g., brain metastasis of lung cancer, breast cancer, stomach cancer, colorectal cancer, bladder cancer, biliary tract cancer, uterine cancer, esophageal cancer, head and neck cancer, etc.).

[24] The compound according to any one of the above [1] to [11] or a salt thereof, for use as a medicament in the prevention or treatment of primary brain tumor or metastatic brain tumor (e.g., brain metastasis of lung cancer, breast cancer, stomach cancer, colorectal cancer, bladder cancer, biliary tract cancer, uterine cancer, esophageal cancer, head and neck cancer, etc.).

[25] A method for preventing and/or treating primary brain tumor or metastatic brain tumor (e.g., brain metastasis of lung cancer, breast cancer, stomach cancer, colorectal cancer, bladder cancer, biliary tract cancer, uterine cancer, esophageal cancer, head and neck cancer, etc.), wherein the method comprises administering an effective amount of the compound according to any one of the above [1] to [11] or a salt thereof to a subject in need thereof.

The present invention has the following one or more effects.

(1) According to the present invention, provided is a novel compound represented by the above formula (I) that is useful as a HER2 inhibitor having brain penetration properties, a salt thereof, a pharmaceutical composition, an antitumor agent, or an antitumor agent for oral administration.

(2) The compound of the present invention or a salt thereof has excellent HER2 selective inhibitory activity and exhibits growth inhibitory effect against cancer cell lines.

(3) The compound of the present invention or a salt thereof can be expected to have brain penetration properties.

(4) The compound of the present invention or a salt thereof can be expected not to have serious side effects but to have medicinal effects.

(5) The compound of the present invention or a salt thereof exhibits excellent inhibitory activity against mutant HER2 (e.g., HER2 having YVMA insertion mutation in exon 20).

(6) The compound of the present invention or a salt thereof is useful as a preventive and/or therapeutic agent for tumor.

(7) The compound of the present invention or a salt thereof provides the novel compound represented by the above formula (I) that is useful for treating cancer patients, a salt thereof, a pharmaceutical composition, an antitumor agent, or an antitumor agent for oral administration.

BRIEF DESCRIPTION OF THE SEVERAL VIEWS OF THE DRAWING(S)

FIG. 1 shows the antitumor effects of the compound of Example 2 against models involving direct brain transplantation of the Luciferase gene-introduced HER2 expressing cell line (NCI-N87-luc).

FIG. 2 shows the antitumor effects of the compound of Example 11 against models involving direct brain transplantation of the Luciferase gene-introduced HER2 expressing cell line (NCI-N87-luc).

FIG. 3 shows the antitumor effects of the compound of Example 12 against models involving direct brain transplantation of the Luciferase gene-introduced HER2 expressing cell line (NCI-N87-luc).

FIG. 4 shows the body weight reduction percentage of models involving direct brain transplantation of the Luciferase gene-introduced HER2 expressing cell line (NCI-N87-luc) caused by the compound of Example 2.

FIG. 5 shows the body weight reduction percentage of models involving direct brain transplantation of the Luciferase gene-introduced HER2 expressing cell line (NCI-N87-luc) caused by the compound of Example 11.

FIG. 6 shows the body weight reduction percentage of models involving direct brain transplantation of the Luciferase gene-introduced HER2 expressing cell line (NCI-N87-luc) caused by the compound of Example 12.

DETAILED DESCRIPTION OF THE INVENTION

One embodiment of the present invention relates to a compound represented by the following formula (I), or a salt thereof:

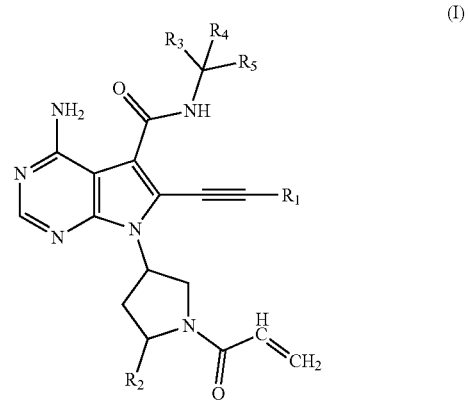

(I)

One preferred embodiment of the present invention relates to a compound represented by the following formula (II), or a salt thereof:

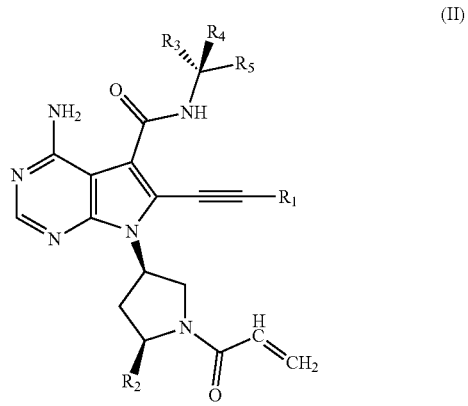

(II)

The compound represented by the above formula (I) or formula (II) of the present invention is a compound having pyrrolo[2,3-d]pyrimidine as a basic structure, and this is a novel compound described in none of the aforementioned prior art publications, etc.

In the present description, specific examples of the "halogen atom" may include a chlorine atom, a bromine atom, a fluorine atom, and an iodine atom. Among these, a chlorine atom and a fluorine atom are preferable, and a fluorine atom is more preferable.

In the present description, the "alkyl group" means a linear or branched saturated hydrocarbon group. Specific examples of the alkyl group may include a methyl group, an ethyl group, an n-propyl group, an isopropyl group, an n-butyl group, an isobutyl group, a sec-butyl group, a tert-butyl group, a pentyl group, and a hexyl group. Among these, a linear or branched alkyl group containing 1 to 4 carbon atoms is preferable, and a methyl group and a tert-butyl group are more preferable.

In the present description, the "haloalkyl group" means a linear or branched saturated hydrocarbon group, in which one to all hydrogen atoms are substituted with the above-described halogen atoms. Specific examples of the haloalkyl group may include a monofluoromethyl group, a difluoromethyl group, a trifluoromethyl group, a 1-fluoroethyl group, a 2-fluoroethyl group, a 1,1-difluoroethyl group, a 1,2-difluoroethyl group, a 2,2-difluoroethyl group, a 2,2,2-trifluoroethyl group, a monochoromethyl group, a dichloromethyl group, a trichloromethyl group, a 1-chloroethyl group, a 2-chloroethyl group, and a 1,1-dichloroethyl group. Among these, a linear or branched saturated hydrocarbon group containing 1 to 6 carbon atoms, in which 1 to 3 hydrogen atoms are substituted with the above-described halogen atoms, is preferable, and a monofluoromethyl group is more preferable.

In the present description, the "cycloalkyl group" means a monocyclic or polycyclic saturated hydrocarbon group containing 3 to 7 carbon atoms. Specific examples of the cycloalkyl group may include a cyclopropyl group, a cyclobutyl group, a cyclopentyl group, a cyclohexyl group, and a cycloheptyl group. Among these, a cyclopropyl group and a cyclobutyl group are preferable.

In the present description, the "aromatic hydrocarbon group" means a cyclic substituent consisting of carbon and hydrogen, having an unsaturated bond, in which 4e+2 (wherein e represents an integer of 1 or greater) electrons are contained in the cyclic π electron system.

In the present description, the "C6-C14 aromatic hydrocarbon group" means a monocyclic or polycyclic aromatic hydrocarbon group containing 6 to 14 carbon atoms. Specific examples of the C6-C14 aromatic hydrocarbon group may include a phenyl group, a naphthyl group, a tetrahydronaphthyl group, and an anthracenyl group. Among these, a phenyl group is preferable.

In the present description, the "aralkyl group" means the above-described alkyl group substituted with the above-described aromatic hydrocarbon group. Specific examples of the aralkyl group may include C7-C16 aralkyl groups such as a benzyl group, a phenylethyl group, a phenylpropyl group, a naphthylmethyl group, and a naphthylethyl group. Among these, a benzyl group is preferable.

In the present description, the "unsaturated hydrocarbon group" means a linear or branched hydrocarbon group containing 2 to 6 carbon atoms, which comprises at least one carbon-carbon double bond or triple bond. Specific examples of the unsaturated hydrocarbon group may include a vinyl group, an allyl group, a methylvinyl group, a propenyl group, a butenyl group, a pentenyl group, a hexenyl group, an ethynyl group, and a 2-propynyl group. Among these, a vinyl group, an allyl group, and a 1-propenyl group are preferable.

In the present description, the "alkenyl group" means a linear or branched hydrocarbon group containing 2 to 6 carbon atoms, which comprises at least one carbon-carbon double bond. Specific examples of the alkenyl group may include C2-C6 alkenyl groups, such as a vinyl group, an allyl group, a 2-methyl-2-propenyl group, an isopropenyl group, a 1-, 2- or 3-butenyl group, a 2-, 3- or 4-pentenyl group, a 2-methyl-2-butenyl group, a 3-methyl-2-butenyl group, and a 5-hexenyl group. Among these, a vinyl group, an allyl group, a 1-propenyl group, and a 2-methyl-2-propenyl group are preferable.

In the present description, the "alkynyl group" means a linear or branched unsaturated hydrocarbon group having at least one triple bond (for example, 1 or 2, and preferably 1 triple bond). Specific examples of the alkynyl group may include C2-C6 alkynyl groups such as an ethynyl group, a 1- or 2-propynyl group, a 1-, 2- or 3-butynyl group, and a 1-methyl-2-propynyl group. Among these, an ethynyl group and a 2-propynyl group are preferable.

In the present description, the "C3-C10 cyclic unsaturated hydrocarbon group" means a monocyclic or polycyclic hydrocarbon group containing 3 to 10 carbon atoms, which comprises at least one carbon-carbon double bond. Specific examples of the C3-C10 cyclic unsaturated hydrocarbon group may include a cyclopropenyl group, a cyclobutenyl group, a cyclopentenyl group, a cyclohexenyl group, a cycloheptenyl group, a cyclooctenyl group, and a cyclononyl group. Among these, a monocyclic or polycyclic hydrocarbon group containing 3 to 7 carbon atoms, which comprises at least one carbon-carbon double bond, is preferable, and a cyclopropenyl group is more preferable.

In the present description, the "alkoxy group" means an oxy group having the above-described alkyl group. Specific examples of the alkoxy group may include C1-C6 alkoxy groups such as a methoxy group, an ethoxy group, an n-propoxy group, an isopropoxy group, an n-butoxy group, an isobutoxy group, a sec-butoxy group, a tert-butoxy group, a pentyloxy group, an isopentyloxy group, and a hexyloxy group. Among these, a methoxy group and an ethoxy group are preferable, and a methoxy group is more preferable.

In the present description, the "haloalkoxy group" may include the above-described alkoxy group having at least one halogen atom (preferably 1 to 13, and more preferably 1 to 3 halogen atoms). Specific examples of the haloalkoxy group may include C1-C6 haloalkoxy groups such as a fluoromethoxy group, a difluoromethoxy group, a trifluoromethoxy group, a trichloromethoxy group, a fluoroethoxy group, a 1,1,1-trifluoroethoxy group, a monofluoro-n-propoxy group, a perfluoro-n-propoxy group, and a perfluoro-isopropoxy group.

In the present description, the "cycloalkoxy group" means an oxy group having the above-described cycloalkyl group. Specific examples of the cycloalkoxy group may include C3-C7 cycloalkoxy groups such as a cyclopropoxy group, a cyclobutoxy group, a cyclo pentyloxy group, a cyclohexyloxy group, and a cycloheptyloxy group. Among these, a cyclobutoxy group, a cyclopentyloxy group, and a cyclohexyloxy group are preferable.

In the present description, the "aralkyloxy group" means an oxy group having the above-described aralkyl group. Specific examples of the aralkyloxy group may include C7-C20 aralkyloxy groups such as a benzyloxy group, a phenethyloxy group, a naphthylmethyloxy group, and a fluorenylmethyloxy group. Among these, a benzyloxy group is preferable.

In the present description, the "alkylthio group" means a thioxy group having the above-described alkyl group. Specific examples of the alkylthio group may include C1-C6 alkylthio groups such as a methylthio group, an ethylthio group, an n-propylthio group, an isopropylthio group, an n-butylthio group, an isobutylthio group, a tert-butylthio group, an n-pentylthio group, an isopentylthio group, and a hexylthio group. Among these, a methylthio group, an ethylthio group, and an n-propylthio group are preferable.

In the present description, the "alkoxyalkyl group" means the above-described alkyl group having at least one of the above-described alkoxy groups. Specific examples of the alkoxyalkyl group may include C1-C6 alkoxy-C1-C6 alkyl groups such as a methoxymethyl group, an ethoxyethyl group, a methoxyethyl group, and a methoxypropyl group.

In the present description, the "alkylamino group" means an amino group in which 1 or 2 hydrogen atoms are substituted with a linear or branched hydrocarbon group(s) containing 1 to 6 carbon atoms. Specific examples of the alkylamino group may include a methylamino group, an ethylamino group, a dimethylamino group, a diethylamino group, and an ethylmethylamino group. Among these, preferable is an amino group in which 1 or 2 hydrogen atoms are substituted with a linear or branched hydrocarbon group containing 1 to 3 carbon atoms.

In the present description, the "monoalkylamino group" means an amino group in which one hydrogen atom is substituted with a linear or branched hydrocarbon group. Specific examples of the monoalkylamino group may include a methylamino group, an ethylamino group, an n-propylamino group, an isopropylamino group, an n-butylamino group, an isobutylamino group, a sec-butylamino group, a tert-butylamino group, a pentylamino group, and a hexylamino group. Among these, preferable is an amino group in which one hydrogen atom is substituted with a linear or branched hydrocarbon group containing 1 to 3 carbon atoms.

In the present description, the "dialkylamino group" means an amino group in which two hydrogen atoms are substituted with linear or branched hydrocarbon groups containing 1 to 6 carbon atoms. Specific examples of the dialkylamino group may include a dimethylamino group, a diethylamino group, and an ethylmethylamino group. Among these, an amino group in which two hydrogen atoms are substituted with linear or branched hydrocarbon groups containing 1 to 3 carbon atoms is preferable, and a dimethylamino group is more preferable.

In the present description, the "acyl group" means a formyl group in which a hydrogen atom is substituted with a linear or branched hydrocarbon group. Specific examples of the acyl group may include an acetyl group, an n-propanoyl group, an isopropanoyl group, an n-butyloyl group, and a tert-butyloyl group. Among these, a formyl group in which a hydrogen atom is substituted with a linear or branched hydrocarbon group containing 1 to 3 carbon atoms is preferable, and an acetyl group is more preferable.

In the present description, the "acyloxy group" means an oxy group having the above-described acyl group. Specific examples of the acyloxy group may include an alkylcarbonyloxy group and an arylcarbonyloxy group. Among these, an oxy group in which a hydrogen atom of formyl group is substituted with a linear or branched hydrocarbon group containing 1 to 3 carbon atoms is preferable, and an alkylcarbonyloxy group is more preferable.

In the present description, the "alkoxycarbonyl group" means a carbonyl group having the above-described alkoxy group. Specific examples of the alkoxycarbonyl group may include (C1-C6alkoxy)carbonyl groups such as a methoxycarbonyl group, an ethoxycarbonyl group, a propoxycarbonyl group, an isopropoxycarbonyl group, a butoxycarbonyl group, an isobutoxycarbonyl group, a tert-butoxycarbonyl group, a pentyloxycarbonyl group, an isopentyloxycarbonyl group, and a hexyloxycarbonyl group. Among these, a tert-butoxycarbonyl group is preferable.

In the present description, the "aralkyloxycarbonyl group" means a carbonyl group having the above-described aralkyloxy. Specific examples of the aralkyloxycarbonyl group may include (C6-C20 aralkyl)oxycarbonyl groups such as a benzyloxycarbonyl group, a phenethyloxycarbonyl group, a naphthylmethyloxycarbonyl group, and a fluorenylmethyloxycarbonyl group. Among these, a benzyloxycarbonyl group is preferable.

In the present description, the "saturated heterocyclic group" means a monocyclic or polycyclic saturated heterocyclic group having at least one heteroatom (preferably 1 to 5, and more preferably 1 to 3 heteroatoms) selected from nitrogen atoms, oxygen atoms, and sulfur atoms. Specific examples of the saturated heterocyclic group may include an aziridinyl group, an azetidinyl group, an imidazolidinyl group, a morpholino group, a pyrrolidinyl group, a piperidinyl group, a piperazinyl group, a tetrahydrofuranyl group, a tetrahydropyranyl group, a tetrahydrothiophenyl group, a thiazolidinyl group, and an oxazolidinyl group. Among these, an azetidinyl group, a pyrrolidinyl group, and a piperidinyl group are preferable, and an azetidinyl group and a pyrrolidinyl group are more preferable.

In the present description, the "unsaturated heterocyclic group" means a monocyclic or polycyclic completely unsaturated or partially unsaturated heterocyclic group having at least one heteroatom (preferably 1 to 5, and more preferably 1 to 3 heteroatoms) selected from nitrogen atoms, oxygen atoms, and sulfur atoms. Specific examples of the unsaturated heterocyclic group may include an imidazolyl group, a thienyl group, a pyrrolyl group, an oxazolyl group, an isoxazolyl group, a thiazolyl group, an isothiazolyl group, a thiadiazolyl group, an oxadiazolyl group, a pyrazolyl group, a triazolyl group, a tetrazolyl group, a pyridyl group, a pyrazyl group, a pyrimidinyl group, a pyridazinyl group, an indolyl group, an isoindolyl group, an indazolyl group, a triazolopyridyl group, a benzimidazolyl group, a benzoxazolyl group, a benzothiazolyl group, a benzothienyl group, a furanyl group, a benzofuranyl group, a purinyl group, a quinolyl group, an isoquinolyl group, a quinazolinyl group, a quinoxalyl group, a methylenedioxyphenyl group, an ethylenedioxyphenyl group, and a dihydrobenzofuranyl group. Among these, an imidazolyl group, a pyrazolyl group, a thiazolyl group, an isoxazolyl group, and a furanyl group are preferable; an imidazolyl group, a pyrazolyl group, and a thiazolyl group are more preferable; and an imidazolyl group is most preferable.

In the present description, the "saturated heterocyclic oxy group" means an oxy group having the above-described saturated heterocyclic group. Specific examples of the saturated heterocyclic oxy group may include a morpholinyloxy group, a 1-pyrrolidinyloxy group, a piperidinooxy group, a piperazinyloxy group, a 4-methyl-1-piperazinyloxy group, a tetrahydrofuranyloxy group, a tetrahydropyranyloxy group, a tetrahydrothiophenyloxy group, a thiazolidinyloxy group, and an oxazolidinyloxy group. Among these, a 1-pyrrolidinyloxy group, a piperidinooxy group, and a piperazinyloxy group are preferable.

In the compound represented by the formula (I) or the formula (II) of the present invention, $R_1$ is a C1-C4 alkyl group optionally having a C1-C4 alkoxy group as a substituent, or a C3-C4 cycloalkyl group.

The "C1-C4 alkoxy group" in the "C1-C4 alkyl group optionally having a C1-C4 alkoxy group as a substituent" represented by $R_1$ is preferably a methoxy group or an ethoxy group, and most preferably a methoxy group. Herein, the number of substituents is preferably 1 to 3, and most preferably 1. When the C1-C4 alkyl group has two or more substituents, the substituents may be identical to or different from each other.

The "C1-C4 alkyl group" in the "C1-C4 alkyl group optionally having a C1-C4 alkoxy group as a substituent" represented by $R_1$ is preferably a methyl group, an ethyl group, an n-propyl group, an isopropyl group, or a tert-butyl group, more preferably a methyl group, an ethyl group, an isopropyl group, or a tert-butyl group, and most preferably a methyl group or a tert-butyl group.

The "C1-C4 alkyl group optionally having a C1-C4 alkoxy group as a substituent" represented by $R_1$ is preferably a C1-C4 alkyl group having 1 to 3 methoxy groups as substituents, more preferably a methyl group, an ethyl group, an isopropyl group, a tert-butyl group, or a 1-methyl-1-methoxyethyl group, and most preferably a methyl group or a tert-butyl group.

The "C3-C4 cycloalkyl group" represented by $R_1$ is preferably a cyclopropyl group or a cyclobutyl group, and most preferably a cyclopropyl group.

$R_1$ is preferably a C1-C4 alkyl group optionally having 1 to 3 C1-C4 alkoxy groups as substituents, or a C3-C4 cycloalkyl group.

$R_1$ is more preferably a C1-C4 alkyl group optionally having 1 to 3 methoxy groups as substituents, or a C3-C4 cycloalkyl group.

$R_1$ is further preferably a methyl group, an ethyl group, an isopropyl group, a tert-butyl group, a 1-methyl-1-methoxyethyl group, or a cyclopropyl group.

$R_1$ is most preferably a methyl group, a tert-butyl group, or a cyclopropyl group.

In the compound represented by the formula (I) or the formula (II) of the present invention, $R_2$ is a hydrogen atom, a halogen atom, a C1-C6 alkyl group optionally having 1 to 5 C1-C4 alkoxy groups or fluorine atoms each as a substituent(s), or a C1-C6 alkoxy group.

The "halogen atom" represented by $R_2$ is preferably a fluorine atom or a chlorine atom.

The "C1-C4 alkoxy group" in the "C1-C6 alkyl group optionally having 1 to 5 C1-C4 alkoxy groups or fluorine atoms each as a substituent(s)" represented by $R_2$ is preferably a methoxy group or an ethoxy group, and most preferably a methoxy group.

The "C1-C6 alkyl group optionally having 1 to 5 C1-C4 alkoxy groups or fluorine atoms each as a substituent(s)" represented by $R_2$ is preferably a methyl group, an ethyl group, an n-propyl group, an isopropyl group, or a tert-butyl group, and most preferably a methyl group.

The "C1-C6 alkyl group" in the "C1-C6 alkyl group optionally having 1 to 5 C1-C4 alkoxy groups or fluorine atoms each as a substituent(s)" represented by $R_2$ is preferably a C1-C6 alkyl group optionally having 1 to 5 methoxy groups, ethoxy groups, or fluorine atoms as a substituent(s) (specifically, a methyl group, a methoxymethyl group, an ethoxymethyl group, a methoxyethyl group, an ethoxyethyl group, a fluoromethyl group, a difluoromethyl group, a trifluoromethyl group, etc.), more preferably a C1-C6 alkyl group, further preferably a methyl group, an ethyl group, an n-propyl group, an isopropyl group, or a tert-butyl group, and most preferably a methyl group.

The "C1-C6 alkoxy group" represented by $R_2$ is preferably a methoxy group or an ethoxy group, and most preferably a methoxy group.

$R_2$ is preferably a C1-C6 alkyl group optionally having 1 to 5 C1-C4 alkoxy groups or fluorine atoms each as a substituent(s). In one embodiment, $R_2$ is a C1-C6 alkyl group optionally having 1 to 5 methoxy groups, ethoxy groups, or fluorine atoms as a substituent(s). In another embodiment, $R_2$ is a methyl group, an ethyl group, an n-propyl group, an isopropyl group, or a tert-butyl group (preferably a methyl group or an ethyl group, and more preferably a methyl group), each optionally having 1 to 5 methoxy groups, ethoxy groups, or fluorine atoms as a substituent(s).

$R_2$ is more preferably a C1-C6 alkyl group optionally having 1 to 5 C1-C4 alkoxy groups as a substituent(s). In one embodiment, $R_2$ is a C1-C6 alkyl group optionally having 1 to 5 methoxy groups or ethoxy groups as a substituent(s). In another embodiment, $R_2$ is a methyl group, an ethyl group, an n-propyl group, an isopropyl group, or a tert-butyl group (preferably a methyl group or an ethyl group, and more preferably a methyl group) each optionally having 1 to 5 methoxy groups or ethoxy groups as a substituent(s). In a further embodiment, $R_2$ is a methyl group, an ethyl group, a methoxymethyl group, or an ethoxymethyl group.

$R_2$ is even more preferably a C1-C6 alkyl group.

$R_2$ is further preferably a methyl group, an ethyl group, an n-propyl group, an isopropyl group, or a tert-butyl group.

$R_2$ is particularly preferably a methyl group or an ethyl group.

$R_2$ is most preferably a methyl group.

In the compound represented by the formula (I) or the formula (II) of the present invention, $R_3$ is a hydrogen atom, or a C1-C4 alkyl group optionally having 1 to 5 fluorine atoms as a substituent(s).

The "C1-C4 alkyl group" in the "C1-C4 alkyl group optionally having 1 to 5 fluorine atoms as a substituent(s)" represented by $R_3$ is preferably a methyl group, an ethyl group, an n-propyl group, an isopropyl group, or a tert-butyl group, more preferably a methyl group or an ethyl group, and most preferably a methyl group.

The "C1-C4 alkyl group optionally having 1 to 5 fluorine atoms as a substituent(s)" represented by $R_3$ is preferably a methyl group, a fluoromethyl group, a difluoromethyl group, a trifluoromethyl group, or an ethyl group, more preferably a methyl group, a trifluoromethyl group, or an ethyl group, and most preferably a methyl group.

$R_3$ is preferably a C1-C4 alkyl group optionally having 1 to 5 fluorine atoms as a substituent(s).

$R_3$ is more preferably a methyl group, a fluoromethyl group, a difluoromethyl group, a trifluoromethyl group, an ethyl group, a fluoroethyl group, a difluoroethyl group, a trifluoroethyl group, an n-propyl group, an isopropyl group, or a tert-butyl group.

$R_3$ is even more preferably a methyl group, a fluoromethyl group, a difluoromethyl group, a trifluoromethyl group, or an ethyl group.

$R_3$ is further preferably a methyl group, a trifluoromethyl group, or an ethyl group.

$R_3$ is particularly preferably a methyl group or an ethyl group.

$R_3$ is most preferably a methyl group.

In the compound represented by the formula (I) or the formula (II) of the present invention, $R_4$ is a hydrogen atom or a C1-C4 alkyl group.

The "C1-C4 alkyl group" represented by $R_4$ is preferably a methyl group, an ethyl group, an n-propyl group, an isopropyl group, or a tert-butyl group, more preferably a methyl group or an ethyl group, and most preferably a methyl group.

$R_4$ is preferably a hydrogen atom, a methyl group, an ethyl group, an n-propyl group, an isopropyl group, or a tert-butyl group.

$R_4$ is more preferably a hydrogen atom, a methyl group, or an ethyl group.

$R_4$ is further preferably a hydrogen atom or a methyl group.

$R_4$ is most preferably a hydrogen atom.

In the compound represented by the formula (I) or the formula (II) of the present invention, $R_5$ is a phenyl group optionally having 1 to 3 substituents selected from the group consisting of fluorine atoms and chlorine atoms.

$R_5$ is preferably a phenyl group optionally having 1 or 2 substituents selected from the group consisting of fluorine atoms and chlorine atoms.

$R_5$ is more preferably a phenyl group, a 2-fluorophenyl group, a 3-chlorophenyl group, a 2,3-difluorophenyl group, a 2,4-difluorophenyl group, or a 3,5-difluorophenyl group.

$R_5$ is most preferably a phenyl group.

The compound of the present invention is preferably the compound represented by the formula (I) or the formula (II), or a salt thereof, wherein, in the formula (I) or the formula (II), $R_1$ is a C1-C4 alkyl group optionally having a C1-C4 alkoxy group as a substituent, or a C3-C4 cycloalkyl group, $R_2$ is a C1-C6 alkyl group, $R_3$ is a C1-C4 alkyl group optionally having 1 to 5 fluorine atoms as a substituent(s), $R_4$ is a hydrogen atom or a C1-C4 alkyl group, and $R_5$ is a phenyl group optionally having 1 or 2 substituents selected from the group consisting of fluorine atoms and chlorine atoms.

The compound of the present invention is more preferably the compound represented by the formula (I) or the formula (II), or a salt thereof, wherein, in the formula (I) or the formula (II), $R_1$ is a methyl group, an ethyl group, an n-propyl group, an isopropyl group, a tert-butyl group, a 1-methyl-1-methoxyethyl group, a cyclopropyl group, or a cyclobutyl group, $R_2$ is a methyl group, an ethyl group, an n-propyl group, or a tert-butyl group, $R_3$ is a methyl group, a fluoromethyl group, a difluoromethyl group, a trifluoromethyl group, an ethyl group, a fluoroethyl group, a difluoroethyl group, a trifluoroethyl group, an n-propyl group, an isopropyl group, or a tert-butyl group, $R_4$ is a hydrogen atom, a methyl group, an ethyl group, an n-propyl group, an isopropyl group, or a tert-butyl group, and $R_5$ is a phenyl group, a 2-fluorophenyl group, a 3-fluorophenyl group, a 2,4-difluorophenyl group, a 2,3-difluorophenyl group, a 3,5-difluorophenyl group, a 2-chlorophenyl group, a 3-chlorophenyl group, a 2,4-dichlorophenyl group, or a 3,5-dichlorophenyl group.

The compound of the present invention is even more preferably the compound represented by the formula (II), or a salt thereof, wherein, in the formula (II), $R_1$ is a methyl group, an ethyl group, an isopropyl group, a tert-butyl group, a 1-methyl-1-methoxyethyl group, or a cyclopropyl group, $R_2$ is a methyl group, $R_3$ is a methyl group, a fluoromethyl group, a difluoromethyl group, a trifluoromethyl group, or an ethyl group, $R_4$ is a hydrogen atom, a methyl group, or an ethyl group, and $R_5$ is a phenyl group, a 2-fluorophenyl group, a 3-chlorophenyl group, a 2,3-difluorophenyl group, a 2,4-difluorophenyl group, or a 3,5-difluorophenyl group.

The compound of the present invention is further preferably the compound represented by the formula (II), or a salt thereof, wherein, in the formula (II), $R_1$ is a methyl group, a tert-butyl group, or a cyclopropyl group, $R_2$ is a methyl group, $R_3$ is a methyl group, a trifluoromethyl group, or an ethyl group, $R_4$ is a hydrogen atom or a methyl group, and $R_5$ is a phenyl group.

The compound of the present invention is particularly preferably the compound represented by the formula (II), or a salt thereof, wherein, in the formula (II), $R_1$ is a methyl group, a tert-butyl group, or a cyclopropyl group, $R_2$ is a methyl group, $R_3$ is a methyl group, $R_4$ is a hydrogen atom, and $R_5$ is a phenyl group.

Specific examples of the compound of the present invention may include compounds produced in the following Examples, but are not limited thereto.

One embodiment of the present invention relates to a compound selected from the following (1) to (18), or a salt thereof. One embodiment of the present invention relates to a compound selected from the following (1) to (15), or a salt thereof.

(1) 7-((3R,5S)-1-acryloyl-5-methylpyrrolidin-3-yl)-4-amino-N—((R)-1-phenylethyl)-6-(prop-1-yn-1-yl)-7H-pyrrolo[2,3-d]pyrimidine-5-carboxamide, (2) 7-((3R,5S)-1-acryloyl-5-methylpyrrolidin-3-yl)-4-amino-6-(cyclopropylethynyl)-N—((R)-1-phenylethyl)-7H-pyrrolo[2,3-d]pyrimidine-5-carboxamide, (3) 7-((3R,5S)-1-acryloyl-5-methylpyrrolidin-3-yl)-4-amino-6-(3,3-dimethylbut-1-yn-1-yl)-N—((R)-1-phenylethyl)-7H-pyrrolo[2,3-d]pyrimidine-5-carboxamide, (4) 7-(R)-((3R,5S)-1-acryloyl-5-methylpyrrolidin-3-yl)-4-amino-N—((R)-1-(3,5-difluorophenyl)ethyl)-6-(prop-1-yn-1-yl)-7H-pyrrolo[2,3-d]pyrimidine-5-carboxamide, (5) 7-((3R,5S)-1-acryloyl-5-methylpyrrolidin-3-yl)-4-amino-N-(2-phenylpropan-2-yl)-6-(prop-1-yn-1-yl)-7H-pyrrolo[2,3-d]pyrimidine-5-carboxamide, (6) 7-((3R,5S)-1-acryloyl-5-methylpyrrolidin-3-yl)-4-amino-N—((R)-1-phenylpropyl)-6-(prop-1-yn-1-yl)-7H-pyrrolo[2,3-d]pyrimidine-5-carboxamide, (7) 7-((3R,5S)-1-acryloyl-5-methylpyrrolidin-3-yl)-4-amino-N-(2-(2-fluorophenyl)propan-2-yl)-6-(prop-1-yn-1-yl)-7H-pyrrolo[2,3-d]pyrimidine-5-carboxamide, (8) 7-((3R,5S)-1-acryloyl-5-methylpyrrolidin-3-yl)-4-amino-N—((R)-1-(3-chlorophenyl)ethyl)-6-(prop-1-yn-1-yl)-7H-pyrrolo[2,3-d]pyrimidine-5-carboxamide, (9) 7-((3R,5S)-1-acryloyl-5-methylpyrrolidin-3-yl)-4-amino-N—((R)-1-(2,4-difluorophenyl)ethyl)-6-(prop-1-yn-1-yl)-7H-pyrrolo[2,3-d]pyrimidine-5-carboxamide,

(10) 7-((3R,5S)-1-acryloyl-5-methylpyrrolidin-3-yl)-4-amino-6-(prop-1-yn-1-yl)-N—((S)-2,2,2-trifluoro-1-phenylethyl)-7H-pyrrolo[2,3-d]pyrimidine-5-carboxamide,

(11) 7-((3R,5S)-1-acryloyl-5-methylpyrrolidin-3-yl)-4-amino-6-(cyclopropylethynyl)-N-(2-phenylpropan-2-yl)-7H-pyrrolo[2,3-d]pyrimidine-5-carboxamide,

(12) 7-((3R,5S)-1-acryloyl-5-methylpyrrolidin-3-yl)-4-amino-6-(cyclopropylethynyl)-N—((R)-1-(2,3-difluorophenyl)ethyl)-7H-pyrrolo[2,3-d]pyrimidine-5-carboxamide,

(13) 7-((3R,5S)-1-acryloyl-5-methylpyrrolidin-3-yl)-4-amino-6-(3-methoxy-3-methylbut-1-yn-1-yl)-N—((R)-1-phenylethyl)-7H-pyrrolo[2,3-d]pyrimidine-5-carboxamide,

(14) 7-((3R,5S)-1-acryloyl-5-methylpyrrolidin-3-yl)-4-amino-6-(but-1-yn-1-yl)-N—((R)-1-phenylethyl)-7H-pyrrolo[2,3-d]pyrimidine-5-carboxamide,

(15) 7-((3R,5S)-1-acryloyl-5-methylpyrrolidin-3-yl)-4-amino-N-(2-(2-fluorophenyl)propan-2-yl)-6-(3-methylbut-1-yn-1-yl)-7H-pyrrolo[2,3-d]pyrimidine-5-carboxamide,

(16) 7-((3R,5S)-1-acryloyl-5-ethylpyrrolidin-3-yl)-4-amino-N—((R)-1-phenylethyl)-6-(prop-1-yn-1-yl)-7H-pyrrolo[2,3-d]pyrimidine-5-carboxamide,

(17) 7-((3R,5S)-1-acryloyl-5-ethylpyrrolidin-3-yl)-4-amino-6-(cyclopropylethynyl)-N—((R)-1-phenylethyl)-7H-pyrrolo[2,3-d]pyrimidine-5-carboxamide,

(18) 7-((3R,5R)-1-acryloyl-5-(methoxymethyl)pyrrolidin-3-yl)-4-amino-6-(cyclopropylethynyl)-N—((R)-1-phenylethyl)-7H-pyrrolo[2,3-d]pyrimidine-5-carboxamide, and

(19) 7-((3R,5R)-1-acryloyl-5-(ethoxymethyl)pyrrolidin-3-yl)-4-amino-6-(cyclopropylethynyl)-N—((R)-1-phenylethyl)-7H-pyrrolo[2,3-d]pyrimidine-5-carboxamide.

A preferred example of the compound of the present invention may be a compound selected from the following (1) to (3), or a salt thereof.

(1) 7-((3R,5S)-1-acryloyl-5-methylpyrrolidin-3-yl)-4-amino-N—((R)-1-phenylethyl)-6-(prop-1-yn-1-yl)-7H-pyrrolo[2,3-d]pyrimidine-5-carboxamide, (2) 7-((3R,5S)-1-acryloyl-5-methylpyrrolidin-3-yl)-4-amino-6-(cyclopropylethynyl)-N—((R)-1-phenylethyl)-7H-pyrrolo[2,3-d]pyrimidine-5-carboxamide, and (3) 7-((3R,5S)-1-acryloyl-5-methylpyrrolidin-3-yl)-4-amino-6-(3,3-dimethylbut-1-yn-1-yl)-N—((R)-1-phenylethyl)-7H-pyrrolo[2,3-d]pyrimidine-5-carboxamide.

<Method for Producing Compound Represented by Formula (I)>

The compound according to the present invention can be produced by, for example, the following production method or the methods described in the Examples. However, the method for producing the compound according to the present invention is not limited to these examples.

The compound (I) of the present invention can be produced by applying, for example, the following production method.

<Production Method>

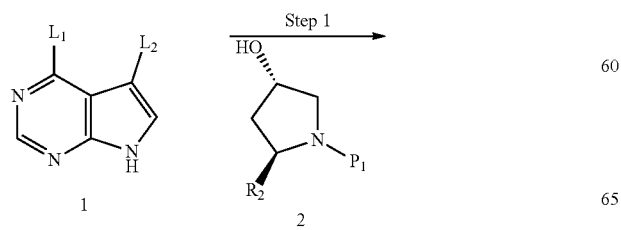

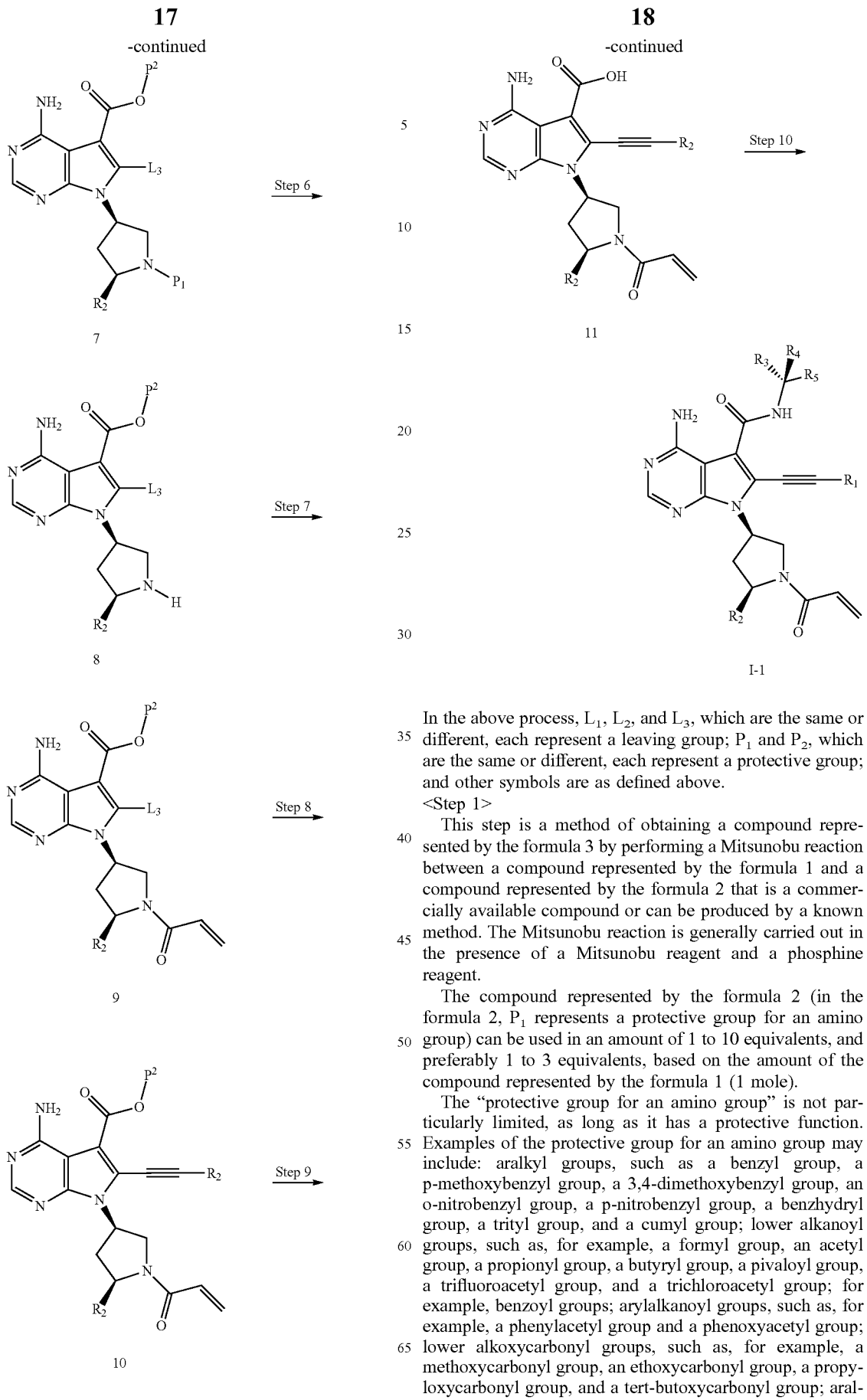

In the above process, $L_1$, $L_2$, and $L_3$, which are the same or different, each represent a leaving group; $P_1$ and $P_2$, which are the same or different, each represent a protective group; and other symbols are as defined above.

<Step 1>

This step is a method of obtaining a compound represented by the formula 3 by performing a Mitsunobu reaction between a compound represented by the formula 1 and a compound represented by the formula 2 that is a commercially available compound or can be produced by a known method. The Mitsunobu reaction is generally carried out in the presence of a Mitsunobu reagent and a phosphine reagent.

The compound represented by the formula 2 (in the formula 2, $P_1$ represents a protective group for an amino group) can be used in an amount of 1 to 10 equivalents, and preferably 1 to 3 equivalents, based on the amount of the compound represented by the formula 1 (1 mole).

The "protective group for an amino group" is not particularly limited, as long as it has a protective function. Examples of the protective group for an amino group may include: aralkyl groups, such as a benzyl group, a p-methoxybenzyl group, a 3,4-dimethoxybenzyl group, an o-nitrobenzyl group, a p-nitrobenzyl group, a benzhydryl group, a trityl group, and a cumyl group; lower alkanoyl groups, such as, for example, a formyl group, an acetyl group, a propionyl group, a butyryl group, a pivaloyl group, a trifluoroacetyl group, and a trichloroacetyl group; for example, benzoyl groups; arylalkanoyl groups, such as, for example, a phenylacetyl group and a phenoxyacetyl group; lower alkoxycarbonyl groups, such as, for example, a methoxycarbonyl group, an ethoxycarbonyl group, a propyloxycarbonyl group, and a tert-butoxycarbonyl group; aralkyloxycarbonyl groups, such as, for example, a p-nitrobenzyloxycarbonyl group and a phenethyloxycarbonyl group; lower alkylsilyl groups, such as, for example, a trimethylsilyl group and a tert-butyldimethylsilyl group; for example, tetrahydropyranyl groups; for example, trimethylsilylethoxymethyl groups; lower alkylsulfonyl groups, etc., such as, for example, a methylsulfonyl group, an ethylsulfonyl group, and a tert-butylsulfonyl group; lower alkylsulfinyl groups, etc., such as for example, a tert-butylsulfinyl group; arylsulfonyl groups, etc., such as, for example, a benzenesulfonyl group and a toluenesulfonyl group; and imide groups, such as, for example, a phthalimide group. Among these, a trifluoroacetyl group, an acetyl group, a tert-butoxycarbonyl group, a benzyloxycarbonyl group, a trimethylsilylethoxymethyl group, or a cumyl group is particularly preferable.

As a Mitsunobu reagent, diethyl azodicarboxylate, diisopropyl azodicarboxylate or the like is used. Such a Mitsunobu reagent is used in an amount of generally approximately 1 to 100 moles, and preferably approximately 1 to 10 moles, based on the compound represented by the formula 1 (1 mole).

As a phosphine reagent, triphenylphosphine, tributylphosphine, trifurylphosphine or the like is used. Such a phosphine reagent is used in an amount of generally approximately 1 to 100 moles, and preferably approximately 1 to 10 moles, based on the compound represented by the formula 1 (1 mole).

The solvent is not particularly limited, as long as it does not affect the reaction. Examples of the solvent may include hydrocarbons (e.g., benzene, toluene, xylene, etc.), halogenated hydrocarbons (e.g., chloroform, 1,2-dichloroethane, etc.), nitriles (e.g., acetonitrile, etc.), ethers (e.g., dimethoxyethane, tetrahydrofuran, etc.), alcohols (e.g., methanol, ethanol, etc.), aprotic polar solvents (e.g., N,N-dimethylformamide, dimethyl sulfoxide, hexamethylphosphoramide, etc.), water, and mixtures thereof. The reaction time is 0.1 to 100 hours, and preferably 0.5 to 24 hours. Thereafter, the reaction temperature is 0° C. to the temperature at which the solvent is boiled, and preferably 0° C. to 100° C.

The thus obtained compound represented by the formula 3 can be isolated and purified by known separation and purification means, or can be subjected to the subsequent step without isolation and purification.

<Step 2>

This step is a method of obtaining a compound represented by the formula 4 by allowing the compound represented by the formula 3 to react with ammonia or a salt thereof.

The ammonia or a salt thereof can be used in an amount of 1 to 1000 equivalents, and preferably 1 to 100 equivalents, based on the amount of the compound represented by the formula 3 (1 mole).

The solvent is not particularly limited, as long as it does not affect the reaction. Examples of the solvent may include hydrocarbons (e.g., benzene, toluene, xylene, etc.), halogenated hydrocarbons (e.g., chloroform, 1,2-dichloroethane, etc.), nitriles (e.g., acetonitrile, etc.), ethers (e.g., dimethoxyethane, tetrahydrofuran, etc.), alcohols (e.g., methanol, ethanol, etc.), aprotic polar solvents (e.g., N,N-dimethylformamide, dimethyl sulfoxide, hexamethylphosphoramide, etc.), water, and mixtures thereof. The reaction time is 0.1 to 100 hours, and preferably 0.5 to 24 hours. Thereafter, the reaction temperature is 0° C. to the temperature at which the solvent is boiled, and preferably 0° C. to 150° C.

The thus obtained compound represented by the formula 4 can be isolated and purified by known separation and purification means, or can be subjected to the subsequent step without isolation and purification.

<Step 3>

This step is a method of obtaining a compound represented by the formula 5 by reacting the compound represented by the formula 4 under a carbon monoxide atmosphere, for example, in the presence of a transition metal catalyst, a base and alcohol.

In this step, the pressure of the carbon monoxide is generally from 1 to 20 atmospheres, and preferably 1 to 10 atmospheres.

Examples of the alcohol may include methanol, ethanol, propanol, isopropanol, diethylaminoethanol, isobutanol, 4-(2-hydroxyethyl)morpholine, 3-morpholinopropanol, and diethylaminopropanol.

The alcohol is used in an amount of generally approximately 1 to 100 moles, and preferably approximately 1 to 50 moles, based on the amount of the compound represented by the formula 4 (1 mole).

Examples of the transition metal catalyst used herein may include palladium catalysts (e.g., palladium acetate, palladium chloride, tetrakistriphenylphosphine palladium, palladium carbon, etc.). A ligand (e.g., triphenylphosphine, tri-tert-butylphosphine, etc.) may be added, as necessary. The amount of the transition metal catalyst used is different depending on the type of the catalyst. The transition metal catalyst is used in an amount of generally approximately 0.0001 to 1 mole, and preferably approximately 0.01 to 0.5 moles, based on the amount of the compound 4 (1 mole). The ligand is used in an amount of generally approximately 0.0001 to 4 moles, and preferably approximately 0.01 to 2 moles, based on the amount of the compound represented by the formula 4 (1 mole).

Examples of the base may include organic amines (e.g., trimethylamine, triethylamine, diisopropylethylamine, N-methylmorpholine, 1,8-diazabicyclo[5,4,0]undec-7-ene, pyridine, N,N-dimethylaniline, etc.), alkaline metal salts (e.g., sodium hydrogen carbonate, potassium hydrogen carbonate, sodium carbonate, potassium carbonate, cesium carbonate, sodium phosphate, potassium phosphate, sodium hydroxide, potassium hydroxide, etc.), metal hydrides (e.g., potassium hydride, sodium hydride, etc.), alkaline metal alkoxides (e.g., sodium methoxide, sodium ethoxide, sodium-tert-butoxide, potassium-tert-butoxide, etc.), and alkaline metal disilazides (e.g., lithium disilazide, sodium disilazide, potassium disilazide, etc.). Among others, alkaline metal salts such as potassium carbonate, cesium carbonate, sodium phosphate, and potassium phosphate, alkaline metal alkoxides such as sodium-tert-butoxide and potassium-tert-butoxide, organic amines such as triethylamine and diisopropylethylamine, and the like are preferable. The base is used in an amount of generally approximately 0.1 to 50 moles, and preferably approximately 1 to 20 moles, based on the amount of the compound represented by the formula 4 (1 mole).

The solvent is not particularly limited, as long as it does not affect the reaction. Examples of the solvent may include hydrocarbons (e.g., benzene, toluene, xylene, etc.), halogenated hydrocarbons (e.g., chloroform, 1,2-dichloroethane, etc.), nitriles (e.g., acetonitrile, etc.), ethers (e.g., dimethoxyethane, tetrahydrofuran, etc.), alcohols (e.g., methanol, ethanol, etc.), aprotic polar solvents (e.g., N,N-dimethylformamide, dimethyl sulfoxide, hexamethylphosphoramide, N-methylpyrrolidone, etc.), water, and mixtures thereof. The reaction time is 0.1 to 100 hours, and preferably 0.5 to 24 hours. Thereafter, the reaction temperature is 0° C. to the temperature at which the solvent is boiled, and preferably 0° C. to 150° C.

After completion of this reaction, an ester form corresponding to the used alcohol, or a mixture of the ester form and the compound represented by the formula 5 is subjected to a hydrolysis reaction, so that it can be converted to the compound represented by the formula 5.

As such a base, sodium hydrogen carbonate, sodium carbonate, potassium carbonate, cesium carbonate, sodium hydroxide, potassium hydroxide, lithium hydroxide, or the like is preferably used. The base is used in an amount of generally approximately 0.5 to 100 moles, and preferably approximately 1 to 10 moles, based on the amount of the compound represented by the formula 4 (1 mole).

The solvent is not particularly limited, as long as it does not affect the reaction. For example, water, methanol, ethanol, isopropanol, tetrahydrofuran, 1,4-dioxane, N,N-dimethylformamide and the like can be used alone or in combination. The reaction time is 0.1 to 100 hours, and preferably 0.5 to 24 hours. Thereafter, the reaction temperature is 0° C. to the temperature at which the solvent is boiled, and preferably 0° C. to 100° C.

The thus obtained compound represented by the formula 5 can be isolated and purified by known separation and purification means, or can be subjected to the subsequent step without isolation and purification.

<Step 4>

This step is a method of obtaining a compound represented by the formula 6 (wherein $P_2$ represents a protective group for a carboxyl group) by introducing a protective group into the compound represented by the formula 5. Protection can be carried out according to a generally known method, for example, the method described in Protective Groups in Organic Synthesis third edition, T. W. Greene and P. G. M. Wuts, John Wiley & Sons (1999), or a method equivalent thereto.

The "protective group for a carboxyl group" is not particularly limited, as long as it has a protective function. Examples of the protective group for a carboxyl group may include: lower alkyl groups, such as, for example, a methyl group, an ethyl group, a propyl group, an isopropyl group, and a tert-butyl group; halo lower alkyl groups, such as, for example, a 2,2,2-trichloroethyl group; lower alkenyl groups, such as, for example, an allyl group; for example, a trimethylsilylethoxymethyl group; and aralkyl groups, such as, for example, a benzyl group, a p-methoxybenzyl group, a p-nitrobenzyl group, a benzhydryl group, and a trityl group. In particular, a methyl group, an ethyl group, a tert-butyl group, an allyl group, a benzyl group, a p-methoxybenzyl group, or a trimethylsilylethoxymethyl group is preferable.

In the present reaction, a protective group such as, for example, a tert-butyl ester group, a methyl ester group, or an ethyl ester group, is preferably introduced.

The protective group agent used in the present reaction may be, for example, 2-tert-butyl-1,3-diisopropylisourea. Such a protective group agent is used in an amount of generally approximately 1 to 50 moles, and preferably approximately 1 to 10 moles, based on the amount of the compound represented by the formula 5 (1 mole).

The solvent is not particularly limited, as long as it does not affect the reaction. Examples of the solvent may include hydrocarbons (e.g., benzene, toluene, xylene, etc.), halogenated hydrocarbons (e.g., chloroform, 1,2-dichloroethane, etc.), nitriles (e.g., acetonitrile, etc.), ethers (e.g., dimethoxyethane, tetrahydrofuran, tert-butyl methyl ether, etc.), alcohols (e.g., methanol, ethanol, etc.), aprotic polar solvents (e.g., N,N-dimethylformamide, dimethyl sulfoxide, hexamethylphosphoramide, etc.), water, and mixtures thereof. The reaction time is 0.1 to 100 hours, and preferably 0.5 to 24 hours. Thereafter, the reaction temperature is 0° C. to the temperature at which the solvent is boiled, and preferably 0° C. to 100° C.

The thus obtained compound represented by the formula 6 can be isolated and purified by known separation and purification means, or can be subjected to the subsequent step without isolation and purification.

<Step 5>

This step is a method of obtaining a compound represented by the formula 7 (wherein $L_3$ represents a halogen atom) by halogenating the compound represented by the formula 6. Halogenation can be carried out by a method using fluorine, chlorine, bromine, iodine, etc., or by a method using N-chlorosuccinimide, N-bromosuccinimide, N-iodosuccinimide, etc. In the present reaction, the method using N-chlorosuccinimide, N-bromosuccinimide, N-iodosuccinimide, etc. is preferable.

N-chlorosuccinimide, N-bromosuccinimide, N-iodosuccinimide, etc. can be used in an amount of 1 to 10 equivalents, and preferably 1 to 3 equivalents, based on the amount of the compound represented by the formula 6 (1 mole).

The solvent is not particularly limited, as long as it does not affect the reaction. Examples of the solvent may include hydrocarbons (e.g., benzene, toluene, xylene, etc.), halogenated hydrocarbons (e.g., chloroform, 1,2-dichloroethane, etc.), nitriles (e.g., acetonitrile, etc.), ethers (e.g., dimethoxyethane, tetrahydrofuran, etc.), alcohols (e.g., methanol, ethanol, etc.), aprotic polar solvents (e.g., N,N-dimethylformamide, dimethyl sulfoxide, hexamethylphosphoramide, etc.), water, and mixtures thereof. The reaction time is 0.1 to 100 hours, and preferably 0.5 to 24 hours. Thereafter, the reaction temperature is 0° C. to the temperature at which the solvent is boiled, and preferably 0° C. to 100°.

The thus obtained compound represented by the formula 7 can be isolated and purified by known separation and purification means, or can be subjected to the subsequent step without isolation and purification.

<Step 6>

This step is a method of obtaining a compound represented by the formula 8 by removing the protective group for an amino group ($P_1$ in the formula 7) from the compound represented by the formula 7 (deprotection). Such deprotection can be carried out according to a generally known method, for example, the method described in Protective Groups in Organic Synthesis third edition, T. W. Greene and P. G. M. Wuts, John Wiley & Sons (1999), or a method equivalent thereto.

The protective group may be, for example, tert-butyloxycarbonyl. When such a tert-butyloxycarbonyl group is used, for example, as a protective group, deprotection is preferably carried out under acidic conditions. Examples of the acid used herein may include hydrochloric acid, acetic acid, trifluoroacetic acid, sulfuric acid, and tosylic acid.

The acid is preferably used in an amount of approximately 1 to 100 equivalents based on the amount of the compound represented by the formula 7 (1 mole).

The solvent used in the reaction is not particularly limited, as long as it does not affect the reaction. Examples of the solvent used herein may include alcohols (e.g., methanol, etc.), hydrocarbons (e.g., benzene, toluene, xylene, etc.), halogenated hydrocarbons (e.g., methylene chloride, chloroform, 1,2-dichloroethane, etc.), nitriles (e.g., acetonitrile, etc.), ethers (e.g., dimethoxyethane, tetrahydrofuran, etc.), aprotic polar solvents (e.g., N,N-dimethylformamide, dimethyl sulfoxide, hexamethylphosphoramide, etc.), and mixtures thereof. The reaction time is 0.1 to 100 hours, and preferably 0.5 to 24 hours. Thereafter, the reaction temperature is 0° C. to 100° C., and preferably 0° C. to 500.

The thus obtained compound represented by the formula 8 can be isolated and purified by known separation and purification means, or can be subjected to the subsequent step without isolation and purification.

<Step 7>

This step is a method of obtaining a compound represented by the formula 9 by performing an amidation reaction between an amino group of the compound represented by the formula 8 and acrylic acid halide or acrylic acid anhydride.

In the case of using acrylic acid halide or acrylic acid anhydride, such acrylic acid halide or acrylic acid anhydride is used in an amount of generally approximately 0.5 to 10 moles, and preferably approximately 1 to 5 moles, based on the amount of the compound represented by the formula 8 (1 mole). It is to be noted that the present acrylic acid halide or acrylic acid anhydride can be obtained as a commercially available product or can be produced according to a known method.

In addition, a base can be added, as necessary. Examples of the base may include organic amines (e.g., trimethylamine, triethylamine, isopropylethylamine, diisopropylethylamine, N-methylmorpholine, 1,8-diazabicyclo[5,4,0]undec-7-ene, pyridine, N,N-dimethylaniline, etc.), alkaline metal salts (e.g., sodium hydrogen carbonate, potassium hydrogen carbonate, sodium carbonate, potassium carbonate, cesium carbonate, sodium phosphate, potassium phosphate, sodium hydroxide, potassium hydroxide, etc.), metal hydrides (e.g., potassium hydride, sodium hydride, etc.), and alkaline metal alkoxides (e.g., sodium methoxide, sodium ethoxide, sodium-tert-butoxide, potassium-tert-butoxide, etc.). The base is used in an amount of generally approximately 1 to 100 moles, and preferably approximately 1 to 10 moles, based on the amount of the compound represented by the formula 8 (1 mole).

The solvent used in the reaction is not particularly limited, as long as it does not affect the reaction. Examples of the solvent used herein may include alcohols (e.g., methanol, etc.), hydrocarbons (e.g., benzene, toluene, xylene, etc.), halogenated hydrocarbons (e.g., methylene chloride, chloroform, 1,2-dichloroethane, etc.), nitriles (e.g., acetonitrile, etc.), ethers (e.g., dimethoxyethane, tetrahydrofuran, etc.), aprotic polar solvents (e.g., N,N-dimethylformamide, dimethyl sulfoxide, hexamethylphosphoramide, etc.), and mixtures thereof. The reaction time is 0.1 to 100 hours, and preferably 0.5 to 24 hours. Thereafter, the reaction temperature is 0° C. to the temperature at which the solvent is boiled, and preferably 0° C. to 100° C.

The thus obtained compound represented by the formula 9 can be isolated and purified by known separation and purification means, or can be subjected to the subsequent step without isolation and purification.

<Step 8>

This step is a method of obtaining a compound represented by the formula 10 by performing a Sonogashira reaction between the compound represented by the formula 9 and an acetylene derivative that is a commercially available product or can be produced by a known method.

The acetylene derivative can be used in an amount of 1 to 50 equivalents, and preferably 1 to 10 equivalents, based on the amount of the compound represented by the formula 9 (1 mole).

Examples of the transition metal catalyst used herein may include palladium catalysts (e.g., palladium acetate, palladium chloride, tetrakistriphenylphosphinepalladium, dichlorobis(triphenylphosphine)palladium, dichlorobis(triphenylphosphine)dipalladium, etc.), and nickel catalysts (e.g., nickel chloride, etc.). As necessary, a ligand (e.g., triphenylphosphine, tri-tert-butylphosphine, etc.) may be added, and a copper catalyst (e.g., copper iodide, copper bromide, or copper chloride) or the like may be used as a co-catalyst. The amount of the transition metal catalyst used is different depending on the type of the catalyst. The transition metal catalyst is used in an amount of generally approximately 0.0001 to 1 mole, and preferably approximately 0.01 to 0.5 moles, based on the amount of the compound represented by the formula 9 (1 mole). The ligand is used in an amount of generally approximately 0.0001 to 4 moles, and preferably approximately 0.01 to 2 moles, based on the amount of the compound represented by the formula 9 (1 mole). The copper catalyst is used in an amount of generally approximately 0.0001 to 4 moles, and preferably approximately 0.010 to 2 moles, based on the amount of the compound represented by the formula 9 (1 mole).

Examples of the base may include organic amines (e.g., trimethylamine, triethylamine, diisopropylethylamine, N-methylmorpholine, 1,8-diazabicyclo[5,4,0]undec-7-ene, pyridine, N,N-dimethylaniline, etc.), alkaline metal salts (e.g., sodium hydrogen carbonate, potassium hydrogen carbonate, sodium carbonate, potassium carbonate, cesium carbonate, sodium phosphate, potassium phosphate, sodium hydroxide, potassium hydroxide, etc.), metal hydrides (e.g., potassium hydride, sodium hydride, etc.), alkaline metal alkoxides (e.g., sodium methoxide, sodium ethoxide, sodium-tert-butoxide, potassium-tert-butoxide, etc.), and alkaline metal disilazide (e.g., lithium disilazide, sodium disilazide, potassium disilazide, etc.). Among these, preferred examples of the base may include: alkaline metal salts, such as potassium carbonate, cesium carbonate, sodium phosphate, and potassium phosphate; alkaline metal alkoxides, such as sodium-tert-butoxide and potassium-tert-butoxide; and organic amines, such as triethylamine and diisopropylethylamine. The base is used in an amount of generally approximately 0.1 to 10 moles, and preferably approximately 1 to 5 moles, based on the amount of the compound represented by the formula 9 (1 mole).

The solvent is not particularly limited, as long as it does not affect the reaction. Examples of the solvent may include hydrocarbons (e.g., benzene, toluene, xylene, etc.), halogenated hydrocarbons (e.g., chloroform, 1,2-dichloroethane, etc.), nitriles (e.g., acetonitrile, etc.), ethers (e.g., dimethoxyethane, tetrahydrofuran, etc.), alcohols (e.g., methanol, ethanol, etc.), aprotic polar solvents (e.g., N,N-dimethylformamide, dimethyl sulfoxide, hexamethylphosphoramide, etc.), water, and mixtures thereof. The reaction time is 0.1 to 100 hours, and preferably 0.5 to 24 hours. Thereafter, the reaction temperature is 0° C. to the temperature at which the solvent is boiled, and preferably 0° C. to 150° C.

The thus obtained compound represented by the formula 10 can be isolated and purified by known separation and purification means, or can be subjected to the subsequent step without isolation and purification.

<Step 9>

This step is a method of obtaining a compound represented by the formula 11 by deprotecting the protective group for a carboxyl group ($P_2$ in the formula 10) of the compound represented by the formula 10. Deprotection can be carried out according to a generally known method, for example, the method described in Protective Groups in Organic Synthesis third edition, T. W. Greene and P. G. M. Wuts, John Wiley & Sons (1981), or a method equivalent thereto.

The protective group may be, for example, tert-butyl ester. When such a tert-butyl ester group is used as a protective group, for example, deprotection is preferably carried out under acidic conditions. Examples of the acid used herein may include hydrochloric acid, acetic acid, trifluoroacetic acid, sulfuric acid, and tosylic acid.

The acid is preferably used in an amount of approximately 1 to 100 equivalents based on the amount of the compound represented by the formula 10 (1 mole).

The solvent used in the reaction is not particularly limited, as long as it does not affect the reaction. Examples of the solvent used herein may include alcohols (e.g., methanol, etc.), hydrocarbons (e.g., benzene, toluene, xylene, etc.), halogenated hydrocarbons (e.g., methylene chloride, chloroform, 1,2-dichloroethane, etc.), nitriles (e.g., acetonitrile, etc.), ethers (e.g., dimethoxyethane, tetrahydrofuran, etc.), aprotic polar solvents (e.g., N,N-dimethylformamide, dimethyl sulfoxide, hexamethylphosphoramide, etc.), and mixtures thereof. The reaction time is 0.1 to 100 hours, and preferably 0.5 to 24 hours. Thereafter, the reaction temperature is 0° C. to 100° C., and preferably 0° C. to 500.

The thus obtained compound represented by the formula 11 can be isolated and purified by known separation and purification means, or can be subjected to the subsequent step without isolation and purification.

<Step 10>

This step is a method of obtaining a compound represented by the formula (I) by performing an amidation reaction between a carboxyl group of the compound represented by the formula 11 and an amine that is a commercially available product or can be produced by a known method.

Amidation can be carried out according to a conventionally known method. Examples of the amidation method may include a method of performing the reaction in the presence of a condensing agent, and a method comprising activating a carboxylic acid portion according to a conventionally known method to obtain a reactive derivative, and then performing amidation between the derivative and an amine (for both methods, see *Peptide Gosei no Kiso to Jikken* (Principle of Peptide Synthesis and Experiments)" (Nobuo IZUMIYA et al., Maruzen Co., Ltd., 1983)).

Examples of the condensing agent may include N,N'-dicyclohexylcarbodiimide (DCC), N,N'-diisopropylcarbodiimide (DIC), 1-ethyl-3-(3-dimethylaminopropyl)carbodiimide hydrochloride (WSC), diphenylphosphoryl azide (DPPA), benzotriazol-1-yl-oxytrisdimethylaminophosphonium hexafluorophosphate (BOP), benzotriazol-1-yl-oxytripyrrolidinophosphoniumhexafluorophosphate (PyBOP), 7-azabenzotriazol-1-yloxytrispyrrolidinophosphonium phosphate (PyAOP), bromotrispyrrolidinophosphonium hexafluorophosphate (BroP), chlorotris(pyrrolidin-1-yl)phosphonium hexafluorophosphate (PyCroP), 3-(diethoxyphosphoryloxy)-1,2,3-benzotriazin-4(3H)-one (DEPBT), O-(azabenzotriazol-1-yl)-N,N,N',N'-tetramethyluronium hexafluorophosphate (HATU), and 4-(5,6-dimethoxy-1,3,5-triazin-2-yl)-4-methylmorpholine hydrochloride (DMTMM). Examples of the additive used at that time may include 1-hydroxybenzotriazole (HOBt), 1-hydroxy-7-azabenzotriazole (HOAt), and N-hydroxysuccinimide (HOSu). Such agents are used in an amount of generally approximately 1 to 100 moles, and preferably approximately 1 to 10 moles, based on the amount of the compound represented by the formula 11 (1 mole).

In addition, as necessary, a base can be added. Examples of such a base may include organic amines (e.g., trimethylamine, triethylamine, diisopropylethylamine, N-methylmorpholine, 1,8-diazabicyclo[5,4,0]undec-7-ene, pyridine, N,N-dimethylaniline, etc.), alkaline metal salts (e.g., sodium hydrogen carbonate, potassium hydrogen carbonate, sodium carbonate, potassium carbonate, cesium carbonate, sodium phosphate, potassium phosphate, sodium hydroxide, potassium hydroxide, etc.), metal hydrides (e.g., potassium hydride, sodium hydride, etc.), and alkaline metal alkoxides (e.g., sodium methoxide, sodium ethoxide, sodium-tert-butoxide, potassium-tert-butoxide, etc.). The base is used in an amount of generally approximately 1 to 100 moles, and preferably approximately 1 to 10 moles, based on the amount of the compound represented by the formula 11 (1 mole).

The solvent used in the reaction is not particularly limited, as long as it does not affect the reaction. Examples of the solvent used herein may include alcohols (e.g., methanol, etc.), hydrocarbons (e.g., benzene, toluene, xylene, etc.), halogenated hydrocarbons (e.g., methylene chloride, chloroform, 1,2-dichloroethane, etc.), nitriles (e.g., acetonitrile, etc.), ethers (e.g., dimethoxyethane, tetrahydrofuran, etc.), aprotic polar solvents (e.g., N,N-dimethylformamide, dimethyl sulfoxide, hexamethylphosphoramide, etc.), and mixtures thereof. The reaction time is 0.1 to 100 hours, and preferably 0.5 to 24 hours. Thereafter, the reaction temperature is 0° C. to the temperature at which the solvent is boiled, and preferably 0° C. to 100° C.

The thus obtained compound (I) can be isolated and purified according to known separation and purification means, such as, for example, concentration, vacuum concentration, crystallization, solvent extraction, re-precipitation, or chromatography.

In the above-described production method, the steps ranging from the "introduction of a protective group into a carboxyl group of the compound represented by the formula 5" (Step 4) to the "amidation reaction between a carboxyl group of the compound represented by the formula 11 and an amine that is a commercially available product or can be produced by a known method" (Step 10) are successively carried out in this order. However, the order of performing these steps can be changed. Moreover, the "introduction of a protective group into a carboxyl group of the compound represented by the formula 5" (Step 4) and the "removal of the protective group for a carboxy group from the compound represented by the formula 10" (Step 9) can be omitted.

Specifically, individual steps are carried out in the order of the "amidation reaction between a carboxyl group of the compound represented by the formula 11 and an amine that is a commercially available product or can be produced by a known method" (Step 10), the "halogenation of the compound represented by the formula 6" (Step 5), the "removal of the protective group for an amino group from the compound represented by the formula 7" (Step 6), the "amidation reaction between an amino group of the compound represented by the formula 8 and acrylic acid halide or acrylic acid anhydride" (Step 7), and the "Sonogashira reaction between the compound represented by the formula 9 and an acetylene derivative that is a commercially available product or can be produced by a known method, when L3 of the compound represented by the formula 9 has a leaving group such as halogen" (Step 8), so that the concerned compound can be induced to the compound represented by the formula (I). The conditions applied in individual steps are the same as those as described above.

When the compound of the present invention has an isomer, such as an optical isomer, a stereoisomer, a rotational isomer, or a tautomer, all of these isomers or mixtures thereof are included in the compound of the present invention, unless otherwise stated. For example, when the compound of the present invention has an optical isomer, both a racemate, and an optical isomer obtained as a result of racemic resolution are included in the compound of the present invention, unless otherwise stated.

The salt of the compound of the present invention means a pharmaceutically acceptable salt, and it may be, for example, a base-added salt or an acid-added salt.

The compound of the present invention or a salt thereof also includes a prodrug. The "prodrug" means a compound that is converted to the compound of the present invention or a salt thereof as a result of the reaction with an enzyme, stomach acid, etc. under physiological conditions in a living body; namely, a compound that enzymatically causes oxidation, reduction, hydrolysis, etc., so that it is converted to the compound of the present invention or a salt thereof, or a compound that causes hydrolysis, etc. with stomach acid or the like, so that it is converted to the compound of the present invention or a salt thereof. Otherwise, it may also be a compound that is converted to the compound of the present invention or a salt thereof under physiological conditions as described in "*Iyakuhin no Kaihatsu* (Development of Pharmaceutical Products)," Hirokawa Shoten, 1990, Vol. 7, *Bunshi Sekkei* (Molecular Designing), pp. 163 to 198.

The compound of the present invention or a salt thereof may be an amorphous material or a crystal. Although the crystal form thereof may be a single crystal or a polymorphic mixture, they are included in the compound of the present invention or a salt thereof. The crystal can be produced by crystallizing the compound of the present invention or a salt thereof, applying a known crystallization method. The compound of the present invention or a salt thereof may be either a solvate (e.g., a hydrate, etc.), or a non-solvate, and both of them are included in the compound of the present invention or a salt thereof. Compounds labeled with radioisotopes (e.g., $^3$H, $^{14}$C, $^{35}$S, $^{125}$I, etc.) and the like are also included in the compound of the present invention or a salt thereof.

The compound of the present invention or a salt thereof has excellent HER2 inhibitory activity. Moreover, the compound of the present invention or a salt thereof has excellent selectivity to HER2. Accordingly, the compound of the present invention or a salt thereof is useful as an antitumor agent against malignant tumor having HER2 overexpression, HER2 gene amplification, HER2 mutation, etc. In addition, since significant weight reduction was not found in mice, the present compound or a salt thereof is advantageous in that it has a few side effects.

In the present description, the term "HER2" includes the HER2 of a human or a non-human mammal, and it is preferably human HER2. Furthermore, the term "HER2" includes isoforms.

Since the compound of the present invention or a salt thereof has excellent HER2 inhibitory activity, it is useful as a medicament for preventing or treating disease associated with HER2.

The "disease associated with HER2" means disease, in which a reduction in the incidence, or the remission, alleviation and/or complete recovery of the symptoms thereof is achieved by deleting, suppressing and/or inhibiting the function of HER2. Examples of such disease may include malignant tumors, but are not limited thereto. Preferred examples of the disease may include malignant tumors having HER2 overexpression, HER2 gene amplification, or HER2 mutation.

One embodiment of the present invention provides an inhibitor against HER2, comprising the compound of the present invention or a salt thereof. In addition, one embodiment of the present invention provides a method for inhibiting HER2, comprising administering an effective amount of the compound of the present invention or a salt thereof to a subject in need thereof. Moreover, one embodiment of the present invention provides use of the compound of the present invention or a salt thereof for the production of a HER2 inhibitor. Furthermore, one embodiment of the present invention provides the compound of the present invention or a salt thereof for use as a HER2 inhibitor. Furthermore, one embodiment of the present invention provides use of the compound of the present invention or a salt thereof for inhibiting HER2. In another embodiment, the present invention provides use of the compound of the present invention or a salt thereof for preventing or treating disease associated with HER2.

Another embodiment of the present invention provides an antitumor agent comprising the compound of the present invention or a salt thereof. In addition, one embodiment of the present invention provides a method for preventing and/or treating tumor, comprising administering an effective amount of the compound of the present invention or a salt thereof to a subject in need thereof. One embodiment of the present invention provides use of the compound of the present invention or a salt thereof for the production of an antitumor agent.

Moreover, one embodiment of the present invention provides the compound of the present invention or a salt thereof for use in the prevention and/or treatment of tumor.

The compound according to one embodiment of the present invention or a salt thereof selectively inhibits wild-type HER2, and mutant HER2 having one or more insertion mutations, point mutations, deletion mutations, etc. in the HER2 domain thereof, such as exon 20 insertion mutation. One embodiment of the present invention provides: a compound having inhibitory activity against wild-type HER2, and mutant HER2 including HER2 having YVMA insertion mutation that is one of exon 20 insertion mutations, or a salt thereof; or a medicament or a pharmaceutical composition each comprising the same. One embodiment of the present invention provides an inhibitor against wild-type HER2, and mutant HER2 including HER2 having YVMA insertion mutation, etc., wherein the inhibitor comprises the compound of the present invention or a salt thereof. In addition, one embodiment of the present invention provides a method for inhibiting wild-type HER2, and mutant HER2 including HER2 having YVMA insertion mutation, etc., wherein the method comprises administering an effective amount of the compound of the present invention or a salt thereof to a subject in need thereof. Moreover, one embodiment of the present invention provides use of the compound of the present invention or a salt thereof for the production of an inhibitor against wild-type HER2, and mutant HER2 including HER2 having YVMA insertion mutation, etc. Furthermore, one embodiment of the present invention provides the compound of the present invention or a salt thereof for use as an inhibitor against wild-type HER2, and mutant HER2 including HER2 having YVMA insertion mutation, etc. Further, one embodiment of the present invention provides use of the compound of the present invention or a salt thereof for inhibiting wild-type HER2, and mutant HER2 including HER2 having YVMA insertion mutation, etc. In another embodiment, the present invention provides use of the compound of the present invention or a salt thereof for preventing or treating disease associated with wild-type HER2, and mutant HER2 including HER2 having YVMA insertion mutation, etc.

The human HER2 gene is shown in, for example, SEQ ID NO: 1, SEQ ID NO: 3, or SEQ ID NO: 5. The wild-type HER2 protein consists of the amino acid sequence set forth in, for example, SEQ ID NO: 2, SEQ ID NO: 4, or SEQ ID NO: 6. The nucleotide sequence information of the human HER2 gene and the amino acid sequence information of the wild-type HER2 protein can be obtained from, for example, Accession No. NM_004448, NM_001289936, NM_001005862, or the like.

In several embodiments, the compound of one embodiment of the present invention or a salt thereof exhibits inhibitory activity against mutant HER2 comprising one or more mutations from G309A, S310F, R678Q, L755S, L755_T759del, D769H, A775_G776insYVMA, V777L, V842I and R896C, using the amino acid sequence set forth in SEQ ID NO: 2 as a reference. In another embodiment, the compound of one embodiment of the present invention or a salt thereof exhibits inhibitory activity against mutant HER2 comprising A775_G776insYVMA, using the amino acid sequence set forth in SEQ ID NO: 2 as a reference.

In several embodiments, the compound of one embodiment of the present invention or a salt thereof exhibits inhibitory activity against mutant HER2 comprising one or more mutations from G294A, S295F, R663Q, L740S, L740_T744del, D754H, A760_G761insYVMA, V762L, V827I and R881C, using the amino acid sequence set forth in SEQ ID NO: 4 as a reference. In another embodiment, the compound of one embodiment of the present invention or a salt thereof exhibits inhibitory activity against mutant HER2 comprising A760_G761insYVMA, using the amino acid sequence set forth in SEQ ID NO: 4 as a reference.

In several embodiments, the compound of one embodiment of the present invention or a salt thereof exhibits inhibitory activity against mutant HER2 comprising one or more mutations from G279A, S280F, R648Q, L725S, L725_T729del, D739H, A745_G746insYVMA, V747L, V812I and R866C, using the amino acid sequence set forth in SEQ ID NO: 6 as a reference. In another embodiment, the compound of one embodiment of the present invention or a salt thereof exhibits inhibitory activity against mutant HER2 comprising A745_G746insYVMA, using the amino acid sequence set forth in SEQ ID NO: 6 as a reference.

Further, in several embodiments, with regard to a mutation in a certain HER2 isoform, even when the position of the mutation is different from the position of an amino acid shown in SEQ ID NO: 2 due to deletion or insertion of an amino acid(s), it is understood that the mutation is the same as the mutation at a position corresponding to the position of the amino acid shown in SEQ ID NO: 2. Hence, for example, the glycine at position 309 in the HER2 shown in SEQ ID NO: 2 corresponds to glycine at position 294 in HER2 consisting of the amino acid sequence set forth in SEQ ID NO: 4. For example, the term "G309A" means that the glycine at position 309 in the HER2 shown in SEQ ID NO: 2 is mutated to alanine. Since such "G309" is at a position corresponding to the amino acid at position 294 in HER2 consisting of the amino acid sequence set forth in SEQ ID NO: 4, "G294A" in the HER2 consisting of the amino acid sequence set forth in SEQ ID NO: 4 corresponds to "G309A" in the HER2 shown in SEQ ID NO: 2. Besides, the position of an amino acid in SEQ ID NO: 2 that corresponds to a certain amino acid in a certain HER2 isoform can be confirmed by Multiple Alignment of BLAST.

SEQUENCE LISTING

TABLE A

```
SEQ ID NO: 1
Accession No.: NM _ 004448
CDS: 262 . . . 4029
    1 gcttgctccc aatcacagga gaaggaggag gtggaggagg agggctgctt gaggaagtat
   61 aagaatgaag ttgtgaagct gagattcccc tccattggga ccggagaaac caggggagcc
  121 ccccgggcag ccgcgcgccc cttcccacgg ggccctttac tgcgccgcgc gcccggcccc
  181 cacccctcgc agcaccccgc gccccgccgc ctcccagccg ggtccagccg gagccatggg
  241 gccggagccg cagtgagcac catggagctg gcggccttgt gccgctgggg gctcctcctc
  301 gccctcttgc ccccggagc cgcgagcacc caagtgtgca ccggcacaga catgaagctg
  361 cggctccctg ccagtccga gacccacctg gacatgctcc gccacctcta ccagggctgc
  421 caggtggtgc agggaaacct ggaactcacc tacctgccca ccaatgccag cctgtccttc
  481 ctgcaggata tccaggaggt gcagggctac gtgctcatcg ctcacaacca agtgaggcag
  541 gtcccactgc agaggctgcg gattgtgcga ggcacccagc tctttgagga caactatgcc
  601 ctggccgtgc tagacaatgg agacccgctg aacaatacca ccctgtcac aggggcctcc
  661 ccaggaggcc tgcgggagct gcagcttcga agcctcacag agatcttgaa aggaggggtc
  721 ttgatccagc ggaaccccca gctctgctac caggacacga ttttgtggaa ggacatcttc
  781 cacaagaaca accagctggc tctcacactg atagacacca accgctctcg ggcctgccac
  841 ccctgttctc cgatgtgtaa gggctcccgc tgctggggag agagttctga ggattgtcag
  901 agcctgacgc gcactgtctg tgccggtggc tgtgcccgct gcaagggggcc actgcccact
  961 gactgctgcc atgagcagtg tgctgccgcc tgcacgggcc ccaagcactc tgactgcctg
 1021 gcctgcctcc acttcaacca cagtggcatc tgtgagctgc actgcccagc cctggtcacc
 1081 tacaacacag acacgtttga gtccatgccc aatcccgagg gccggtatac attcggcgcc
 1141 agctgtgtga ctgcctgtcc ctacaactac ctttctacgg acgtgggatc ctgcaccctc
 1201 gtctgccccc tgcacaacca agaggtgaca gcagaggatg gaacacagcg tgtgagaag
 1261 tgcagcaagc cctgtgcccg agtgtgctat ggtctgggca tggagcactt gcgagaggtg
 1321 agggcagtta ccagtgccaa tatccaggag tttgctggct gcaagaagat ctttgggagc
 1381 ctggcatttc tgccggagag ctttgatggg gacccagcct ccaacactgc ccgctccag
 1441 ccagagcagc tccaagtgtt tgagactctg gaagagatca caggttacct atacatctca
 1501 gcatggccgg acagcctgcc tgacctcagc gtcttccaga acctgcaagt aatccgggga
 1561 cgaattctgc accaatggca ctactggctg acctgcaag ggctgggcat cagctggctg
 1621 gggctgcgct cactgaggga actgggcagt ggactggccc tcatccacca taacacccac
 1681 ctctgcttcg tgcacacggt gccctggac cagctctttc ggaacccgca ccaagctctg
 1741 ctccacactg ccaaccggcc agaggacgag tgtgtgggcg aggggcctggc ctgccaccag
 1801 ctgtgcgccc gagggcactg ctggggtcca gggcccaccc agtgtgtcaa ctgcagccag
 1861 ttccttcggg gccaggagtg cgtggaggaa tgccgagtac tgcagggggct ccccagggag
```

TABLE A-continued

```
1921 tatgtgaatg ccaggcactg tttgccgtgc caccctgagt gtcagcccca gaatggctca
1981 gtgacctgtt ttggaccgga ggctgaccag tgtgtggcct gtgccactca taaggaccct
2041 cccttctgcg tggcccgctg ccccagcggt gtgaaacctg acctctccta catgcccatc
2101 tggaagtttc cagatgagga gggcgcatgc cagccttgcc ccatcaactg cacccactcc
2161 tgtgtggacc tggatgacaa gggctgcccc gccgacgaga gagccagcct tctgacgtcc
2221 atcatctctg cggtggttgg cattctgctg gtcgtggtct tgggggtggt ctttgggatc
2281 ctcatcaagc gacggcagca agatccgg aagtacacga tgcggagact gctgcaggaa
2341 acggagctgg tggagccgct gacacctagc ggagcgatgc caaccaggc gcagatgcgg
2401 atcctgaaag agacggagct gaggaaggtg aagtgcttg gatctggcgc ttttggcaca
2461 gtctacaagg gcatctggat ccctgatggg gagaatgtga aaattccagt ggccatcaaa
2521 gtgttgaggg aaaacacatc ccccaaagcc aacaaagaaa tcttagacga agcatacgtg
2581 atggctggtg tgggctcccc atatgtctcc cgccttctgg gcatctgcct gacatccacg
2641 gtgcagctgg tgacacagct tatgcccat ggctgcctct tagaccatgt ccgggaaaac
2701 cgcggacgcc tgggctccca ggacctgctg aactggtgta tgcagattgc caaggggat
2761 agctacctgg aggatgtgcg gctcgtacac agggacttgg ccgctcggaa cgtgctggtc
2821 aagagtccca accatgtcaa aattacagac ttcgggctgg ctcggctgct ggacattgac
2881 gagacagagt accatgcaga tgggggcaag gtgcccatca atggatggc gctgagtcc
2941 attctccgcc ggcggttcac ccaccagagt gatgtgtgga gttatggtgt gactgtgtgg
3001 gagctgatga cttttgggc caaaccttac gatgggatcc cagcccggga gatccctgac
3061 ctgctggaaa aggggagcg gctgcccag cccccatct gcaccattga tgtctacatg
3121 atcatggtca aatgttggat gattgactct gaatgctccg caagattccg ggagttggtg
3181 tctgaattct cccgcatggc cagggacccc cagcgctttg tggtcatcca gaatgaggac
3241 ttgggcccag ccagtccctt ggacagcacc ttctaccgct cactgctgga ggacgatgac
3301 atggggacc tggtggatgc tgaggagtat ctggtacccc agcagggctt cttctgtcca
3361 gaccctgccc cgggcgctgg gggcatggtc caccacaggc accgcagctc atctaccagg
3421 agtggcggtg gggacctgac actagggctg gagccctg aagaggaggc cccaggtct
3481 ccactggcac cctccgaagg ggctggctcc gatgtatttg atggtgacct gggaatgggg
3541 gcagccaagg ggctgcaaag cctccccaca catgacccca gccctctaca gcggtacagt
3601 gaggacccca cagtaccct gccctctgag actgatggct acgttgcccc cctgacctgc
3661 agccccagc ctgaatatgt gaaccagcca gatgttcggc cccagccccc ttcgccccga
3721 gagggccctc tgcctgctgc ccgacctgct ggtgccactc tggaaaggcc caagactctc
3781 tccccaggga agaatggggt cgtcaaagac gtttttgcct tggggggtgc cgtggagaac
3841 cccgagtact tgacacccca gggaggagct gcccctcagc ccacccctcc tcctgccttc
3901 agcccagcct tcgacaacct ctattactgg gaccaggacc caccagagcg ggggcctcca
3961 cccagcacct tcaaagggac acctacggca gagaacccag agtacctggg tctggacgtg
4021 ccagtgtgaa ccagaaggcc aagtccgcag aagcccgat gtgtcctcag ggagcaggga
4081 aggcctgact tctgctggca tcagaggtg ggagggcccc ccgaccactt ccaggggaac
4141 ctgccatgcc aggaacctgt cctaaggaac cttccttcct ccagatggct
4201 ggaaggggtc cagcctcgtt ggaagaggaa cagcactggg gagtctttgt ggattctgag
4261 gccctgccca atgagactct agggtccagt ggatgccaca gcccagcttg ccctttcct
4321 tccagatcct gggtactgaa agccttaggg aagctggcct gagaggggaa gcggccctaa
4381 gggagtgtct aagaacaaaa gcgacccatt cagagactgt ccctgaaacc tagtacgac
4441 ccccatgagg aaggaacagc aatggtgtca gtatccaggc tttgtacaga gtgctttct
4501 gtttagtttt tacttttttt gttttgtttt tttaaagatg aaataaagac ccaggggag
4561 aatgggtgtt gtatggggag gcaagtgtgg ggggtccttc tccacaccca ctttgtccat
4621 ttgcaaatat attttggaaa acagctaaaa aaaaaaaaa aaaa
```

SEQ ID NO: 2
Accession No.: NM_004448
```
MELAALCRWG LLLLALLPPGA ASTQVCTGTD MKLRLPASPE THLDMLRHLY QGCQVVQGNL    60
ELTYLPTNAS LSFLQDIQEV QGYVLIAHNQ VRQVPLQRLR IVRGTQLFED NYALAVLDNG   120
DPLNNTTPVT GASPGGLREL QLRSLTEILK GGVLIQRNPQ LCYQDTILWK DIFHKNNQLA   180
LTLIDTNRSR ACHPCSPMCK GSRCWGESSE DCQSLTRTVC AGGCARCKGP LPTDCCHEQC   240
AAGCTGPKHS DCLACLHFNH SGICELHCPA LVTYNTDTFE SMPNPEGRYT FGASCVTACP   300
YNYLSTDVGS CTLVCPLHNQ EVTAEDGTQR CEKCSKPCAR VCYGLGMEHL REVRAVTSAN   360
IQEFAGCKKI FGSLAFLPES FDGDPASNTA PLQPEQLQVF ETLEEITGYL YISAWPDSLP   420
DLSVFQNLQV IRGRILHNGA YSLTLQGLGI SWLGLRSLRE LGSGLALIHH NTHLCFVHTV   480
PWDQLFRNPH QALLHTANRP EDECVGEGLA CHQLCARGHC WGPGPTQCVN CSQFLRGQEC   540
VEECRVLQGL PREYVNARHC LPCHPECQPQ NGSVTCFGPE ADQCVACAHY KDPPFCVARC   600
PSGVKPDLSY MPIWKFPDEE GACQPCPINC THSCVDLDDK GCPAEQRASP LTSIISAVVG   660
ILLVVVLGVV FGILIKRRQQ KIRKYTMRRL LQETELVEPL TPSGAMPNQA QMRILKETEL   720
RKVKVLGSGA FGTVYKGIWI PDGENVKIPV AIKVLRENTS PKANKEILDE AYVMAGVGSP   780
YVSRLLGICL TSTVQLVTQL MPYGCLLDHV RENRGRLGSQ DLLNWCMQIA KGMSYLEDVR   840
LVHRDLAARN VLVKSPNHVK ITDFGLARLL DIDETEYHAD GGKVPIKWMA LESILRRRFT   900
HQSDVWSYGV TVWELMTFGA KPYDGIPARE IPDLLEKGER LPQPPICTID VYMIMVKCWM   960
IDSECRPRFR ELVSEFSRMA RDPQRFVVIQ NEDLGPASPL DSTFYRSLLE DDDMGDLVDA  1020
EEYLVPQQGF FCPDPAPGAG GMVHHRHRSS STRSGGGDLT LGLEPSEEEA PRSPLAPSEG  1080
AGSDVFDGDL GMGAAKGLQS LPTHDPSPLQ RYSEDPTVPL PSETDGYVAP LTCSPQPEYV  1140
NQPDVRPQPP SPREGPLPAA RPAGATLERP KTLSPGKNGV VKDVFAFGGA VENPEYLTPQ  1200
GGAAPQPHPP PAFSPAFDNL YYWDQDPPER GAPPSTFKGT PTAENPEYLG LDVPV       1255
```

SEQ ID NO: 3
Accession No.: NM_001289936
CDS: 583 . . . 4305
```
  1 aagttcctgt gttcttttatt ctactctccg ctgaagtcca cacagtttaa attaaagttc
 61 ccggattttt gtgggcgcct gccccgcccc tcgtccccct gctgtgtcca tatatcgagg
121 cgatagggtt aagggaaggc ggacgcctga tgggttaatg agcaaactga agtgttttcc
181 atgatctttt ttgagtcgca attgaagtac cacctcccga gggtgattgc ttccccatgc
241 gggtagaac ctttgctgtc ctgttcacca ctctacctcc agcacagaat ttggcttatg
301 cctactcaat gtgaagatga tgaggatgaa aacctttgtg atgatccact tccacttaat
```

TABLE A-continued

```
 361 gaatggtggc aaagcaaagc tatattcaag accacatgca aagctactcc ctgagcaaag
 421 agtcacagat aaaacggggg caccagtaga atggccagga caaacgcagt gcagcacaga
 481 gactcagacc ctggcagcca tgcctgcgca ggcagtgatg agagtgacat gtactgttgt
 541 ggacatgcac aaaagtgaga tacttcaaag attccagaag atatgccccg ggggtcctgg
 601 aagccacaag tgtgcaccgg cacagacatg aagctgcggc tccctgccag tcccgagacc
 661 cacctggaca tgctccgcca cctctaccag ggctgccagg tggtgcaggg aaacctggaa
 721 ctcacctacc tgcccaccaa tgccagcctg tccttcctgc aggatatcca ggaggtgcag
 781 ggctacgtgc tcatcgctca caaccaagtg aggcaggtcc cactgcagag gctgcggatt
 841 gtgcgaggca cccagctctt tgaggacaac tatgccctgg ccgtgctaga caatgcagac
 901 ccgctgaaca ataccacccc tgtcacaggg gcctcccag gaggcctgcg ggagctgcag
 961 cttcgaagcc tcacagagat cttgaaagga ggggtcttga tccagcggaa ccccccagctc
1021 tgctaccagg acacgatttt gtggaaggac atcttccaca agaacaacca gctggctctc
1081 acactgatag acaccaaccg ctctcgggcc tgccacccct gttctccgat gtgtaagggc
1141 tcccgctgct ggggagagag ttctgaggat tgtcagagcc tgacgcgcac tgtctgtgcc
1201 ggtggctgtg cccgctgcaa ggggccactg cccactgact gctgccatga gcagtgtgct
1261 gccggctgca cgggccccaa gcactctgac tgcctggcct gcctccactt caaccacagt
1321 ggcatctgtg agctgcactg cccagccctg gtcacctaca acacagacac gtttgagtcc
1381 atgcccaatc ccgagggccg gtatacattc ggcgccagct gtgtgactgc ctgtccctac
1441 aactacccttt ctacggacgt gggatcctgc accctgtctc gcccctgca caaccaagag
1501 gtgacagcag aggatggaac acagcggtgt gagaagtgca gcaagccctg tgcccgagtg
1561 tgctatggtc tgggcatgga gcacttgcga gaggtgaggg cagttaccag tgccaatatc
1621 caggagtttg ctgctgcaa gaagatcttt gggagcctgg catttctgcc ggagagcttt
1681 gatggggacc cagcctccaa cactgccccg ctccagccag agcagctcca agtgtttgag
1741 actctgaag agatcacagg ttacctatac atctcagcat ggccggacag cctgcctgac
1801 ctcagcgtct tccagaacct gcaagtaatc cggggacgga ttctgcacaa tggcgcctac
1861 tcgctgaccc tgcaagggct gggcatcagc tggctggggc tgcgctcact gagggaactg
1921 ggcagtggac tggccctcat ccaccataac acccacctct gcttcgtgca cacggtgccc
1981 tgggaccagc tctttcggaa cccgcaccaa gctctgctcc acactgccaa ccggccagag
2041 gacgagtgtg tgggcgaggg cctggcctgc caccagctgt gcgcccgagg gcactgctgg
2101 ggtccagggc ccacccagtg tgtcaactgc agccagttcc ttcggggcca ggagtgcgtg
2161 gaggaatgcc gagtactgca ggggctcccc agggagtatg tgaatgccag cgactgtttg
2221 ccgtgccacc ctgagtgtca gccccagaat ggctcagtga cctgttttgg accggaggct
2281 gaccagtgtg tggcctgtgc ccactataag gaccctccct tctgcgtggc ccgctgcccc
2341 agcggtgtga aacctgacct ctcctacatg cccatctgga agtttccaga tgaggagggc
2401 gcatgccagc cttgcccccat caactgcacc cactcctgtg tggacctgga tgacaagggc
2461 tgccccgccg agcagagagc cagccctctg acgtccatca tctctgcggt ggttggcatt
2521 ctgctggtcg tggtcttggg ggtggtcttt gggatcctca tcaagcgacg gcagcagaag
2581 atccggaagt acacgatgcg gagactgctg caggaaacgg agctggtgga gccgctgaca
2641 cctagcggag cgatgcccaa ccaggcgcag atgcggatcc tgaaagagac ggagctgagg
2701 aaggtgaagg tgcttggatc tggcgctttt ggcacagtct acaagggcat ctggatccct
2761 gatggggaga atgtgaaaat tccagtggcc atcaaagtgt tgagggaaaa cacatccccc
2821 aaagccaaca aagaaatctt agacgaagca tacgtgatgc ctggtgtggg ctccccatat
2881 gtctcccgcc ttctgggcat ctgcctgaca tccacggtgc agctggtgac acagcttatg
2941 ccctatggct gcctcttaga ccatgtccgg gaaaaccgcg gacgcctggg ctcccaggac
3001 ctgctgaact ggtgtatgca gattgccaag gggatgagct acctggagga tgtgcggctc
3061 gtacacaggg acttggccgc tcggaacgtg ctggtcaaga gtcccaacca tgtcaaaatt
3121 acagacttcg ggctggctcg gctgctggac attgacgaga cagagtacca tgcagatggg
3181 ggcaaggtgc ccatcaagtg gatggcgctg gagtccattc tccgccggcg gttcacccac
3241 cagagtgatg tgtggagtta tggtgtgact gtgtgggagc tgatgacttt tggggccaaa
3301 ccttacgatg ggatcccagc ccgggagatc cctgacctgc tggaaaaggg ggagcggctg
3361 ccccagcccc ccatctgcac cattgatgtc tacatgatca tggtcaaatg ttggatgatt
3421 gactctgaat gtcggccaag attccggag ttggtgtctg aattctcccg catggccagg
3481 gaccccccagc gctttgtggt catccagaat gaggacttgg gcccagccag tcccttggac
3541 agcaccttct accgctcact gctggaggac gatgacatgg gggacctggt ggatgctgag
3601 gagtatctgg tacccccagca gggcttcttc tgtccagacc ctgccccggg cgctggggc
3661 atggtccacc acaggcaccg cagctcatct accaggagtg gcggtgggga cctgacacta
3721 gggctggagc cctctgaaga ggaggccccc aggtctccac tggcacccct cgaagggggct
3781 ggctccgatg tatttgatgg tgacctggga atgggggcag ccaagggggct gcaaagcctc
3841 cccacacatg acccccagcc tctacagcgg tacagtgagg accccacagt accctgccc
3901 tctgagactg atggctacgt tgcccccctg acctgcagcc cccagcctga atatgtgaac
3961 cagccagatg ttcggcccca gccccttcg ccccgagagg gccctctgcc tgctgcccga
4021 cctgctggtg ccactctgga aaggcccaag actctctccc cagggaagaa tgggggtgtc
4081 aaagacgttt ttgccttttgg gggtgccgtg gagaacccc g agtacttgac acccccaggga
4141 ggagctgccc ctcagcccca ccctcctcct gccttcagcc cagccttcga caacctctat
4201 tactgggacc aggacccacc agagcggggg gctccaccca gcaccttcaa agggacacct
4261 acggcagaga acccagagta cctgggtctg acgtgccag tgtgaaccag aaggccaagt
4321 ccgcagaagc cctgatgtgt cctcaggag cagggaaggc ctgacttctg ctggcatcaa
4381 gaggtgggag ggccctccga ccacttcag gggaacctgc catgccagga acctgtccta
4441 aggaaccttc cttcctgctt gagttccag atggctggaa ggggtccagc ctgcttggaa
4501 gaggaacagc actggggagt cttttgtggat tctgaggccc tgcccaatga gactctaggg
4561 tccagtggat gccacagccc agcttggccc tttccttcca gatcctgggt actgaaagcc
4621 ttagggaagc tggcctgaga ggggaagcgg ccctaaggga gtgtctaaga acaaaagcga
4681 cccattcaga gactgtccc gaaacctagt actgccccc atgaggaagg aacagcaatg
4741 gtgtcagtat ccaggctttg tacagagtgc ttttctgttt agttttttact ttttttgttt
4801 tgttttttta aagatgaaat aaagaccccag ggggagaatg ggtgttgtat ggggaggcaa
4861 gtgtgggggg tccttctcca cacccacttt gtccatttgc aaatatattt tggaaaacag
4921 ctaaaaaaaa aaaaaaaaa
```

TABLE A-continued

```
SEQ ID NO: 4
Accession No.: NM_001289936
MPRGSWKPQV CTGTDMKLRL PASPETHLDM LRHLYQGCQV VQGNLELTYL PTNASLSFLQ    60
DIQEVQGYVL IAHNQVRQVP LQRLRIVRGT QLFEDNYALA VLDNGDPLNN TTPVTGASPG   120
GLRELQLRSL TEILKGGVLI QRNPQLCYQD TILWKDIFHK NNQLALTLID TNRSRACHPC   180
SPMCKGSRCW GESSEDCQSL TRTVCAGGCA RCKGPLPTDC CHEQCAAGCT GPKHSDCLAC   240
LHFNHSGICE LHCPALVTYN TDTFESMPNP EGRYTFGASC VTACPYNYLS TDVGSCTLVC   300
PLHNQEVTAE DGTQRCEKCS KPCARVCYGL GMEHLREVRA VTSANIQEFA GCKKIFGSLA   360
FLPESFDGDP ASNTAPLQPE QLQVFETLEE ITGYLYISAW PDSLPDLSVF QNLQVIRGRI   420
LHNGAYSLTL QGLGISWLGL RSLRELGSGL ALIHHNTHLC FVHTVPWDQL FRNPHQALLH   480
TANRPEDECV GEGLACHQLC ARGHCWGPGP TQCVNCSQFL RGQECVEECR VLQGLPREYV   540
NARHCLPCHP ECQPQNGSVT CFGPEADQCV ACAHYKDPPF CVARCPSGVK PDLSYMPIWK   600
FPDEEGACQP CPINCTHSCV DLDDKGCPAE QRASPLTSII SAVVGILLVV VLGVVFGILI   660
KRRQQKIRKY TMRRLLQETE LVEPLTPSGA MPNQAQMRIL KETELRKVKV LGSSGAFGTVY  720
KGIWIPDGEN VKIPVAIKVL RENTSPKANK EILDEAYVMA CVGSPYVSRL LGICLTSTVQ   780
LVTQLMPYGC LLDHVRENRG RLGSQDLLNW CMQIAKGMSY LEDVRLVHRD LAARNVLVKS   840
PNHVKITDFG LARLLDIDET EYHADGGKVP IKWMALESIL RRRFTHQSDV WSYGVTVWEL   900
MTFGAKPYDG IPARETPDLL EKGERLPQPP ICTIDVYMIM VKCWMIDSEC RPRFRELVSE   960
FSRMARDPQR FVVIQNEDLG PASPLDSTFY RSLLEDDDMG DLVDAEEYLV PQQGFFCPDP  1020
APGAGGMVHH RHRSSSTRSG GGDLTLGLEP SEEEAPRSPL APSEGAGSDV FDGDLGMGAA  1080
KGLQSLPTHD PSPLQRYSED PTVPLPSETD GYVAPLTCSP QPEYVNQPDV RPQPPSPREG  1140
PLPAARPAGA TLERPKTLSP GKNGVVKDVF AFGGAVENPE YLTPQGGAAP QPHPPPAFSP  1200
AFDNLYYWDQ DPPERGAPPS TFKGTPTAEN PEYLGLDVPV                        1240

SEQ ID NO: 5
Accession No.: NM_001005862
CDS: 577 . . . 4254
   1 aagttcctgt gttctttatt ctactctccg ctgaagtcca cacagtttaa attaaagttc
  61 ccggattttt gtgggcgcct gccccgcccc tcgtcccccg gctgtgtcca tatatcgagg
 121 cgatagggtt aagggaaggc ggacgcctga tgggttaatg agcaaactga agtgttttcc
 181 atgatctttt ttgagtcgca attgaagtac cacctcccga gggtgattgc ttccccatgc
 241 ggggtagaac ctttgctgtc ctgttcacca ctctacctcc agcacagaat ttggcttatg
 301 cctactcaat gtgaagatga tgaggatgaa aacctttgtg atgatccact tccacttaat
 361 gaatggtggc aaagcaaagc tatattcaag accacatgca aagctactcc ctgagcaaag
 421 agtcacagat aaaacggggg caccagtaga atgccaggac aaacgcagt gcagcacaga
 481 gactcagacc ctggcagcca tgcctgcgca ggcagtgatg agagtgacat gtactgttgt
 541 ggacatgcac aaaagtgagt gtgcaccggc acagacatga agctgcggct ccctgccagt
 601 cccgagaccc acctggacat gctccgccac ctctaccagg gctgccaggt ggtgcaggga
 661 aacctggaac tcacctacct gcccaccaat gccagcctgt ccttcctgca ggatatccag
 721 gaggtgcagg gctacgtgct catcgctcac aaccaagtga ggcaggtccc actgcagagg
 781 ctgcggattg tgcgaggcac ccagctcttt gaggacaact atgccctggc cgtgctagac
 841 aatggagacc cgctgaacaa taccaccct gtcacagggg cctcccagg aggcctgcgg
 901 gagctgcagc ttcgaagcct cacagagatc ttgaaggag gggtcttgat ccagcggaac
 961 ccccagctct gctaccagga cacgattttg tggaaggaca tcttccacaa gaacaaccag
1021 ctggctctca cactgataga caccaaccgc tctcgggcct gccaccctg ttctccgatg
1081 tgtaagggct cccgctgctg gggagagagt tctgaggatt gtcagagcct gacgcgcact
1141 gtctgtgccg gtggctgtgc ccgctgcaag gggccactgc ccactgactg ctgccatgag
1201 cagtgtgctg ccggctgcac gggccccaag cactctgact gcctggcctg cctccacttc
1261 aaccacagtg gcatctgtga gctgcactgc ccagccctgg tcacctacaa cacagacacg
1321 tttgagtcca tgcccaatcc cgagggccgg tatacattcg gcgccagctg tgtgactgcc
1381 tgtcccctaca actaccttc tacggacgtg ggatcctgca ccctcgtctg cccctgcac
1441 aaccaagagt gcagcagca ggatggaaca cagcggtgtg agaagtgcag caagccctgt
1501 gcccgagtgt gctatggtct gggcatggag cacttgcgag aggtgagggc agttaccagt
1561 gccaatatcc aggagtttgc tggctgcaag aagatctttg ggagcctggc atttctgccg
1621 gagagctttg atggggaccc agcctccaac actgccccgc tccagccaga gcagctccaa
1681 gtgtttgaga ctctggaaga gatcacaggt tacctataca tctcagcatg gccggacagc
1741 ctgcctgacc tcagcgtctt ccagaacctg caagtaatcc ggggacgaat tctgcacaat
1801 ggcgcctact cgctgaccct gcaagggctg ggcatcagct ggctgggct cgctcactg
1861 agggaactgg gcagtggact ggccctcatc caccataaca cccaccctg cttcgtgcac
1921 acggtgccct gggaccagct cttcggaac ccgcaccaag ctctgctcca cactgccaac
1981 cggcagagg acgagtgtgt gggcgagggc ctggcctgcc accagctgtg cgcccgaggg
2041 cactgctggg gtccagggcc cacccagtgt gtcaactgca gccagttcct tcggggccag
2101 gagtgcgtgg aggaatgccg agtactgcag gggctcccca gggagtatgt gaatgccagg
2161 cactgtttgc cgtgccaccc tgagtgtcag cccagaatg gctcagtgac ctgttttgga
2221 ccggaggctg accagtgtgt ggcctgtgcc cactataagg accctccctt ctgcgtggcc
2281 cgctgcccca gcgtgtgaa acctgacctc tcctacatgc ccatctggaa gtttccagat
2341 gaggagggcg catgccagcc ttgccccatc aactgcaccc actcctgtgt ggacctggat
2401 gacaagggct gccccgccga gcagagagcc agccctctga cgtccatcat ctctgcggtg
2461 gttggcattc tgctggtcgt ggtcttgggg gtggtctttg gatcctcat caagcgacgg
2521 cagcagaaga tccggaagta cacgatgcgg agactgctgc aggaaacgga gctggtggag
2581 ccgctgacac tagccggag gatgcccaac caggcgcaga tgcggatcct gaaagagacg
2641 gagctgagga aggtgaaggt gcttggatct ggcgcttttg gcacagtcta caaggcatc
2701 tggatccctg atggggagaa tgtgaaaatt ccagtggcca tcaaagtgtt gagggaaaac
2761 acatccccca aagccaacaa agaaatctta gacgaagcat acgtgatggc tggtgtgggc
2821 tccccatatg tctcccgcct tctgggcatc tgcctgacat ccacggtgca gctggtgaca
2881 cagcttatgc cctatggctg cctcttagac catgtcccgg aaaaccgcgg acgcctggga
2941 tcccaggacc tgctgaactg gtgtatgcag attgccaagg gatgagcta cctggaggat
3001 gtgcggctcg tacacaggga cttggccgct cggaacgtgc tggtcaagag tcccaaccat
3061 gtcaaaatta cagacttcgg gctggctcgg ctgctggaca ttgacgagac agtaccat
3121 gcagatgggg gcaaggtgcc catcaagtgg atggcgctga gtccattct ccgccggcgg
```

TABLE A-continued

```
3181 ttcacccacc agagtgatgt gtggagttat ggtgtgactg tgtgggagct gatgactttt
3241 ggggccaaac cttacgatgg gatcccagcc cgggagatcc ctgacctgct ggaaaagggg
3301 gagcggctgc cccagccccc catctgcacc attgatgtct acatgatcat ggtcaaatgt
3361 tggatgattg actctgaatg tcggccaaga ttccggagt tggtgtctga attctcccgc
3421 atggccaggg accccagcg ctttgtggtc atccagaatg aggacttggg cccagccagt
3481 cccttggaca gcaccttcta ccgctcactg ctggaggacg atgacatggg ggacctggtg
3541 gatgctgagg agtatctggt accccagcag ggcttcttct gtccagaccc tgccccgggc
3601 gctggggca tggtccacca caggcaccgc agctcatcta ccaggagtgg cggtggggac
3661 ctgacactag ggctggagcc ctctgaagag gaggccccca ggtctccact ggcaccctcc
3721 gaaggggctg gctccgatgt atttgatggt gacctgggaa tggggcagc caaggggctg
3781 caaagcctcc ccacacatga ccccagccct ctacagcgt acagtgagga ccccacagta
3841 cccctgccct ctgagactga tggctacgtt gccccctga cctgcagccc ccagcctgaa
3901 tatgtgaacc agccagatgt tcggcccag ccccctcgc cccgagaggg ccctctgcct
3961 gctgcccgac ctgctggtgc cactctgaa aggcccaaga ctctctcccc agggaagaat
4021 ggggtcgtca agacgtttt tgcctttggg ggtgccgtgg agaacccga gtacttgaca
4081 ccccaggag gagctgcccc tcagccccac cctcctcctg ccttcagccc agccttcgac
4141 aacctctatt actgggacca ggaccccaca gagcggggg ctccacccag caccttcaaa
4201 gggacaccta cggcagagaa cccagagtac ctgggtctgg acgtgccagt gtgaaccaga
4261 aggccaagtc cgcagaagcc ctgatgtgtc tcagggagc agggaaggcc tgacttctgc
4321 tggcatcaag aggtgggagg gccctccgac cacttccagg ggaacctgcc atgccaggaa
4381 cctgtcctaa ggaaccttcc ttcctgcttg agttcccaga tggctggaag gggtccagcc
4441 tcgttggaag aggaacagca ctggggagtc tttgtggatt ctgaggccct gcccaatgag
4501 actctagggt ccagtggatg ccacagccca gcttggccct ttccttccag atcctgggta
4561 ctgaaagcct tagggaagct ggcctgagag ggaagcggc cctaagggag tgtctaagaa
4621 caaaagcgac ccattcagag actgtccctg aaacctagta ctgcccccca tgaggaagga
4681 acagcaatgg tgtcagtatc caggctttgt acagagtgct tttctgttta gttttactt
4741 ttttgtttt gtttttaa agatgaaata aagacccagg gggagaatgg gtgttgtatg
4801 gggaggcaag tgtgggggt ccttctccac acccactttg tccatttgca aatatatttt
4861 ggaaacagc taaaaaaaaa aaaaaaaaa
```

SEQ ID NO: 6
Accession No.: NM_ 01005862

```
MKLRLPASPE THLDMLRHLY QGCQVVQGNL ELTYLPTNAS LSFLQDIQEV QGYVLIAHNQ   60
VRQVPLQRLR IVRGTQLFED NYALAVLDNG DPLNNTTPVT GASPGGLREL QLRSLTEILK  120
GGVLIQRNPQ LCYQDTILWK DIFHKNNQLA LTLIDTNRSR ACHPCSPMCK GSRCWGESSE  180
DCQSLTRTVC AGGCARCKGP LPTDCCHEQC AAGCTGPKHS DCLACLHFNH SGICELHCPA  240
LVTYNTDTFE SMPNPEGRYT FGASCVTACP YNYLSTDVGS CTLVCPLHNQ EVTAEDGTQR  300
CEKCSKPCAR VCYGLGMEHL REVRAVTSAN IQEFAGCKKI FGSLAFLPES FDGDPASNTA  360
PLQPEQLVF ETLEEITGYL YISAWPDSLP DLSVFQNLQV IRGRILHNGA YSLTLQGLGI  420
SWLGLRSLRE LGSGLALIHH NTHLCFVHTV PWDQLFRNPH QALLHTANRP EDECVGEGLA  480
CHQLCARGHC WGPGPTQCVN CSQFLRGQEC VEECRVLQGL PREYVNARHC LPCHPECQPQ  540
NGSVTCFGPE ADQCVACAHY KDPPFCVARC PSGVKPDLSY MPIWKFPDEE GACQPCPINC  600
THSCVDLDDK GCPAEQRASP LTSIISAVVG ILLVVVLGVV FGILIKRRQQ KIRKYTMRRL  660
LQETELVEPL TPSGAMPNQA QMRILKETEL RKVKVLGSGA FGTVYKGIWI PDGENVKIPV  720
AIKVLRENTS PKANKEILDE AYVMAGVGSP YVSRLLGICL TSTVQLVTQL MPYGCLLDHV  780
RENRGRLGSQ DLLNWCMQIA KGMSYLEDVR LVHRDLAARN VLVKSPNHVK ITDFGLARLL  840
DIDETEYHAD GGKVPIKWMA LESILRRRFT HQSDVWSYGV TVWELMTFGA KPYDGIPARE  900
IPDLLEKGER LPQPPICTID VYMIMVKCWM IDSECRPRFR ELVSEFSRMA RDPQRFVVIQ  960
NEDLGPASPL DSTFYRSLLE DDDMGDLVDA EEYLVPQQGF FCPDPAPGAG GMVHHRHRSS 1020
STRSGGGDLT LGLEPSEEEA PRSPLAPSEG AGSDVFDGDL GMGAAKGLQS LPTHDPSPLQ 1080
RYSEDPTVPL PSETDGYVAP LTCSPQPEYV NQPDVRPQPP SPREGPLPAA RPAGATLERP 1140
KTLSPGKNGV VKDVFAFGGA VENPEYLTPQ GGAAPQPHPP PAFSPAFDNL YYWDQDPPER 1200
GAPPSTFKGT PTAENPEYLG LDVPV                                      1255
```

SEQ ID NO: 7 Mutant HER2 (having the amino acid sequence set forth
in SEQ ID NO: 2 as a base and comprising the mutation
A775_G776insYVMA (HER2ex20insYVMA))

```
MELAALCRWG LLLALLPPGA ASTQVCTGTD MKLRLPASPE THLDMLRHLY QGCQVVQGNL   60
ELTYLPTNAS LSFLQDIQEV QGYVLIAHNQ VRQVPLQRLR IVRGTQLFED NYALAVLDNG  120
DPLNNTTPVT GASPGGLREL QLRSLTEILK GGVLIQRNPQ LCYQDTILWK DIFHKNNQLA  180
LTLIDTNRSR ACHPCSPMCK GSRCWGESSE DCQSLTRTVC AGGCARCKGP LPTDCCHEQC  240
AAGCTGPKHS DCLACLHFNH SGICELHCPA LVTYNTDTFE SMPNPEGRYT FGASCVTACP  300
YNYLSTDVGS CTLVCPLHNQ EVTAEDGTQR CEKCSKPCAR VCYGLGMEHL REVRAVTSAN  360
IQEFAGCKKI FGSLAFLPES FDGDPASNTA PLQPEQLVF ETLEEITGYL YISAWPDSLP  420
DLSVFQNLQV IRGRILHNGA YSLTLQGLGI SWLGLRSLRE LGSGLALIHH NTHLCFVHTV  480
PWDQLFRNPH QALLHTANRP EDECVGEGLA CHQLCARGHC WGPGPTQCVN CSQFLRGQEC  540
VEECRVLQGL PREYVNARHC LPCHPECQPQ NGSVTCFGPE ADQCVACAHY KDPPFCVARC  600
PSGVKPDLSY MPIWKFPDEE GACQPCPINC THSCVDLDDK GCPAEQRASP LTSIISAVVG  660
ILLVVVLGVV FGILIKRRQQ KIRKYTMRRL LQETELVEPL TPSGAMPNQA QMRILKETEL  720
RKVKVLGSGA FGTVYKGIWI PDGENVKIPV AIKVLRENTS PKANKEILDE AYVMAYVMAG  780
VGSPYVSRLL GICLTSTVQL VTQLMPYGCL LDHVRENRGR LGSQDLLNWC MQIAKGMSYL  840
EDVRLVHRDL AARNVLVKSP NHVKITDFGL ARLLDIDETE YHADGGKVPI KWMALESILR  900
RRFTHQSDVW SYGVTVWELM TFGAKPYDGI PAREIPDLLE KGERLPQPPI CTIDVYMIMV  960
KCWMIDSECR PRFRELVSEF SRMARDPQRF VVIQNEDLGP ASPLDSTFYR SLLEDDDMGD 1020
LVDAEEYLVP QQGFFCPDPA PGAGGMVHHR HRSSSTRSGG GDLTLGLEPS EEEAPRSPLA 1080
PSEGAGSDVF DGDLGMGAAK GLQSLPTHDP SPLQRYSEDP TVPLPSETDG YVAPLTCSPQ 1140
PEYVNQPDVR PQPPSPREGP LPAARPAGAT LERPKTLSPG KNGVVKDVFA FGGAVENPEY 1200
LTPQGGAAPQ PHPPPAFSPA FDNLYYWDQD PPERGAPPST FKGTPTAENP EYLGLDVPV  1259
```

In the present description, the term "effective amount" used regarding the compound of the present invention means the amount of the compound of the present invention that induces the biological or medical response of a subject, such as, for example, reduction or inhibition of enzyme or protein activity; or ameliorates symptoms, alleviates conditions, and retards or delays the progression of disease; or prevents disease; etc. (therapeutically effective amount).

In the present description, the term "subject" includes mammals and non-mammals. Examples of the mammal may include, but are not limited to, a human, a chimpanzee, an ape, a monkey, a bovine, a horse, sheep, a goat, a swine, a rabbit, a dog, a cat, a rat, a mouse, a Guinea pig, a hedgehog, a kangaroo, a mole, a wild pig, a bear, a tiger, and a lion. Examples of the non-mammal may include, but are not limited to, birds, fish, and reptiles. In one embodiment, the subject is a human, and may be a human who has been diagnosed to need the treatment for the symptoms, conditions or disease disclosed in the present description.

Upon the use of the compound of the present invention or a salt thereof as a medicament, a pharmaceutically acceptable carrier is mixed into it, as necessary, and various types of dosage forms can be adopted depending on the preventive or therapeutic purpose. Examples of the dosage form may include all of an oral agent, an injection, a suppository, an ointment, and a patch. Preferably, an oral agent is adopted. These dosage forms can be produced by commonly used production methods that are known to skilled persons.

One embodiment of the present invention provides an antitumor agent for oral administration, comprising the compound of the present invention or a salt thereof as an active ingredient. In addition, one embodiment of the present invention provides a method for preventing and/or treating tumor, comprising administering an effective amount of the compound of the present invention or a salt thereof to a subject in need thereof by oral administration. Moreover, one embodiment of the present invention provides use of the compound of the present invention or a salt thereof for the production of an antitumor agent for oral administration. Furthermore, one embodiment of the present invention provides the compound of the present invention or a salt thereof for use in the prevention and/or treatment of tumor by oral administration thereof.

One embodiment of the present invention provides a pharmaceutical composition comprising the compound of the present invention or a salt thereof. The pharmaceutical composition according to one embodiment of the present invention comprises the compound of the present invention or a salt thereof, and a pharmaceutically acceptable carrier. Further, one embodiment of the present invention provides use of the compound of the present invention or a salt thereof for the production of a pharmaceutical composition. Another embodiment of the present invention provides the compound of the present invention or a salt thereof for use as a medicament.

As pharmaceutically acceptable carriers, various types of organic or inorganic carrier substances, which are commonly used as preparation materials, are used. When the compound of the present invention is processed into a solid preparation, examples of the pharmaceutically acceptable carrier mixed into the compound of the present invention may include an excipient, a binder, a disintegrator, a lubricant, a coating agent, and a coloring agent. When the compound of the present invention is processed into a liquid preparation, examples of the pharmaceutically acceptable carrier mixed into the compound of the present invention may include a solvent, a solubilizer, a suspending agent, a tonicity agent, a buffer, and a soothing agent. In addition, preparation additives such as an antiseptic, an antioxidant, a sweetener, and a stabilizer can also be used, as necessary.

In the case of preparing a solid preparation for oral administration, an excipient, and as necessary, a binder, a disintegrator, a lubricant, a coloring agent, a corrigent, etc. are added to the compound of the present invention, and thereafter, a tablet, a coated tablet, a granule, a powder agent, a capsule, etc. can be produced according to ordinary methods.

In the case of preparing an injection, a pH adjuster, a buffer, a stabilizer, a tonicity agent, a local anesthetic, etc. are added to the compound of the present invention, and thereafter, subcutaneous, intramuscular, and intravenous injections can be produced according to ordinary methods.

The amount of the compound of the present invention to be mixed into the above-described each dosage unit form depends on the symptoms of a subject to whom the present compound should be applied, the dosage form and the like, and thus, the amount of the compound of the present invention is not constant. In general, it is preferable that the applied dose is set to be 0.05 to 1000 mg per dosage unit form in the case of an oral agent, it is set to be 0.01 to 500 mg per dosage unit form in the case of an injection, and it is set to be 1 to 1000 mg per dosage unit form in the case of a suppository.

The daily dose of a drug having the above-described dosage form is different depending on the symptoms, body weight, age, sex and the like of a subject, and thus, it cannot be generally determined. However, the compound of the present invention may be administered to an adult (body weight: 50 kg) at a daily dose of generally 0.05 to 5000 mg, and preferably 0.1 to 1000 mg.

The tumor that is the target of the present invention is not particularly limited. Examples of the tumor may include brain tumor, head and neck cancer, digestive cancer (esophageal cancer, stomach cancer, duodenal cancer, liver cancer, biliary tract cancer (gallbladder and/or bile duct cancer, etc.), pancreatic cancer, colorectal cancer (colon cancer, rectal cancer, etc.), etc.), lung cancer (non-small cell lung cancer, small cell lung cancer, mesothelioma, etc.), breast cancer, genital cancer (ovarian cancer, uterine cancer (cervical cancer, endometrial cancer, etc.), etc.), urinary organ cancer (kidney cancer, bladder cancer, prostate cancer, testicular tumor, etc.), hematopoietic tumor (leukemia, malignant lymphoma, multiple myeloma, etc.), bone and/or soft tissue tumor, and skin cancer. Among these, preferable is lung cancer, breast cancer, stomach cancer, colorectal cancer, bladder cancer, biliary tract cancer or uterine cancer, and more preferable is lung cancer, breast cancer, stomach cancer, bladder cancer, or biliary tract cancer.

In one embodiment, the tumor is a brain tumor. The compound of the present invention may be useful for the treatment of the symptoms of brain that is required to pass through the blood-brain barrier. The compound of one embodiment has favorable permeability through the blood-brain barrier for the delivery thereof into the brain, namely, excellent brain penetration properties. As an indicator of the penetration properties of the compound into the brain, the concentration of the compound in the brain or a Kp value (brain-to-plasma drug concentration ratio) is applied.

The brain tumor treated with the compound of the present invention includes metastatic brain tumor and primary brain tumor.

Examples of the brain tumor may include, but are not particularly limited to, metastatic brain tumor (e.g., brain metastasis of lung cancer, breast cancer, stomach cancer, colorectal cancer, bladder cancer, biliary tract cancer, uterine cancer, etc. (preferably, lung cancer, breast cancer, or stomach cancer)), piliocytic astrocytoma, diffuse astrocytoma, oligodendroma and/or oligodendroastrocytoma, anaplastic astrocytoma and/or anaplastic oligodendroglioma, anaplastic oligodendroastrocytoma, glioblastoma, ependymoma, anaplastic ependymoma, ganglioglioma, central neurocytoma, medulloblastoma, germinoma, central nervous system malignant lymphoma, meningioma, neurilemmoma, GH secreting pituitary adenoma, PRL-secreting pituitary adenoma, ACTH-secreting pituitary adenoma, nonfunctional pituitary adenoma, craniopharyngioma, chordoma, hemangioblastoma, and epidermoid tumor.

EXAMPLES

Hereinafter, the present invention will be described in detail in the following examples. However, these examples are not intended to limit the scope of the present invention.

In the present description, "room temperature" generally means a temperature that is from approximately 10° C. to approximately 35° C. In addition, in the following Examples regarding compounds, "%" indicates weight percent, unless otherwise specified.

Various types of reagents used in the Examples were commercially available products, unless otherwise specified. Silica gel chromatography was carried out using Biotage SNAP Cartridge Ultra, manufactured by Biotage Japan Ltd. Basic silica gel chromatography was carried out using Biotage SNAP Cartridge Isolute Flash-NH2, manufactured by Biotage Japan Ltd.

Preparative thin-layer chromatography was carried out using Kieselgel TM60F254, Art. 5744, manufactured by Merck, or NH2 Silica Gel 60F254 Plate-Wako, manufactured by Wako Pure Chemical Industries, Ltd.

$^1$H-NMR was measured using tetramethylsilane as a reference material, and employing AL400 (400 MHz) manufactured by JEOL, Mercury (400 MHz) manufactured by Varian, or Inova (400 MHz) manufactured by Varian. Moreover, mass spectrum was measured using Micromass ZQ or SQD manufactured by Waters, according to electrospray ionization (ESI) or atmospheric pressure chemical ionization (APCI). Microwave reaction was carried out using Initiator manufactured by Biotage Japan Ltd.

Abbreviations have the following meanings.
s: Singlet
d: Doublet
t: Triplet
q: Quartet
dd: Double doublet
dt: Double triplet
td: Triple doublet
tt: Triple triplet
ddd: Double double doublet
ddt: Double double triplet
dtd: Double triple doublet
tdd: Triple double doublet
m: Multiplet
br: Broad
ATP: Adenosine triphosphate
DMSO-d6: Deuterated dimethyl sulfoxide
CDCl$_3$: Deuterated chloroform
EDTA: Ethylenediaminetetraacetic acid
THF: Tetrahydrofuran
DMF: N,N-dimethylformamide
DMSO: Dimethyl sulfoxide
NMP: N-methyl pyrrolidone HATU: O-(7-azabenzotriazol-1-yl)-N,N,N',N'-tetramethyluronium hexafluorophosphate
HPMC: Hypromellose
PdCl$_2$(PPh$_3$)$_2$: Dichlorobis(triphenylphosphine)palladium (II)

Reference Example 1

Reference Example 1(1)

tert-Butyl (2S,4R)-4-(4-amino-5-iodo-7H-pyrrolo[2,3-d]pyrimidin-7-yl)-2-methylpyrrolidine-1-carboxylate tert-Butyl (2S,4S)-4-hydroxy-2-methylpyrrolidine-1-carboxylate (19.0 g) and 4-chloro-5-iodo-7H-pyrrolo[2,3-d]pyrimidine (13.1 g) were dissolved in THF (190 mL), and the obtained solution was then cooled to 0° C. Thereafter, triphenylphosphine (37.2 g) and diisopropyl azodicarboxylate (28.1 mL) were added to the reaction solution, and the temperature of the mixture was then increased to room temperature, followed by stirring for 1 hour. Thereafter, the reaction mixture was concentrated under reduced pressure, and the obtained residue was then purified by silica gel chromatography (hexane:ethyl acetate) to obtain the corresponding coupling body. The obtained compound was used in the subsequent reaction without being further purified.

The obtained coupling body, THF (114 mL) and ammonia water (114 mL) were added into a pressure resistant tube, and the obtained mixture was then stirred at 100° C. for 14 hours. Thereafter, the reaction mixture was cooled to room temperature, and was then poured into water (285 mL). The thus obtained mixture was stirred at room temperature for 5 hours. Thereafter, the precipitated solid was collected by filtration, was then washed with water, and was then dried to obtain a product of interest (34.5 g).

$^1$HNMR (CDCl$_3$) δ: 8.27 (s, 1H) 7.15 (s, 1H) 5.55-5.73 (m, 2H) 5.12-5.25 (m, 1H) 3.86-4.18 (m, 2H) 3.43-3.57 (m, 1H) 2.59-2.69 (m, 1H) 1.92-2.03 (m, 1H) 1.48 (s, 9H) 1.30-1.40 (m, 3H)

ESI-MS m/z 444 (MH+)

Reference Example 1(2)

4-Amino-7-((3R,5S)-1-(tert-butoxycarbonyl)-5-methylpyrrolidin-3-yl)-7H-pyrrolo[2,3-d]pyrimidine-5-carboxylic Acid The compound of Reference Example 1(1) (28.0 g), 10% palladium carbon catalyst (720 mg), NMP (84 mL), methanol (26 mL), and triethylamine (17.6 mL) were added into a pressure resistant tube, followed by carbon monoxide substitution, and the obtained mixture was stirred at 100° C. for 2 hours. Thereafter, the reaction mixture was cooled to room temperature, a 2 M sodium hydroxide aqueous solution (79 mL) was then added thereto, and the obtained mixture was then stirred at 80° C. for 2 hours. Thereafter, the reaction mixture was cooled to room temperature, was then filtrated through Celite, and was then washed with methanol. Subsequently, methanol in the filtrate was concentrated under reduced pressure. Water was further added, and the water layer was then washed with tert-butyl methyl ether. A 1 M potassium hydrogen sulfate aqueous solution was added to the water layer to adjust the pH to approximately 3. The precipitated solid was collected by filtration, was then washed with water, and was then dried to obtain a product of interest (23.4 g).

¹HNMR (400 MHz, DMSO-d6) δ: 8.14 (s, 1H) 8.08 (s, 1H) 5.16-4.93 (m, 1H) 4.07-3.79 (m, 2H) 3.61-3.45 (m, 1H) 2.53 (m, 1H) 2.33-2.02 (m, 1H) 1.42 (s, 9H) 1.29 (d, J=6.1 Hz, 3H) ESI-MS m/z 362 (MH+)

EXAMPLES

Example 1(1)

tert-Butyl-4-amino-6-bromo-7-((3R,5S)-1-(tert-butoxycarbonyl)-5-methylpyrrolidin-3-yl)-7H-pyrrolo[2,3-d]pyrimidine-5-carboxylate Under a nitrogen atmosphere, the compound of Reference Example 1(2) (15.0 g) was dissolved in chloroform (150 mL), and 2-tert-butyl-1,3-diisopropylisourea (25 mL) was then added to the above obtained solution. The temperature of the obtained mixture was increased to 60° C., and the mixture was then stirred for 2 hours. Thereafter, 2-tert-butyl-1,3-diisopropylisourea (25 mL) was further added to the reaction mixture, and the thus obtained mixture was then stirred for 2 hours. Thereafter, the reaction mixture was cooled to room temperature, and was then concentrated under reduced pressure. To the obtained residue, tert-butyl methyl ether was added, and the precipitated solid was collected by filtration and was then washed with tert-butyl methyl ether. The filtrate was concentrated under reduced pressure, and tert-butyl methyl ether was then added to the obtained residue. The precipitated solid was collected by filtration, and was then washed with tert-butyl methyl ether. The obtained residue was purified by silica gel chromatography (hexane:ethyl acetate) to obtain a tert-butyl ester form. The obtained compound was used in the subsequent halogenation reaction without being further purified.

The obtained tert-butyl ester form was dissolved in chloroform (140 mL), and N-bromosuccinimide (11.8 g) was then added to the above obtained solution. The obtained mixture was stirred at room temperature for 24 hours. Thereafter, to the reaction mixture, chloroform and 10% sodium bisulfite aqueous solution were successively added, and the obtained mixture was then extracted with chloroform. The gathered organic layer was washed with saturated saline, was then dried over anhydrous sodium sulfate, and was then concentrated under reduced pressure. The obtained residue was purified by silica gel chromatography (hexane: ethyl acetate) to obtain a product of interest (13.8 g).

¹HNMR (CDCl₃) δ: 8.02 (s, 1H) 5.74-5.13 (m, 2H) 4.07-3.64 (m, 2H) 2.43-2.29 (m, 1H) 2.07-1.97 (m, 1H) 1.63 (s, 9H) 1.48 (m, 12H)
ESI-MS m/z 496,498 (MH+)

Example 1(2)

tert-Butyl-7-((3R,5S)-1-acryloyl-5-methylpyrrolidin-3-yl)-4-amino-6-bromo-7H-pyrrolo[2,3-d]pyrimidine-5-carboxylate The compound of Example 1(1) (11.4 g) was dissolved in THF (57 mL), and the obtained solution was then cooled to 0° C. Thereafter, 4 M hydrogen chloride in 1,4-dioxane solution (114 mL) was added to the mixture, and the thus obtained mixture was then stirred at 0° C. for 10 hours. Subsequently, to the reaction mixture, a 5 M sodium hydroxide aqueous solution (92 mL), acetonitrile (57 mL), diisopropylethylamine (20 mL), and acryloyl chloride (2.0 mL) were added, and the obtained mixture was then stirred for 30 minutes. Thereafter, the reaction mixture was extracted with ethyl acetate, and the gathered organic layer was washed with saturated saline, was then dried over anhydrous sodium sulfate, and was then concentrated under reduced pressure. The obtained residue was purified by silica gel chromatography (hexane:acetone) to obtain a product of interest (7.72 g).

¹HNMR(CDCl₃) δ: 8.26-8.16 (m, 1H) 6.62-6.30 (m, 2H) 5.81-5.64 (m, 1H) 5.33-5.14 (m, 1H) 4.81-3.75 (m, 3H) 3.07-2.86 (m, 1H) 2.67-2.33 (m, 1H) 1.69-1.61 (m, 9H) 1.60-1.51 (m, 3H)
ESI-MS m/z 450,452 (MH+)

Example 1(3)

tert-Butyl-7-((3R,5S)-1-acryloyl-5-methylpyrrolidin-3-yl)-4-amino-6-(prop-1-yn-1-yl)-7H-pyrrolo[2,3-d]pyrimidine-5-carboxylate 1.0 M Propyne in DMF solution (85.7 mL) was added to the compound of Example 1(2) (7.72 g), acetonitrile (154 mL), triethylamine (7.2 mL), PdCl₂(PPh₃)₂ (1.2 g), and copper(I) iodide (330 mg), followed by nitrogen substitution. Thereafter, the mixture was stirred at 70° C. for 4 hours. Thereafter, the reaction mixture was cooled to room temperature, and ethyl acetate and a saturated sodium hydrogen carbonate aqueous solution were added to the mixture. Thereafter, the obtained mixture was extracted with ethyl acetate, and the gathered organic layer was washed with water, and then with saturated saline. The resultant was dried over anhydrous sodium sulfate, and was then concentrated under reduced pressure. The obtained residue was purified by silica gel chromatography (hexane:acetone) to obtain a product of interest (4.06 g).

¹HNMR(CDCl₃) δ: 8.29-8.17 (m, 1H) 6.63-6.30 (m, 2H) 5.81-5.63 (m, 1H) 5.42-5.15 (m, 1H) 4.66-3.81 (m, 3H) 3.01-2.82 (m, 1H) 2.65-2.32 (m, 1H) 2.92-2.13 (m, 3H) 1.65-1.59 (m, 9H) 1.57-1.49 (m, 3H)
ESI-MS m/z 410 (MH+)

Example 1(4)

7-((3R,5S)-1-acryloyl-5-methylpyrrolidin-3-yl)-4-amino-6-(prop-1-yn-1-yl)-7H-pyrrolo[2,3-d]pyrimidine-carboxylic Acid The compound of Example 1(3) (1.52 g) was dissolved in chloroform (5 mL), and trifluoroacetic acid (5 mL) was then added to the above obtained solution. The mixture was stirred at room temperature for 2 hours, and the reaction mixture was then concentrated under reduced pressure. To the residue, chloroform was added, and the obtained mixture was concentrated under reduced pressure again. The residue was dried under reduced pressure to obtain a product of interest (1.25 g).
ESI-MS m/z 354 (MH+)

Example 1(5)

7-(R)-((3R,5S)-1-acryloyl-5-methylpyrrolidin-3-yl)-4-amino-N—((R)-1-(3,5-difluorophenyl)ethyl)-6-(prop-1-yn-1-yl)-7H-pyrrolo[2,3-d]pyrimidine-5-carboxamide To the compound of Example 1(4) (100 mg) in DMF (1.0 mL) solution, (R)-1-(3,5-difluorophenyl)ethan-1-amine (89.0 mg), diisopropylethylamine (0.25 mL), and HATU (215 mg) were added, and the obtained mixture was then stirred at room temperature for 2 hours. Thereafter, to the reaction mixture, a saturated sodium hydrogen carbonate aqueous solution was added, and the obtained mixture was then extracted with ethyl acetate. The gathered organic layer was washed with saturated saline, was then dried over anhydrous sodium sulfate, and was then concentrated under reduced pressure. The obtained residue was purified by silica gel chromatography (hexane:acetone) to obtain the title compound (60 mg).

$^1$HNMR (DMSO-d6) δ: 8.51 (d, J=7.3 Hz, 1H) 8.16 (s, 1H) 7.25-7.07 (m, 3H) 6.74-6.47 (m, 1H) 6.25-6.08 (m, 1H) 5.78-5.58 (m, 1H) 5.41-5.21 (m, 1H) 5.21-5.06 (m, 1H) 4.45-4.29 (m, 1H) 4.24-3.91 (m, 2H) 2.78-2.58 (m, 1H) 2.52-2.41 (m, 1H) 2.23 (s, 3H) 1.48 (d, J=7.1 Hz, 3H) 1.39 (d, J=6.1 Hz, 3H)

ESI-MS m/z 493 (MH+)

Example 2

7-((3R,5S)-1-acryloyl-5-methylpyrrolidin-3-yl)-4-amino-N—((R)-1-phenylethyl)-6-(prop-1-yn-1-yl)-7H-pyrrolo[2,3-d]pyrimidine-5-carboxamide The title compound was obtained in the same manner as that of Example 1, with the exception that (R)-1-phenylethan-1-amine was used instead of (R)-1-(3,5-difluorophenyl)ethan-1-amine in Example 1(5).

$^1$HNMR (DMSO-d6) δ: 8.35 (d, J=7.8 Hz, 1H) 8.17-8.13 (m, 1H) 7.48-7.23 (m, 5H) 6.76-6.46 (m, 1H) 6.28-6.06 (m, 1H) 5.81-5.58 (m, 1H) 5.43-5.02 (m, 2H) 4.42-4.28 (m, 1H) 4.21-3.96 (m, 2H) 2.74-2.59 (m, 1H) 2.54-2.41 (m, 1H) 2.17 (s, 3H) 1.50 (d, J=6.8 Hz, 3H) 1.42-1.33 (m, 3H)

ESI-MS m/z 457 (MH+)

Example 3

7-((3R,5S)-1-acryloyl-5-methylpyrrolidin-3-yl)-4-amino-N-(2-phenylpropan-2-yl)-6-(prop-1-yn-1-yl)-7H-pyrrolo[2,3-d]pyrimidine-5-carboxamide The title compound was obtained in the same manner as that of Example 1, with the exception that 2-phenylpropan-2-amine was used instead of (R)-1-(3,5-difluorophenyl)ethan-1-amine in Example 1(5).

$^1$HNMR (DMSO-d6) δ: 8.26 (s, 1H) 8.16-8.08 (m, 1H) 7.44 (dd, J=8.8, 1.2 Hz, 2H) 7.38-7.28 (m, 2H) 7.21 (tt, J=7.3, 1.27 Hz, 1H) 6.76-6.50 (m, 1H) 6.25-6.10 (m, 1H) 5.79-5.62 (m, 1H) 5.45-5.19 (m, 1H) 4.45-4.30 (m, 1H) 4.26-4.01 (m, 2H) 2.79-2.42 (m, 2H) 2.29-2.22 (m, 3H) 1.71 (s, 6H) 1.43-1.36 (m, 3H)

ESI-MS m/z 471 (MH+)

Example 4

7-((3R,5S)-1-acryloyl-5-methylpyrrolidin-3-yl)-4-amino-N—((R)-1-phenylpropyl)-6-(prop-1-yn-1-yl)-7H-pyrrolo[2,3-d]pyrimidine-5-carboxamide The title compound was obtained in the same manner as that of Example 1, with the exception that (R)-1-phenylpropan-1-amine was used instead of (R)-1-(3,5-difluorophenyl)ethan-1-amine in Example 1(5).

$^1$HNMR (DMSO-d6) δ: 8.35 (brd, J=8.0 Hz, 1H) 8.17-8.11 (m, 1H) 7.46-7.22 (m, 5H) 6.74-6.50 (m, 1H) 6.26-6.08 (m, 1H) 5.79-5.60 (m, 1H) 5.40-5.21 (m, 1H) 4.99-4.87 (m, 1H) 4.43-4.30 (m, 1H) 4.23-3.94 (m, 2H) 2.76-2.42 (m, 2H) 2.21 (s, 3H) 1.95-1.74 (m, 2H) 1.44-1.34 (m, 3H) 0.91 (t, J=7.3 Hz, 3H)

ESI-MS m/z 471 (MH+)

Example 5

7-((3R,5S)-1-acryloyl-5-methylpyrrolidin-3-yl)-4-amino-N-(2-(2-fluorophenyl)propan-2-yl)-6-(prop-1-yn-1-yl)-7H-pyrrolo[2,3-d]pyrimidine-5-carboxamide The title compound was obtained in the same manner as that of Example 1, with the exception that 2-(2-fluorophenyl)propan-2-amine was used instead of (R)-1-(3,5-difluorophenyl)ethan-1-amine in Example 1(5).

$^1$HNMR (CDCl$_3$) δ: 8.28 (s, 1H) 8.11 (d, J=4.4 Hz, 1H) 8.02 (s, 1H) 7.47-7.42 (m, 1H) 7.29-7.23 (m, 1H) 7.15 (t, J=7.7 Hz, 1H) 7.02 (ddd, J=12.5, 8.1, 1.1 Hz, 1H) 6.58-6.35 (m, 2H) 5.79-5.70 (m, 1H) 5.30-5.19 (m, 1H) 4.53 (t, J=10.1 Hz, 0.7H) 4.38-4.25 (m, 1.6H) 3.92 (t, J=8.8 Hz, 0.7H) 2.91-2.78 (m, 1H) 2.70-2.60 (m, 0.3H) 2.54-2.43 (m, 0.7H) 2.28 (d, J=7.0 Hz, 3H) 1.88 (dt, J=10.0, 5.0 Hz, 6H) 1.53 (t, J=6.2 Hz, 3H)

ESI-MS m/z 489 (MH+)

Example 6

7-((3R,5S)-1-acryloyl-5-methylpyrrolidin-3-yl)-4-amino-N—((R)-1-(3-chlorophenyl)ethyl)-6-(prop-1-yn-1-yl)-7H-pyrrolo[2,3-d]pyrimidine-5-carboxamide The title compound was obtained in the same manner as that of Example 1, with the exception that (R)-(+)-1-(3-chlorophenyl)ethylamine hydrochloride was used instead of (R)-1-(3,5-difluorophenyl)ethan-1-amine in Example 1(5).

$^1$HNMR (CDCl3) δ: 8.22 (d, J=5.9 Hz, 1H) 7.75 (d, J=7.0 Hz, 1H) 7.38 (s, 1H) 7.35-7.27 (m, 3H) 6.58-6.33 (m, 2H) 5.78-5.66 (m, 1H) 5.29-5.19 (m, 2H) 4.56 (t, J=10.3 Hz, 0.7H) 4.39-4.20 (m, 1.6H) 3.89 (t, J=8.8 Hz, 0.7H) 2.94-2.82 (m, 1H) 2.66-2.58 (m, 0.3H) 2.46 (dt, J=14.5, 6.1 Hz, 0.7H) 2.18 (d, J=11.0 Hz, 3H) 1.60 (d, J=7.0 Hz, 3H) 1.55-1.51 (m, 3H)

ESI-MS m/z 491,493 (MH+)

Example 7

7-((3R,5S)-1-acryloyl-5-methylpyrrolidin-3-yl)-4-amino-N—((R)-1-(2,4-difluorophenyl)ethyl)-6-(prop-1-yn-1-yl)-7H-pyrrolo[2,3-d]pyrimidine-5-carboxamide The title compound was obtained in the same manner as that of Example 1, with the exception that (R)-(+)-1-(2,4-difluorophenyl)ethylamine hydrochloride was used instead of (R)-1-(3,5-difluorophenyl)ethan-1-amine in Example 1(5).

$^1$HNMR (CDCl$_3$) δ: 8.20 (d, J=5.9 Hz, 1H) 7.98 (d, J=7.7 Hz, 1H) 7.37-7.31 (m, 1H) 6.90-6.81 (m, 2H) 6.58-6.35 (m, 2H) 5.78-5.65 (m, 1H) 5.44-5.37 (m, 1H) 5.30-5.19 (m, 1H) 4.56 (t, J=10.1 Hz, 0.7H) 4.38-4.23 (m, 1.6H) 3.88 (t, J=8.8 Hz, 0.7H) 2.94-2.83 (m, 1H) 2.66-2.57 (m, 0.3H) 2.51-2.42 (m, 0.7H) 2.27 (d, J=9.2 Hz, 3H) 1.61 (d, J=7.0 Hz, 3H) 1.56-1.51 (m, 3H)

ESI-MS m/z 493 (MH+)

Example 8

7-((3R,5S)-1-acryloyl-5-methylpyrrolidin-3-yl)-4-amino-6-(prop-1-yn-1-yl)-N—((S)-2,2,2-trifluoro-1-phenylethyl)-7H-pyrrolo[2,3-d]pyrimidine-5-carboxamide The title compound was obtained in the same manner as that of Example 1, with the exception that (S)-2,2,2-trifluoro-1-phenylethan-1-amine was used instead of (R)-1-(3,5-difluorophenyl)ethan-1-amine in Example 1(5).

$^1$HNMR (CDCl$_3$) δ: 8.40 (d, J=8.8 Hz, 1H) 8.16 (s, 1H) 7.44 (s, 5H) 6.58-6.38 (m, 2H) 5.92-5.84 (m, 1H) 5.81-5.69 (m, 1H) 5.29-5.19 (m, 1H) 4.55 (t, J=10.3 Hz, 0.7H) 4.41-4.24 (m, 1.6H) 3.91 (t, J=8.6 Hz, 0.7H) 2.92-2.80 (m, 1H) 2.70-2.61 (m, 0.3H) 2.54-2.46 (m, 0.7H) 2.35 (d, J=8.4 Hz, 3H) 1.54 (t, J=7.3 Hz, 3H)

ESI-MS m/z 511 (MH+)

Example 9

7-((3R,5S)-1-acryloyl-5-methylpyrrolidin-3-yl)-4-amino-6-(cyclopropylethynyl)-N-(2-phenylpropan-2-yl)-7H-pyrrolo[2,3-d]pyrimidine-5-carboxamide The title compound was obtained in the same manner as that of Example 1, with the exceptions that cyclopropylacetylene was used instead of 1.0 M propyne in DMF solution in Example 1(3), and that 2-phenylpropan-2-amine was used instead of (R)-1-(3,5-difluorophenyl)ethan-1-amine in Example 1(5).

$^1$HNMR (CDCl$_3$) δ: 8.15 (s, 1H) 8.00 (s, 1H) 7.44 (d, J=7.7 Hz, 2H) 7.37 (t, J=7.7 Hz, 2H) 7.32-7.27 (m, 1H) 6.66-6.30 (m, 2H) 5.81-5.69 (m, 1H) 5.38-5.24 (m, 1H) 4.48 (t, J=9.9 Hz, 0.7H) 4.42-4.29 (m, 1.6H) 4.22 (t, J=10.4 Hz, 0.7H) 2.77-2.68 (m, 1H) 2.67-2.60 (m, 0.3H) 2.59-2.52 (m, 0.7H) 1.83 (s, 6H) 1.60-1.52 (m, 4H) 1.08-1.01 (m, 2H) 0.92-0.88 (m, 2H)

ESI-MS m/z 497 (MH+)

Example 10

7-((3R,5S)-1-acryloyl-5-methylpyrrolidin-3-yl)-4-amino-6-(cyclopropylethynyl)-N—((R)-1-(2,3-difluorophenyl)ethyl)-7H-pyrrolo[2,3-d]pyrimidine-5-carboxamide The title compound was obtained in the same manner as that of Example 1, with the exceptions that cyclopropylacetylene was used instead of 1.0 M propyne in DMF solution in Example 1(3), and that (R)-(+)-1-(2,3-difluorophenyl)ethylamine was used instead of (R)-1-(3,5-difluorophenyl)ethan-1-amine in Example 1(5).

$^1$HNMR (CDCl$_3$) δ: 8.17 (d, J=4.0 Hz, 1H) 8.04 (d, J=8.1 Hz, 1H) 7.15-7.05 (m, 3H) 6.58-6.36 (m, 2H) 5.80-5.68 (m, 1H) 5.49-5.42 (m, 1H) 5.34-5.24 (m, 1H) 4.52 (t, J=10.1 Hz, 0.7H) 4.37-4.23 (m, 1.6H) 3.92 (t, J=8.8 Hz, 0.7H) 2.86-2.76 (m, 1H) 2.69-2.63 (m, 0.3H) 2.52-2.46 (m, 0.7H) 1.73-1.63 (m, 4H) 1.55 (t, J=5.3 Hz, 3H) 1.14-1.07 (m, 2H) 1.01-0.92 (m, 2H)

ESI-MS m/z 519 (MH+)

Example 11

Example 11(1)

tert-Butyl(2S,4R)-4-(4-amino-6-bromo-5-(((R)-1-phenylethyl)carbamoyl)-7H-pyrrolo[2,3-d]pyrimidin-7-yl)-2-methylpyrrolidine-1-carboxylate The compound of Reference Example 1(2) (1.00 g), (R)-(+)-1-phenylethylamine (0.503 g), diisopropylethylamine (1.79 g), and N,N-dimethylformamide (10 mL) were added, and subsequently, HATU (1.58 g) was added. The obtained mixture was stirred at room temperature overnight. Thereafter, to the reaction mixture, ethyl acetate and a saturated sodium hydrogen carbonate aqueous solution were added, and the obtained mixture was then extracted with ethyl acetate. The gathered organic layer was washed with water, and then with saturated saline. The resultant was dried over anhydrous sodium sulfate, and was then concentrated under reduced pressure. The obtained residue was purified by silica gel chromatography (hexane:acetone) to obtain an amide form (1.53 g). The obtained compound was used in the subsequent reaction without being further purified.

To the amide form (1.53 g), chloroform (15 mL) was added, and the obtained mixture was then cooled to 0° C. Thereafter, N-bromosuccinimide (0.88 g) was added to the reaction mixture, and the obtained mixture was then stirred at 0° C. for 1 hour. Thereafter, the reaction mixture was concentrated under reduced pressure, and the obtained residue was purified by silica gel chromatography (hexane:ethyl acetate) to obtain a product of interest (1.39 g).

$^1$HNMR (CDCl$_3$) δ: 8.21 (s, 1H) 7.42-7.28 (m, 5H) 6.97 (d, J=7.3 Hz, 1H) 5.36-5.29 (m, 1H) 5.20-5.07 (m, 1H) 4.30 (t, J=10.3 Hz, 1H) 4.04-3.72 (m, 2H) 3.00-2.86 (m, 1H) 2.38 (dt, J=14.3, 6.0 Hz, 1H) 1.63 (d, J=7.0 Hz, 3H) 1.53-1.43 (m, 12H)

ESI-MS m/z 543,545 (MH+)

Example 11(2)

7-((3R,5S)-1-acryloyl-5-methylpyrrolidin-3-yl)-4-amino-6-bromo-N—((R)-1-phenylethyl)-7H-pyrrolo[2,3-d]pyrimidine-5-carboxamide To the compound of Example 11(1) (600 mg), chloroform (3 mL) was added, and the obtained mixture was then cooled to 0° C. Thereafter, trifluoroacetic acid (4.44 g) was added to the reaction mixture, and the thus obtained mixture was then stirred at room temperature for 1 hour. Thereafter, the reaction mixture was concentrated under reduced pressure, and acetonitrile (5 mL) was then added to the residue. The obtained mixture was concentrated under reduced pressure again to obtain an amine form. The obtained compound was used in the subsequent reaction without being further purified.

To the obtained amine form, acetonitrile (3 mL) was added, and the obtained mixture was then cooled to 0° C. Thereafter, acryloyl chloride (99.9 mg) and diisopropylethylamine (713 mg) were added, and the obtained mixture was then stirred at 0° C. for 1 hour. Thereafter, the reaction mixture was concentrated under reduced pressure, and the obtained residue was purified by silica gel chromatography (ethyl acetate:methanol) to obtain a product of interest (281 mg).

¹HNMR (CDCl₃) δ: 8.20 (d, J=7.3 Hz, 1H) 7.42-7.36 (m, 4H) 7.32-7.28 (m, 1H) 7.00-6.94 (m, 1H) 6.57-6.33 (m, 2H) 5.76-5.66 (m, 1H) 5.36-5.29 (m, 1H) 5.14-5.08 (m, 1H) 4.71 (t, J=9.9 Hz, 0.7H) 4.42-4.23 (m, 1.6H) 3.83 (t, J=8.6 Hz, 0.7H) 3.03-2.92 (m, 1H) 2.60-2.57 (m, 0.3H) 2.44-2.40 (m, 0.7H) 1.64 (d, J=6.6 Hz, 3H) 1.56 (dd, J=11.7, 6.2 Hz, 3H)
ESI-MS m/z 497,499 (MH+)

Example 11(3)

7-((3R,5S)-1-acryloyl-5-methylpyrrolidin-3-yl)-4-amino-6-(cyclopropylethynyl)-N—((R)-1-phenylethyl)-7H-pyrrolo[2,3-d]pyrimidine-5-carboxamide The compound of Example 11(2) (65 mg), dichlorobis(triphenylphosphine)dipalladium (9.2 mg), copper(I) iodide (5.0 mg), cyclopropylacetylene (13.0 mg), triethylamine (39.7 mg), and N,N-dimethylformamide (1.3 mL) were added, and the inside of the reaction system was then substituted with nitrogen. After that, the mixture was stirred at 70° C. for 2.5 hours. Thereafter, to the reaction mixture, ethyl acetate and a saturated ammonium chloride aqueous solution were added, and the obtained mixture was then extracted with ethyl acetate. The gathered organic layer was washed with water, and then with saturated saline. The resultant was dried over anhydrous sodium sulfate, and was then concentrated under reduced pressure. The obtained residue was purified by silica gel chromatography (chloroform:methanol) to obtain a product of interest (50 mg).
¹HNMR (CDCl₃) δ: 8.22 (d, J=5.1 Hz, 1H) 7.82 (d, J=7.3 Hz, 1H) 7.43-7.35 (m, 4H) 7.30 (t, J=6.8 Hz, 1H) 6.58-6.34 (m, 2H) 5.77-5.66 (m, 1H) 5.35-5.20 (m, 2H) 4.54 (t, J=10.1 Hz, 0.7H) 4.35-4.25 (m, 1.6H) 3.88 (t, J=8.8 Hz, 0.7H) 2.90-2.78 (m, 1H) 2.65-2.56 (m, 0.3H) 2.49-2.40 (m, 0.7H) 1.63 (d, J=7.0 Hz, 3H) 1.56-1.45 (m, 4H) 1.03-0.91 (m, 2H) 0.84-0.69 (m, 2H)
ESI-MS m/z 483 (MH+)

Example 12

7-((3R,5S)-1-acryloyl-5-methylpyrrolidin-3-yl)-4-amino-6-(3,3-dimethylbut-1-yn-1-yl)-N—((R)-1-phenylethyl)-7H-pyrrolo[2,3-d]pyrimidine-5-carboxamide The title compound was obtained in the same manner as that of Example 11, with the exception that 3,3-dimethyl-1-butyne was used instead of cyclopropylacetylene in Example 11(3).
¹HNMR (CDCl₃) δ: 8.22 (d, J=5.9 Hz, 1H) 7.75 (d, J=7.7 Hz, 1H) 7.38 (dt, J=15.5, 7.1 Hz, 4H) 7.31-7.25 (m, 1H) 6.57-6.34 (m, 2H) 5.77-5.65 (m, 1H) 5.44-5.35 (m, 1H) 5.33-5.15 (m, 1H) 4.63 (t, J=10.1 Hz, 0.7H) 4.40-4.20 (m, 1.6H) 3.89 (t, J=8.8 Hz, 0.7H) 2.90-2.76 (m, 1H) 2.65-2.55 (m, 0.3H) 2.49-2.40 (m, 0.7H) 1.85 (s, 1H) 1.64 (d, J=7.0 Hz, 3H) 1.55 (d, J=5.9 Hz, 3H) 1.26 (s, 9H)
ESI-MS m/z 499 (MH+)

Example 13

7-((3R,5S)-1-acryloyl-5-methylpyrrolidin-3-yl)-4-amino-6-(3-methoxy-3-methylbut-1-yn-1-yl)-N—((R)-1-phenylethyl)-7H-pyrrolo[2,3-d]pyrimidine-5-carboxamide The title compound was obtained in the same manner as that of Example 11, with the exception that 3-methoxy-3-methyl-1-butyne was used instead of cyclopropylacetylene in Example 11(3).

¹HNMR (CDCl₃) δ: 8.17 (s, 1H) 7.61 (d, J=7.7 Hz, 1H) 7.43-7.35 (m, 4H) 7.30 (d, J=7.0 Hz, 1H) 6.57-6.33 (m, 2H) 5.81-5.68 (m, 1H) 5.43-5.33 (m, 1H) 5.29-5.12 (m, 1H) 4.59 (t, J=10.1 Hz, 0.7H) 4.38-4.22 (m, 1.6H) 3.92 (t, J=8.6 Hz, 0.7H) 3.30 (s, 3H) 2.86-2.72 (m, 1H) 2.70-2.60 (m, 1.3H) 2.52-2.44 (m, 0.7H) 1.64 (d, J=7.0 Hz, 3H) 1.55 (t, J=5.5 Hz, 3H) 1.46 (d, J=2.2 Hz, 6H)
ESI-MS m/z 515 (MH+)

Example 14

7-((3R,5S)-1-acryloyl-5-methylpyrrolidin-3-yl)-4-amino-6-(but-1-yn-1-yl)-N—((R)-1-phenylethyl)-7H-pyrrolo[2,3-d]pyrimidine-5-carboxamide The title compound was obtained in the same manner as that of Example 11, with the exception that 1-trimethylsilyl-1-butyne and tetra-n-butylammonium fluoride were used instead of cyclopropylacetylene in Example 11(3).
¹HNMR (CDCl₃) δ: 8.26-8.25 (m, 1H) 7.79 (d, J=7.3 Hz, 1H) 7.42-7.36 (m, 4H) 7.32-7.30 (m, 1H) 6.57-6.37 (m, 2H) 5.76-5.66 (m, 1H) 5.33-5.20 (m, 2H) 4.57 (t, J=10.3 Hz, 0.7H) 4.36-4.22 (m, 1.6H) 3.88 (t, J=8.8 Hz, 0.7H) 2.92-2.81 (m, 1H) 2.65-2.57 (m, 0.3H) 2.48-2.38 (m, 2.7H) 1.63 (d, J=7.0 Hz, 3H) 1.54-1.51 (m, 3H) 1.17-1.12 (m, 3H)
ESI-MS m/z 471 (MH+)

Example 15

7-((3R,5S)-1-acryloyl-5-methylpyrrolidin-3-yl)-4-amino-N-(2-(2-fluorophenyl)propan-2-yl)-6-(3-methylbut-1-yn-1-yl)-7H-pyrrolo[2,3-d]pyrimidine-5-carboxamide The title compound was obtained in the same manner as that of Example 11, with the exceptions that 2-(2-fluorophenyl)propan-2-amine was used instead of (R)-(+)-1-phenylethylamine in Example 11(1), and that 3-methyl-1-butyne was used instead of cyclopropylacetylene in Example 11(3).
¹H NMR (CDCl₃) δ: 7.92 (s, 1H) 7.44 (t, J=7.9 Hz, 1H) 7.30-7.23 (m, 1H) 7.14 (t, J=7.5 Hz, 1H) 7.02 (dd, J=12.6, 8.2 Hz, 1H) 6.58-6.35 (m, 2H) 5.80-5.69 (m, 1H) 5.33-5.16 (m, 1H) 4.58 (t, J=9.9 Hz, 0.7H) 4.38-4.23 (m, 1.6H) 3.91 (t, J=8.4 Hz, 0.7H) 3.03-2.93 (m, 1H) 2.89-2.75 (m, 1H) 2.69-2.60 (m, 0.3H) 2.53-2.43 (m, 0.7H) 1.88 (s, 6H) 1.55 (d, J=5.1 Hz, 3H) 1.36 (d, J=6.6 Hz, 6H)
ESI-MS m/z 517 (MH+)

Example 16

Example 16(1)

tert-Butyl (2R,4S)-4-(benzyloxy)-2-((tosyloxy)methyl)pyrrolidine-1-carboxylate tert-Butyl (2R,4S)-4-(benzyloxy)-2-(hydroxymethyl)pyrrolidine-1-carboxylate (2.0 g) was dissolved in methylene chloride (20 mL), and the obtained solution was then cooled to 0° C. Thereafter, 1,4-diazabicyclo[2.2.2]octane (2.2 g) and tosylate chloride (1.9 g) were added to the reaction solution, and the temperature of the mixture was then increased to room temperature. The mixture was stirred for 4 hours. Thereafter, a saturated sodium hydrogen carbonate aqueous solution was added to the reaction mixture, and the obtained mixture was then extracted with ethyl acetate. The gathered organic layer was washed with saturated saline, was then dried over anhydrous sodium sulfate, and was then concentrated under reduced pressure. The obtained residue was purified by silica gel chromatography (hexane:ethyl acetate) to obtain a product of interest (4.32 g).

$^1$HNMR (CDCl$_3$) δ: 7.78 (d, J=8.1 Hz, 2H), 7.42-7.29 (m, 7H), 4.57-4.41 (m, 2H), 4.39-3.96 (m, 4H), 3.61-3.20 (m, 2H), 2.46 (s, 3H), 2.27-2.02 (m, 2H), 1.48-1.31 (m, 9H)

ESI-MS m/z 462 (MH$^+$)

Example 16(2)

tert-Butyl (2S,4S)-4-(benzyloxy)-2-ethylpyrrolidine-1-carboxylate

Under a nitrogen atmosphere, copper iodide (2.04 g) was suspended in diethyl ether (12 mL), and the obtained suspension was then cooled to 0° C. Thereafter, 1.04M methyl lithium in diethyl ether solution (0.36 mL) was added, and the obtained mixture was then stirred at 0° C. for 30 minutes. Subsequently, the compound of Example 16(1) (1.98 g) in methylene chloride (4.0 mL) solution was added to the reaction mixture, and the temperature of the obtained mixture was then increased to room temperature. The mixture was stirred for 1 hour. Thereafter, the reaction mixture was cooled to 0° C., and a saturated ammonium chloride aqueous solution was then added to the reaction mixture. The thus obtained mixture was extracted with ethyl acetate. The gathered organic layer was washed with saturated saline, was then dried over anhydrous sodium sulfate, and was then concentrated under reduced pressure. The obtained residue was purified by silica gel chromatography (hexane:ethyl acetate) to obtain a product of interest (707 mg).

$^1$HNMR (CDCl$_3$) δ 7.42-7.25 (m, 5H), 4.66-4.40 (m, 2H), 4.17-4.03 (m, 1H), 4.00-3.26 (m, 3H), 2.24-2.09 (m, 1H), 1.96-1.71 (m, 2H), 1.48 (s, 9H), 1.45-1.31 (m, 1H), 0.86 (t, J=7.4 Hz, 3H)

ESI-MS m/z 306 (MH$^+$)

Example 16(3)

tert-Butyl(2S,4S)-2-ethyl-4-hydroxypyrrolidine-1-carboxylate

The compound of Example 16(2) (1.06 g) and a 10% palladium hydroxide carbon catalyst (160 mg) were suspended in ethanol (11 mL) and THF (11 mL), followed by hydrogen substitution, and the resultant was then stirred at room temperature for 20 hours. Thereafter, the reaction mixture was filtrated through Celite, and was then washed with ethanol, and the filtrate was then concentrated under reduced pressure. The obtained residue was purified by silica gel chromatography (hexane:ethyl acetate) to obtain a product of interest (709 mg).

$^1$HNMR (CDCl$_3$) δ 4.46-4.36 (m, 1H), 4.02-3.81 (m, 1H), 3.71-3.35 (m, 2H), 2.15-1.99 (m, 1H), 1.95-1.72 (m, 2H), 1.49 (s, 9H), 1.46-1.35 (m, 1H), 0.86 (t, J=7.5 Hz, 3H)

ESI-MS m/z 216 (MH$^+$)

Example 16(4)

tert-Butyl (2S,4R)-4-(4-chloro-5-iodo-7H-pyrrolo[2,3-d]pyrimidin-7-yl)-2-ethylpyrrolidine-1-carboxylate The compound of Example 16(3) (709 mg) and 4-chloro-5-iodo-7H-pyrrolo[2,3-d]pyrimidine (1.11 g) were dissolved in THF (7.1 mL), and the obtained solution was then cooled to 0° C. Thereafter, triphenylphosphine (1.3 g) and diisopropyl azodicarboxylate (1.00 mL) were added, and the temperature of the obtained mixture was then increased to room temperature, followed by stirring the mixture for 1 hour. Thereafter, the reaction mixture was concentrated under reduced pressure, and the obtained residue was then purified by silica gel chromatography (hexane:ethyl acetate) to obtain the corresponding coupling body. The obtained compound was used in the subsequent reaction without being further purified. Into a pressure resistant tube, the obtained coupling body, THF (5.4 mL), and ammonia water (5.4 mL) were added, and the obtained mixture was then stirred at 100° C. for 14 hours. Thereafter, the reaction mixture was cooled to room temperature, and was then poured into water (12.8 mL), and the mixed solution was then extracted with ethyl acetate. The gathered organic layer was washed with saturated saline, was then dried over anhydrous sodium sulfate, and was then concentrated under reduced pressure. The obtained residue was purified by silica gel chromatography (hexane:acetone) to obtain a product of interest (797 mg).

$^1$HNMR(CDCl$_3$) δ8.29 (s, 1H), 7.14 (s, 1H), 5.67 (brs, 2H), 5.32-5.09 (m, 1H), 4.24-4.08 (m, 1H), 3.95-3.79 (m, 1H), 3.46 (dd, J=9.3, 11.0 Hz, 1H), 2.70-2.55 (m, 1H), 2.06-1.95 (m, 1H), 1.59-1.51 (m, 2H), 1.49 (s, 9H), 0.91 (t, J=7.5 Hz, 3H)

ESI-MS m/z 458 (MH+)

Example 16(5)

tert-Butyl (2S,4R)-4-(4-amino-6-bromo-5-(((R)-1-phenylethyl)carbamoyl)-7H-pyrrolo[2,3-d]pyrimidin-7-yl)-2-ethylpyrrolidine-1-carboxylate The compound of Example 16(4) (797 mg), dichlorobis(triphenylphosphine)dipalladium(25 mg), and (R)-(+)-1-phenylethylamine (0.55 mL) were suspended in DMF (8.0 mL), followed by carbon monoxide substitution, and the resultant was then stirred at 80° C. for 2 hours. Thereafter, the reaction mixture was cooled to room temperature, water was then added thereto, and the obtained mixture was then extracted with ethyl acetate. The gathered organic layer was washed with saturated saline, was then dried over anhydrous sodium sulfate, and was then concentrated under reduced pressure. The obtained residue was purified by silica gel chromatography (hexane:acetone) to obtain the corresponding amide form. The obtained compound was used in the subsequent reaction without being further purified. The obtained amide form was dissolved in acetonitrile (8.2 mL), and the obtained solution was then cooled to −10° C. Thereafter, N-bromosuccinimide (457 mg) in acetonitrile (8.2 mL) solution was slowly added dropwise to the solution, and the reaction mixture was then stirred for 30 minutes. Thereafter, to the reaction mixture, a sodium sulfite aqueous solution and a sodium hydrogen carbonate aqueous solution were added, and the obtained mixture was then extracted with ethyl acetate. The gathered organic layer was washed with saturated saline, was then dried over anhydrous sodium sulfate, and was then concentrated under reduced pressure. The obtained residue was purified by silica gel chromatography (hexane:acetone) to obtain a product of interest (650 mg).

$^1$HNMR (CDCl$_3$) δ 8.23 (s, 1H), 7.49-7.29 (m, 5H), 6.98 (d, J=7.4 Hz, 1H), 5.41-5.28 (m, 1H), 5.24-5.04 (m, 1H), 4.38-4.22 (m, 1H), 4.07-3.68 (m, 1H), 3.19-2.83 (m, 11H), 2.43-2.29 (m, 1H), 2.25-1.67 (m, 3H), 1.66 (d, J=6.9 Hz, 3H), 1.51 (s, 9H), 0.98 (t, J=7.4 Hz, 3H)

ESI-MS m/z 557,559 (MH$^+$)

Example 16(6)

7-((3R,5S)-1-acryloyl-5-ethylpyrrolidin-3-yl)-4-amino-6-bromo-N—((R)-1-phenylethyl)-7H-pyrrolo[2,3-d]pyrimidine-5-carboxamide To the compound of Example 16(5) (650 mg), acetonitrile (9.7 mL) was added, and the obtained mixture was then cooled to 0° C. Thereafter, sodium iodide (1.05 g) and trimethylsilyl chloride (0.89 mL) were added, and the obtained mixture was then stirred at 0° C. for 1 hour. Thereafter, to the reaction mixture, ethanol (9.7 mL), isopropylethylamine (2.0 mL), and acrylic acid anhydride (0.16 mL) were successively added, and the obtained mixture was then stirred at 0° C. for 30 minutes. Thereafter, to the reaction mixture, ammonia water and water were added, and the obtained mixture was then extracted with ethyl acetate. The gathered organic layer was washed with saturated saline, was then dried over anhydrous sodium sulfate, and was then concentrated under reduced pressure. The obtained residue was purified by silica gel chromatography (hexane:acetone) to obtain a product of interest (256 mg).

$^1$HNMR (CDCl$_3$) δ 8.27-8.16 (m, 1H), 7.47-7.29 (m, 5H), 6.98 (d, J=7.3 Hz, 1H), 6.61-6.29 (m, 2H), 5.84-5.63 (m, 1H), 5.43-5.26 (m, 1H), 5.22-5.01 (m, 1H), 4.80-3.82 (m, 3H), 3.23-2.92 (m, 1H), 2.58-2.30 (m, 1H), 2.22-1.79 (m, 2H), 1.66 (d, J=7.0 Hz, 3H), 1.07-0.96 (m, 3H)

ESI-MS m/z 511,513 (MH$^+$)

Example 16(7)

7-((3R,5S)-1-acryloyl-5-ethylpyrrolidin-3-yl)-4-amino-N—((R)-1-phenylethyl)-6-(prop-1-yn-1-yl)-7H-pyrrolo[2,3-d]pyrimidine-5-carboxamide 1.0 M Propyne in DMF solution (0.70 mL) was added to the compound of Example 16(6) (120 mg), acetonitrile (1.2 mL), triethylamine (0.10 mL), PdCl$_2$(PPh$_3$)$_2$ (8.2 mg), and copper(I) iodide (0.4 mg), followed by nitrogen substitution, and the mixture was then stirred at 60° C. for 2 hours. Thereafter, the reaction mixture was cooled to room temperature, and ethyl acetate and a saturated ammonium chloride aqueous solution were added to the mixture. The thus obtained mixture was extracted with ethyl acetate, and the gathered organic layer was washed with water, and then with saturated saline. The resultant was dried over anhydrous sodium sulfate, and was then concentrated under reduced pressure. The obtained residue was purified by silica gel chromatography (ethyl acetate:methanol) to obtain a product of interest (102 mg).

$^1$HNMR (CDCl$_3$) δ: 8.26 (s, 1H), 7.79 (br d, J=7.0 Hz, 1H), 7.46-7.30 (m, 5H), 6.58-6.31 (m, 2H), 5.80-5.65 (m, 1H), 5.33-5.15 (m, 2H), 4.59-3.85 (m, 3H), 3.03-2.33 (m, 2H), 2.25-1.70 (m, 5H), 1.65 (d, J=6.8 Hz, 6H), 1.09-0.91 (m, 3H)

ESI-MS m/z 471 (MH$^+$)

Example 17

7-((3R,5S)-1-acryloyl-5-ethylpyrrolidin-3-yl)-4-amino-6-(cyclopropylethynyl)-N—((R)-1-phenylethyl)-7H-pyrrolo[2,3-d]pyrimidine-5-carboxamide The title compound was obtained in the same manner as that of Example 16, with the exception that cyclopropylacetylene was used instead of 1.0 M propyne in DMF solution in Example 16(7).

$^1$HNMR (CDCl$_3$) δ: 8.31-8.16 (m, 1H), 7.84 (d, J=7.4 Hz, 1H), 7.46-7.30 (m, 5H), 6.64-6.32 (m, 2H), 5.82-5.67 (m, 1H), 5.39-5.17 (m, 2H), 4.67-3.81 (m, 3H), 3.02-2.80 (m, 1H), 2.62-1.71 (m, 3H), 1.65 (d, J=6.9 Hz, 3H), 1.58-1.47 (m, 1H), 1.06-0.92 (m, 5H), 0.85-0.70 (m, 2H)

ESI-MS m/z 497 (MH$^+$)

Example 18

7-((3R,5R)-1-acryloyl-5-(methoxymethyl)pyrrolidin-3-yl)-4-amino-6-(cyclopropylethynyl)-N—((R)-1-phenylethyl)-7H-pyrrolo[2,3-d]pyrimidine-5-carboxamide The title compound was obtained in the same manner as that of Example 16, with the exceptions that tert-butyl (2R,4S)-4-hydroxy-2-(methoxymethyl)pyrrolidine-1-carboxylate was used instead of the compound of Example 16(3) in Example 16(4), and that cyclopropylacetylene was used instead of 1.0 M propyne in DMF solution in Example 16(7).

$^1$HNMR (CDCl$_3$) δ: 8.29-8.22 (m, 1H), 7.86-7.80 (m, 1H), 7.36-7.44 (m, 4H), 7.34-7.28 (m, 1H), 6.48-6.37 (m, 2H), 5.78-5.69 (m, 1H), 5.29-5.15 (m, 2H), 4.55-4.30 (m, 2H), 3.96-3.65 (m, 3H), 3.42 (s, 3H), 3.18-3.06 (m, 0.3H), 2.90-2.80 (m, 0.3H), 2.64-2.58 (m, 0.3H), 2.47-2.35 (m, 0.7H), 1.64 (d, 3H, J=6.9 Hz), 1.58-1.47 (m, 1H), 1.04-0.94 (m, 2H), 0.87-0.69 (m, 2H)

ESI-MS m/z 513 (MH$^+$)

Example 19

7-((3R,5R)-1-acryloyl-5-(ethoxymethyl)pyrrolidin-3-yl)-4-amino-6-(cyclopropylethynyl)-N—((R)-1-phenylethyl)-7H-pyrrolo[2,3-d]pyrimidine-5-carboxamide The title compound was obtained in the same manner as that of Example 16, with the exceptions that tert-butyl (2R,4S)-2-(ethoxymethyl)-4-hydroxypyrrolidine-1-carboxamide was used instead of the compound of Example 16(3) in Example 16(4), and that cyclopropylacetylene was used instead of 1.0 M propyne in DMF solution in Example 16(7).

$^1$HNMR (CDCl$_3$) δ: 8.28-8.18 (m, 1H), 7.84 (br d, J=7.0 Hz, 1H), 7.47-7.29 (m, 5H), 6.82-6.35 (m, 2H), 5.79-5.68 (m, 1H), 5.40-5.14 (m, 2H), 4.63-3.53 (m, 7H), 3.20-2.79 (m, 1H), 2.69-2.40 (m, 1H), 1.67-1.63 (m, 3H), 1.59-1.47 (m, 1H), 1.22 (t, J=7.0 Hz, 3H), 1.05-0.92 (m, 2H), 0.87-0.72 (m, 2H)

ESI-MS m/z 527 (MH$^+$)

Comparative Example 1

4-Amino-N-(4-(methoxymethyl)phenyl)-7-(1-methylcyclopropyl)-6-(prop-1-yn-1-yl)-7H-pyrrolo[2,3-d]pyrimidine-5-carboxamide The title compound was obtained by the method described in Example 95 of International Publication No. WO 2017/146116.

ESI-MS m/z 390 (MH+)

Comparative Example 2

1-((3R,5S)-1-acryloyl-5-methylpyrrolidin-3-yl)-4-amino-N-(4-(2-(dimethylamino)-2-oxoethyl)-2,3-dimethylphenyl)-1H-pyrazolo[3,4-d]pyrimidine-3-carboxamide The title compound was obtained by the method described in Example 79 of International Publication No. WO 2017/038838.
ESI-MS m/z 505 (MH+)

Comparative Example 3

7-((3R,5S)-1-acryloyl-5-methylpyrrolidin-3-yl)-4-amino-N-(cyclohexylmethyl)-6-(prop-1-yn-1-yl)-7H-pyrrolo[2,3-d]pyrimidine-5-carboxamide The title compound was obtained in the same manner as that of Example 1, with the exception that cyclohexylmethanamine was used instead of (R)-1-(3,5-difluorophenyl)ethan-1-amine in Example 1(5).
$^1$H NMR (DMSO-d6) δ:8.68-8.31 (m, 1H) 8.20-8.10 (m, 1H) 8.09-7.97 (m, 1H) 7.59-7.20 (m, 1H) 6.74-6.49 (m, 1H) 6.25-6.09 (m, 1H) 5.78-5.60 (m, 1H) 5.40-5.20 (m, 1H) 4.44-4.29 (m, 1H) 4.23-3.92 (m, 2H) 3.25-3.12 (m, 2H) 2.76-2.40 (m, 2H) 2.25 (s, 3H) 1.81-1.45 (m, 5H) 1.43-1.34 (m, 3H) 1.30-0.90 (m, 6H)
ESI-MS m/z 449 (MH+)

Comparative Example 4

7-((3R,5S)-1-acryloyl-5-methylpyrrolidin-3-yl)-4-amino-N-(2-methylbenzyl)-6-(prop-1-yn-1-yl)-7H-pyrrolo[2,3-d]pyrimidine-5-carboxamide The title compound was obtained in the same manner as that of Example 1, with the exception that o-tolylmethanamine was used instead of (R)-1-(3,5-difluorophenyl)ethan-1-amine in Example 1(5).
$^1$HNMR (DMSO-d6) δ:8.37-8.27 (m, 1H) 8.19-8.09 (m, 1H) 7.39-7.30 (m, 1H) 7.26-7.11 (m, 4H) 6.68-6.48 (m, 1H) 6.24-6.07 (m, 1H) 5.80-5.60 (m, 1H) 5.36-5.17 (m, 1H) 4.52 (d, J=5.7 Hz, 2H) 4.42-4.28 (m, 1H) 4.22-3.92 (m, 2H) 2.73-2.42 (m, 2H) 2.33 (s, 3H) 2.02 (s, 3H) 1.43-1.32 (m, 3H)
ESI-MS m/z 457 (MH+)

Comparative Example 5

7-((3R,5S)-1-acryloyl-5-methylpyrrolidin-3-yl)-4-amino-N-methyl-N—((R)-1-phenylethyl)-6-(prop-1-yn-1-yl)-7H-pyrrolo[2,3-d]pyrimidine-5-carboxamide The title compound was obtained in the same manner as that of Example 1, with the exception that (R)—N-methyl-1-phenylethan-1-amine was used instead of (R)-1-(3,5-difluorophenyl)ethan-1-amine in Example 1(5).
$^1$HNMR (CDCl$_3$) δ: 8.23 (d, J=5.9 Hz, 1H) 7.50-7.28 (m, 4H) 7.09-6.88 (m, 1H) 6.57-6.34 (m, 2H) 5.79-5.64 (m, 1H) 5.22 (t, J=9.3 Hz, 1H) 4.48 (t, J=9.7 Hz, 0.6H) 4.39-4.20 (m, 1.9H) 3.90 (t, J=8.6 Hz, 0.5H) 2.85 (s, 4H) 2.66-2.63 (m, 0.4H) 2.51-2.44 (m, 0.6H) 2.07 (s, 2H) 1.66 (d, J=4.8 Hz, 3H) 1.52 (d, J=5.9 Hz, 3H)
ESI-MS m/z 471 (MH+)

Comparative Example 6(1)

tert-Butyl (2S,4R)-4-(4-amino-5-(((R)-1-phenylethyl)carbamoyl)-6-(prop-1-yn-1-yl)-7H-pyrrolo[2,3-d]pyrimidin-7-yl)-2-methylpyrrolidine-1-carboxylate 1.0 M Propyne in DMF solution (2.1 mL) was added to the compound of Example 11(1) (230 mg), acetonitrile (4.6 mL), triethylamine (0.29 mL), PdCl$_2$(PPh$_3$)$_2$ (5.9 mg), and copper(I) iodide (1.6 mg), followed by nitrogen substitution, and the obtained mixture was then stirred at 70° C. for 1 hour. Thereafter, the reaction mixture was cooled to room temperature, and ethyl acetate and a saturated sodium hydrogen carbonate aqueous solution were then added to the mixture. The thus obtained mixture was extracted with ethyl acetate, and the gathered organic layer was washed with water and then with saturated saline. The resultant was dried over anhydrous sodium sulfate, and was then concentrated under reduced pressure. The obtained residue was purified by silica gel chromatography (hexane:ethyl acetate) to obtain a product of interest (193 mg).
$^1$HNMR (CDCl$_3$) δ: 8.23 (s, 1H) 7.79 (d, J=6.8 Hz, 1H) 7.46-7.27 (m, 5H) 5.40-5.17 (m, 2H) 4.28-3.64 (m, 3H) 2.85-2.68 (m, 1H) 2.46-2.36 (m, 1H) 2.15-1.97 (m, 3H) 1.62 (d, J=6.8 Hz, 3H) 1.56-1.32 (m, 12H)
ESI-MS m/z 503 (MH+)

Comparative Example 6(2)

4-Amino-7-((3R,5S)-5-methylpyrrolidin-3-yl)-N—((R)-1-phenylethyl)-6-(prop-1-yn-1-yl)-7H-pyrrolo[2,3-d]pyrimidine-5-carboxamide Hydrochloride To the compound of Comparative Example 6(1) (530 mg), 4 M hydrochloric acid in 1,4-dioxane solution (5 mL) was added, and the obtained mixture was then stirred at room temperature for 2 hours. Thereafter, the reaction mixture was concentrated under reduced pressure to obtain a product of interest (420 mg).
ESI-MS m/z 403 (MH+)

Comparative Example 6(3)

4-Amino-7-((3R,5S)-1-((E)-but-2-enoyl)-5-methylpyrrolidin-3-yl)-N—((R)-1-phenylethyl)-6-(prop-1-yn-1-yl)-7H-pyrrolo[2,3-d]pyrimidine-5-carboxamide To the compound of Comparative Example 6(2) (18 mg), acetonitrile (0.5 mL) was added, and the obtained mixture was then cooled to 0° C. Thereafter, acryloyl chloride (0.004 mL) and diisopropylethylamine (0.036 mL) were added to the reaction mixture, and the thus obtained mixture was then stirred at 0° C. for 1 hour. Thereafter, the reaction mixture was concentrated under reduced pressure, and was then subjected to reverse phase preparative HPLC (water:acetonitrile (0.1% formic acid)) to obtain a product of interest (8.7 mg).
$^1$HNMR (CDCl$_3$) δ: 8.31 (s, 1H) 8.14 (d, J=6.2 Hz, 1H) 7.77 (d, J=7.0 Hz, 1H) 7.39-7.36 (m, 4H) 7.33-7.31 (m, 1H) 7.03-6.90 (m, 1H) 6.06 (dd, J=14.3 Hz, 1H) 5.28-5.17 (m, 2H) 4.48 (t, J=10.1 Hz, 2H) 4.35-4.20 (m, 2H) 3.88 (t, 8.8 Hz, 1H) 2.84-2.76 (m, 1H) 2.64-2.40 (m, 1H) 2.05 (d, J=10.6

Hz, 3H) 1.92 (d, J=6.6 Hz, 1H) 1.85 (d, J=7.0 Hz, 2H) 1.62 (d, J=7.0 Hz, 3H) 1.55 (dd, J=9.0, 5.7 Hz, 3H)

ESI-MS m/z 471 (MH+)

The compounds synthesized in the above-described Examples and Comparative Examples are shown below.

TABLE B

| Example No. | Structural Formula |
|---|---|
| 1 | |
| 2 | |
| 3 | |
| 4 | |
| 5 | |
| 6 | |

TABLE B-continued
| Example No. | Structural Formula |
|---|---|
| 7 | 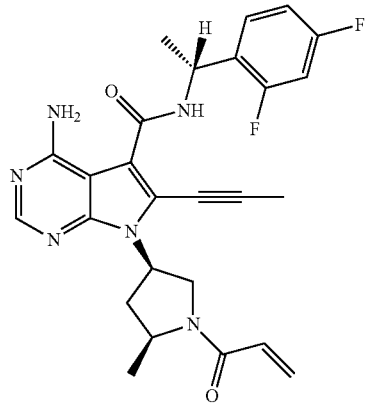 [SMILES: C=CC(=O)N1C[C@H](n2c(C#CC)c(C(=O)N[C@H](C)c3ccc(F)cc3F)c3c(N)ncnc32)C[C@@H]1C] |
| 8 | 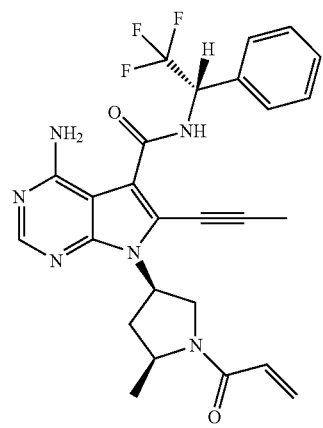 [SMILES: C=CC(=O)N1C[C@H](n2c(C#CC)c(C(=O)N[C@@H](c3ccccc3)C(F)(F)F)c3c(N)ncnc32)C[C@@H]1C] |
| 9 | 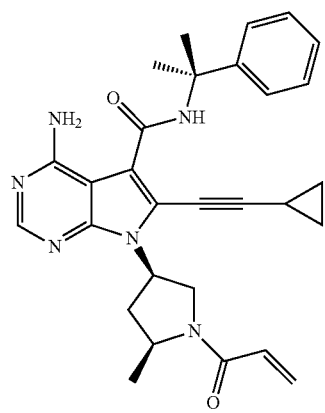 |
| 10 | 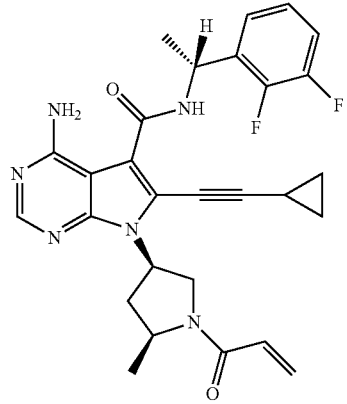 [SMILES: C=CC(=O)N1C[C@H](n2c(C#CC3CC3)c(C(=O)N[C@H](C)c3cccc(F)c3F)c3c(N)ncnc32)C[C@@H]1C] |
| 11 | 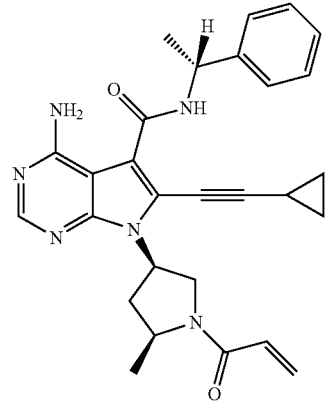 [SMILES: C=CC(=O)N1C[C@H](n2c(C#CC3CC3)c(C(=O)N[C@H](C)c3ccccc3)c3c(N)ncnc32)C[C@@H]1C] |
| 12 | 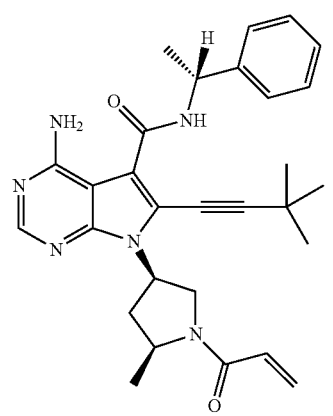 [SMILES: C=CC(=O)N1C[C@H](n2c(C#CC(C)(C)C)c(C(=O)N[C@H](C)c3ccccc3)c3c(N)ncnc32)C[C@@H]1C] |

TABLE B-continued
| Example No. | Structural Formula |
|---|---|
| 13 | 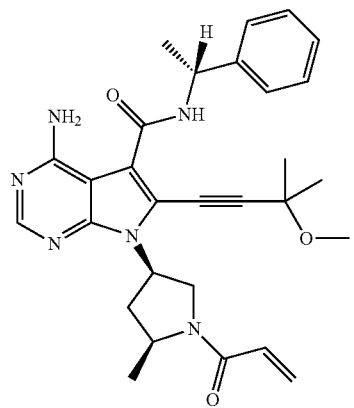 [SMILES: C=CC(=O)N1C[C@H](n2c(C#CC(C)(C)OC)c(C(=O)N[C@H](C)c3ccccc3)c3c(N)ncnc32)C[C@@H]1C] |
| 14 | 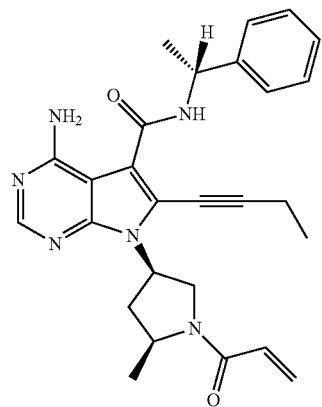 [SMILES: C=CC(=O)N1C[C@H](n2c(C#CCC)c(C(=O)N[C@H](C)c3ccccc3)c3c(N)ncnc32)C[C@@H]1C] |
| 15 | 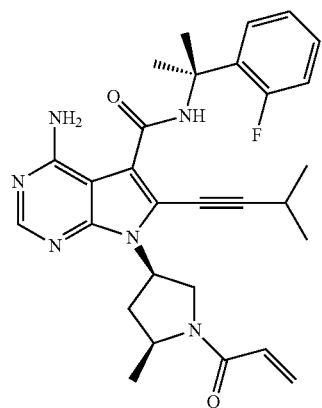 |
TABLE B-continued
| Example No. | Structural Formula |
|---|---|
| 16 | 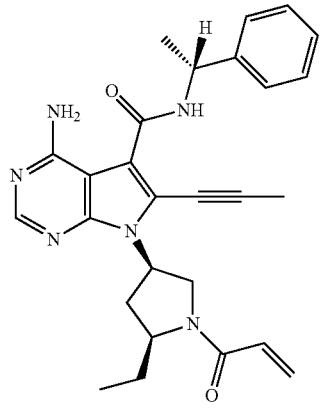 [SMILES: C=CC(=O)N1C[C@H](n2c(C#CC)c(C(=O)N[C@H](C)c3ccccc3)c3c(N)ncnc32)C[C@@H]1CC] |
| 17 | |
| 18 | 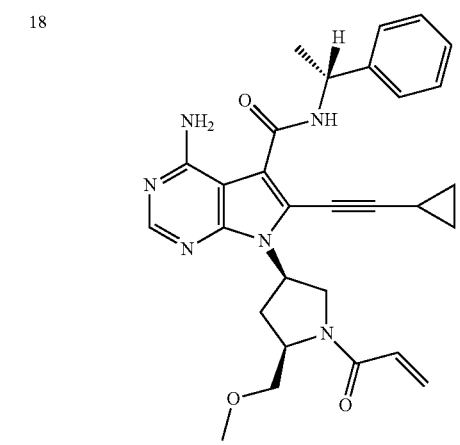 |

TABLE B-continued

| Example No. | Structural Formula |
|---|---|
| 19 | |

TABLE C

| Comp. Ex. No. | Structural Formula |
|---|---|
| 1 | |
| 2 | |
| 3 | |
| 4 | |
| 5 | |

TABLE C-continued

| Comp. Ex. No. | Structural Formula |
|---|---|
| 6 | (structure shown) |

Test Example 1 Measurement of Inhibitory Effect (In Vitro) on HER2 Phosphorylation Activity In order to determine conditions for a method of measuring the in vitro inhibitory activity of a compound against HER2 phosphorylation activity, based on the report regarding a HER2 kinase reaction using, as a substrate, a peptide having the same sequence (5-FAM-EEPLYWSFPAKKK-CONH$_2$) as that of ProfilerPro Peptide 22 of PerkinElmer (Xie H et al., PLoS One. 2011; 6(7): e21487), ProfilerPro Peptide 22 was used as a substrate. A purified recombinant human HER2 protein used in the present test was purchased from Carna Biosciences, Inc. Upon the measurement of the inhibitory activity of the compound, first, the compound of the present invention was diluted stepwise with dimethyl sulfoxide (DMSO). Subsequently, the HER2 protein, the substrate peptide (final concentration: 1 μM), manganese chloride (final concentration: 10 mM), ATP (final concentration: 5 μM), and the compound of the present invention in DMSO solution (final concentration of DMSO: 5%) were added to a buffer for the kinase reaction (13.5 mM Tris (pH 7.5), 2 mM dithiothreitol, and 0.009% Tween 20), and the obtained mixture was then incubated at 25° C. for 30 minutes, so that the kinase reaction was carried out. To the reaction solution, EDTA was added to a final concentration of 30 mM, so as to terminate the reaction. Finally, using LabChip (registered trademark) EZ Reader II (PerkinElmer), an unphosphorylated substrate peptide (S) and a phosphorylated peptide (P) were separated and detected according to microchannel capillary electrophoresis. From the peak heights of S and P, the amount of the phosphorylation reaction was obtained, and the concentration of the compound capable of inhibiting the phosphorylation reaction by 50% was defined as an IC50 value (nM). The results are shown in Table 1.

Test Example 2 Measurement of Inhibitory Action (In Vitro) Against HER2 Exon 20 Insertion Mutant (HER2ex20insYVMA) Phosphorylation Activity In order to determine conditions for a method of measuring the in vitro inhibitory activity of a compound against HER2 exon 20 insertion mutant phosphorylation activity, as in the case of HER2, ProfilerPro Peptide 22 was used as a substrate. A purified recombinant human HER2 exon 20 insertion mutant (A775_G776insYVMA) protein is shown in SEQ ID NO: 7, and was purchased from SignalChem. Upon the measurement of the inhibitory activity of the compound, first, the compound of the present invention was diluted stepwise with dimethyl sulfoxide (DMSO). Subsequently, the HER2 exon 20 insertion mutant protein and the compound of the present invention in DMSO solution (final concentration of DMSO: 5%) were added into a buffer for the kinase reaction (13.5 mM Tris (pH 7.5), 2 mM dithiothreitol, and 0.009% Tween 20), and the obtained mixture was then pre-incubated at 25° C. for 30 minutes. Thereafter, the substrate peptide (final concentration: 1 μM), manganese chloride (final concentration: 25 mM), magnesium chloride (final concentration: 20 mM), and ATP (final concentration: 200 μM) were added into the reaction mixture, and the thus obtained mixture was then incubated at 25° C. for 220 minutes, so that the kinase reaction was carried out. To the reaction solution, EDTA was added to a final concentration of 30 mM, so as to terminate the reaction. Finally, using LabChip (registered trademark) EZ Reader II (PerkinElmer), an unphosphorylated substrate peptide (S) and a phosphorylated peptide (P) were separated and detected according to microchannel capillary electrophoresis. From the peak heights of S and P, the amount of the phosphorylation reaction was obtained, and the concentration of the compound capable of inhibiting the phosphorylation reaction by 50% was defined as an IC50 value (nM). The results are shown in Table 1.

TABLE 1

| Example No. | HER2 inhibitory activity IC50 value (nM) | HER2ex20insYVMA inhibitory activity IC50 value (nM) |
|---|---|---|
| 1 | 2.7 | 0.34 |
| 2 | 2.5 | <0.30 |
| 3 | 5.8 | <0.30 |
| 4 | 3.9 | 0.37 |
| 5 | 7.7 | 0.38 |
| 6 | 2.8 | <0.30 |
| 7 | 4.9 | 0.39 |
| 8 | 10 | <0.30 |
| 9 | 5.6 | 0.32 |
| 10 | 2.2 | <0.30 |
| 11 | 3.2 | <0.30 |
| 12 | 3.4 | 0.39 |
| 13 | 5.2 | 0.44 |
| 14 | 2.2 | <0.30 |
| 15 | 4.6 | 0.42 |
| 16 | 3.3 | 0.44 |
| 17 | 2.9 | 0.54 |
| 18 | 2.3 | <0.30 |
| 19 | 4.4 | 1.1 |
| Comp. Ex. 1 | >10000 | >10000 |
| Comp. Ex. 2 | 19 | 4.4 |
| Comp. Ex. 3 | 630 | 380 |
| Comp. Ex. 4 | 54 | 11 |
| Comp. Ex. 5 | 130 | 14 |
| Comp. Ex. 6 | 390 | >10000 |

From the above results, it was found that the compound of the present invention has excellent inhibitory activity against phosphorylation of HER2 and against phosphorylation of HER2 exon 20 insertion mutant.

Test Example 3 Measurement of Growth Inhibitory Activity Against HER2 Expressing Cell Line SK-BR-3 cells as a HER2 overexpressing human breast cancer cell line were suspended in a McCoy's 5a medium (manufactured by Life Technologies) supplemented with 10% fetal bovine serum. The cell suspension was seeded in each well of a 384-well flat-bottom microplate, and was then cultured in a 5% carbon dioxide gas-containing culture vessel at 37° C. for 1 day. Thereafter, the compound of the present invention was dissolved in DMSO, and the compound was diluted to 500 times the final concentration in DMSO. The compound in the DMSO solution was diluted with DMSO solution or the medium used in the suspension of the cells, and the obtained solution was then added to each well of the culture plate so that the final concentration of DMSO was 0.2%. The obtained mixture was further cultured in the 5% carbon dioxide gas-containing culture vessel at 37° C. for 3 days. After completion of the culture for 3 days in the presence of the compound, the cells were counted using CellTiter-Glo 2.0 (manufactured by Promega), and the growth inhibition percentage was then calculated according to the following equation. The concentration of the compound, in which the growth of the cells can be inhibited by 50%, was defined as IC50 (nM).

Growth inhibitory percentage (%)=$(C-T)/(C) \times 100$

T: Emission intensity from the well to which the test compound was added
C: Emission intensity from the well to which the test compound was not added
The results are shown in the following Table 2.

Test Example 4 Measurement of Growth Inhibitory Activity Against HER2 Exon 20 Insertion Mutant Expressing Cell Line Growth inhibitory activity against the HER2 exon 20 insertion mutant was measured using Ba/F3 cells that were a mouse B lymphocyte precursor cell line, into which a human HER2 exon 20 insertion mutant gene had been introduced. The Ba/F3 cells were maintained in an RPMI-1640 medium (Thermo Fisher Scientific) supplemented with 10% fetal bovine serum (FBS), 100 U/mL penicillin, 100 μg/mL streptomycin (Thermo Fisher Scientific) and 1 ng/mL mouse interleukin-3 (mIL-3) (CST). Thereafter, a pCDNA3.1-hyg(+) vector, into which a human HER2 exon 20 insertion mutant gene (A775_G776insYVMA (HER2ex20insYVMA)), Internal Ribosome Binding Sequence (IRES), and a Kusabira orange gene had been incorporated, was introduced into the Ba/F3 cells according to an electroporation method using Amaxa (registered trademark) Cell Line Nucleofector (registered trademark) Kit V. The Ba/F3 cells expressing the HER2 exon 20 insertion mutant (Ba/F3-HER2insYVMA), which were selected with hygromycin B (Nacalai Tesque), exhibited mIL-3-independent growth.

Upon evaluation of cell growth inhibitory activity, the Ba/F3-HER2insYVMA cells were suspended in an RPMI-1640 medium supplemented with 10% FBS, 100 U/mL penicillin, and 100 μg/mL streptomycin. The cell suspension was seeded in each well of a 96-well flat-bottom microplate, and was then cultured in a 5% carbon dioxide gas-containing culture vessel at 37° C. for 1 day. The compound of the present invention was dissolved in DMSO, and was then diluted with DMSO or the medium used in the suspension of the cells. The obtained solution was then added to each well of the culture plate, so that the final concentration of DMSO became 0.2%. The obtained mixture was further cultured in the 5% carbon dioxide gas-containing culture vessel at 37° C. for 3 days. After completion of the culture for 3 days in the presence of the compound, the cells were counted using CellTiter-Glo 2.0 (manufactured by Promega), and the growth inhibition percentage was then calculated according to the following equation. The concentration of the compound, in which the growth of the cells can be inhibited by 50%, was defined as IC50 (nM).

Growth inhibitory percentage (%)=$(C-T)/(C) \times 100$

T: Emission intensity from the well to which the test compound was added
C: Emission intensity from the well to which the test compound was not added
The results are shown in the following Table 2.

TABLE 2

| Example No. | SK-BR-3 cell growth inhibitory activity IC50 value (nM) | HER2ex20insYVMA cell growth inhibitory activity IC50 value (nM) |
| --- | --- | --- |
| 1 | 9.3 | 17 |
| 2 | 2.8 | 12 |
| 3 | 4.5 | 25 |
| 4 | 5.6 | 20 |
| 5 | 4.0 | 14 |
| 6 | 10 | 28 |
| 7 | 12 | 40 |
| 8 | 14 | 26 |
| 9 | 4.2 | 24 |
| 10 | 13 | 29 |
| 11 | 6.6 | 29 |
| 12 | 17 | 43 |
| 13 | 14 | 23 |
| 14 | 8.1 | 27 |
| 15 | 7.0 | 40 |
| 16 | 1.4 | 9.7 |
| 17 | 4.0 | 20 |
| 18 | 3.4 | 14 |
| 19 | 17 | 50 |
| Comp. Ex. 1 | >10000 | >10000 |
| Comp. Ex. 2 | 25 | 1900 |
| Comp. Ex. 3 | 4300 | 3400 |
| Comp. Ex. 4 | 340 | 900 |
| Comp. Ex. 5 | 400 | 1300 |
| Comp. Ex. 6 | 3000 | 4100 |

From the above results, it was found that the compound group of the present invention has excellent cell growth inhibitory activity even against the HER2 expressing cell line (SK-BR-3) and also, against the HER2 exon 20 insertion mutant expressing cell line (Ba/F3-HER2insYVMA).

Test Example 5 Measurement of Growth Inhibitory Activity Against HER2 Expressing Cell Line (NCI-N87)

NCI-N87 cells as a HER2 overexpressing human stomach cancer cell line (American Type Culture Collection, Cat No. ATCC (registered trademark) CRL-5822) were suspended in an RPMI640 medium (Wako Pure Chemical Industries, Ltd.) supplemented with 10% fetal bovine serum. Subsequently, the cell suspension was seeded in each well of a 96-well flat-bottom microplate, and was then cultured in a 5% carbon dioxide gas-containing culture vessel at 37° C. for 1 day. Thereafter, the compound of the present invention was dissolved in DMSO, and the compound was diluted to 1000 times the final concentration in DMSO. The compound in the DMSO solution was diluted with the medium used in the suspension of the cells, and the obtained solution was then added to each well of the culture plate, so that the final concentration of DMSO became 0.1%. Regarding a control well, DMSO was diluted with the medium used in the suspension of the cells, and the obtained solution was then added to each well of the culture plate, so that the final concentration of DMSO became 0.1%. After addition of a drug solution, the obtained mixture was further cultured in the 5% carbon dioxide gas-containing culture vessel at 37° C. for 3 days. After completion of the culture for 3 days in the presence of the compound, the cells were counted using CellTiter-Glo 2.0 (manufactured by Promega) in accordance with the protocols recommended by Promega. The growth inhibition percentage was calculated according to the following equation. The concentration of the compound, in which the growth of the cells can be inhibited by 50%, was defined as IC50 (nM).

Growth inhibitory percentage (%)=$(C-T)/(C) \times 100$

T: Emission intensity from the well to which the test compound was added
C: Emission intensity from the well to which the test compound was not added The results are shown in the following Table 3.

TABLE 3

| Example No. | NCI-N87 cell growth inhibitory activity IC50 value (nM) |
|---|---|
| 1 | 10.7 |
| 2 | 3.0 |
| 3 | 4.7 |
| 4 | 5.6 |
| 5 | 7.0 |
| 6 | 8.5 |
| 7 | 11.1 |
| 8 | 9.7 |
| 9 | 6.2 |
| 10 | 10.5 |
| 11 | 9.9 |
| 12 | 15.0 |
| 13 | 11.7 |
| 14 | 9.1 |
| 15 | 11.6 |
| 16 | 0.9 |
| 17 | 2.2 |
| 18 | 2.6 |
| 19 | 7.9 |

From the above results, it was found that the compound of the present invention has excellent cell growth inhibitory activity even against the HER2 overexpressing cell line (NCI-N87).

Test Example 6 Evaluation of Oral Absorbability

The compound of the present invention was suspended or dissolved in 0.5% HPMC aqueous solution and 0.1 N hydrochloric acid, and the obtained suspension or solution was orally administered to BALB/cA mice (CLEA Japan, Inc.) at a dose of 50 mg/kg/day. At 0.5, 1, 2, 4 and 6 hours after completion of the oral administration, blood was collected from the facial vein over time, so as to obtain plasma. The concentration of the compound in the obtained plasma was measured by LC-MS/MS, and the oral absorbability of the present compound was evaluated.

The results are shown in the following Table 4.

TABLE 4

| Example No. | AUC 0-6 hr (μM · hr) |
|---|---|
| 1 | 50 |
| 2 | 15 |
| 3 | 24 |
| 4 | 12 |
| 5 | 20 |
| 6 | 17 |
| 7 | 15 |

TABLE 4-continued

| Example No. | AUC 0-6 hr (μM · hr) |
|---|---|
| 8 | 15 |
| 9 | 51 |
| 10 | 50 |
| 11 | 31 |
| 12 | 36 |
| 13 | 18 |
| 14 | 27 |
| 15 | 34 |
| 16 | 15 |
| 17 | 21 |
| 18 | 15 |
| 19 | 6.1 |
| Comp. Ex. 2 | 1.5 |

From the above results, it was found that the compound of the present invention was contained in a sufficient concentration in the plasma, so that the present compound exhibited favorable oral absorbability. In contrast, the compound of Comparative Example 2 had oral absorbability that was more than 4 times more attenuated than the compound of the present invention.

Test Example 7 Evaluation of Brain Penetration Properties

The compound of the present invention was suspended or dissolved in 0.5% HPMC aqueous solution and 0.1 N hydrochloric acid, and the obtained suspension or solution was orally administered to BALB/cA mice (CLEA Japan, Inc.) at a dose of 50 mg/kg/day. At 0.5 hours after completion of the oral administration, blood was collected from the facial vein, and whole brain was then excised, so as to obtain plasma and brain samples. Water was added to the obtained brain sample in 3 times the volume of the brain sample, and the resultant was then homogenized using an ultrasonic homogenizer, so as to obtain a brain homogenate. The concentration of the compound in the obtained plasma and brain homogenate was measured by LC-MS/MS, and the brain penetration properties of the present compound were evaluated from the brain/plasma concentration of the compound.

The results are shown in the following Table 5.

TABLE 5

| Example No. | Compound concentration in plasma (μM) | Compound concentration in brain (μM) | Kp value (Compound concentration in brain/plasma) |
|---|---|---|---|
| 1 | 9.1 | 1.4 | 0.15 |
| 2 | 6.6 | 1.8 | 0.27 |
| 3 | 11 | 1.4 | 0.13 |
| 4 | 8.3 | 2.8 | 0.34 |
| 5 | 15 | 2.2 | 0.15 |
| 6 | 7.5 | 1.3 | 0.17 |
| 7 | 7.9 | 1.1 | 0.14 |
| 8 | 9.9 | 3.3 | 0.33 |
| 9 | 13 | 2.4 | 0.18 |
| 10 | 13 | 2.4 | 0.18 |
| 11 | 12 | 2.7 | 0.23 |
| 12 | 11 | 3.2 | 0.29 |
| 13 | 13 | 2.8 | 0.22 |
| 14 | 9.9 | 2.1 | 0.21 |
| 15 | 8.1 | 1.2 | 0.15 |
| 16 | 12 | 4.4 | 0.35 |
| 17 | 17 | 6.5 | 0.39 |
| 18 | 7.7 | 1.6 | 0.22 |
| 19 | 4.9 | 0.7 | 0.14 |
| Comp. Ex. 2 | 1.6 | 0.008 | 0.005 |

From the above results, it was found that the compound of the present invention had a high brain/plasma compound concentration (Kp value) and thus, exhibited favorable brain penetration properties. On the other hand, the brain concentration of the compound of Comparative Example 2 was more than 80 times more attenuated than that of the compound of the present invention.

Test Example 8 Antitumor Effect Confirmation Test (In Vivo) on Direct Brain Transplantation Models, into which Luciferase Gene-Introduced HER2 Expressing Cell Line (NCI-N87-Luc) is Directly Transplanted In order to confirm the antitumor effects of a test compound on direct brain transplantation models, NCI-N87-Luc, which was obtained by introducing a luciferase gene into NCI-N87 that was a human stomach cancer tumor cell line purchased from American Type Culture Collection, was used. The NCI-N87-Luc was added into a 10% fetal bovine serum (FBS)-containing RPMI-1640 medium (supplemented with 4.5 g/L glucose, 10 mM HEPES, and 1 mM sodium pyruvate) (Wako Pure Chemical Industries, Ltd.), and this cell line was then cultured in a 5% CO2 incubator at 37° C.

The NCI-N87-Luc cells were re-suspended in PBS in a concentration of $6.25 \times 10^7$ cells/mL.

Using a mouse ear bar, a nude mouse with 6 to 7 weeks old (BALB/cAJcl-nu/nu, CLEA Japan, Inc.) was fixed in a brain stereotaxic apparatus, and the skin on the upper brain portion was disinfected with alcohol cotton and was then excised with a surgical knife.

A microdrill was used to drill a hole in the skull, and then, using a needle, a manipulator, and a syringe pump, 4 µL of the cell suspension was transplanted into the brain at a rate of 0.8 µL/min.

As a reference of the amount of brain tumor, approximately 3 weeks after the transplantation, Total Flux (Photon/sec) was measured in all of the survival cases, using IVIS (PerkinElmer, Inc., model: Lumina II). Based on the obtained results, 6 animals were assigned to each group, using the grouping program of MiSTAT (Ver. 2.00).

The test compound was orally administered to the mice once a day, every day, for 21 days from the following day of the grouping (Days 1-21).

For judgment of the presence or absence of effects, the value (Log 10) obtained by logarithmic transformation of the total flux on the judgment date was used. The test compound was administered to the mice at a dose of 25 mg/kg/day in Example 2 and Example 11, whereas it was administered at a dose of 50 mg/kg/day in Example 12.

A graph was prepared with the value obtained by logarithmic transformation (Log 10) of the average total flux of each group as a vertical axis, and with the number of days (Day) after the transplantation as a horizontal axis. The transition of the total flux over time in the drug administration period was observed.

As test compounds, the compounds of Example 2, Example 11, and Example 12 were used, and as a control, 0.1 N HCl and 0.5% HPMC aqueous solution were used.

The results are shown in the following FIG. 1 to FIG. 3. The value obtained by logarithmic transformation (Log 10) of the total flux on Day 22 in each group was analyzed by a Dunnett test or a Student-t test. As a result, it was demonstrated that the aforementioned value of the test compound group was statistically significantly lower than the value of the control group (significance level (both sides): 5%) (FIG. 1: the compound of Example 2 was used, P=0.0077; FIG. 2: the compound of Example 11 was used, P=0.0007; and FIG. 3: the compound of Example 12 was used, P=0.0012). For the measurement of the body weight, an animal electronic balance was used. A body weight change percentage (BWCn) from the body weight on the $n^{th}$ day (BWn) was calculated according to the following equation:

$$BWCn\ (\%) = [(\text{body weight on } n^{th} \text{ day}) - (\text{body weight on grouping day})] / [(\text{body weight on grouping day})] \times 100.$$

From the results of this test, it was found that the compound of the present invention has excellent antitumor effects against the HER2 overexpressing cell line (NCI-N87-luc) transplanted into the nude mice. Moreover, a body weight reduction of −20% or more was not observed in all of the mice to which the compound of Example 2 or Example 11 had been administered. Accordingly, it was found that there were no serious side effects.

It is to be noted that all documents and publications cited in the present description are incorporated herein by reference in their entirety, regardless of the purpose thereof. Moreover, the present description includes the contents disclosed in the claims, specification and drawings of Japanese Patent Application No. 2019-003403 (filed on Jan. 11, 2019), from which the present application claims priority.

Several embodiments of the present invention are described above. However, these embodiments are provided for illustrative purpose only, and thus, are not intended to limit the scope of the present invention. These novel embodiments can be carried out in various other forms, and various abbreviations, substitutions and alternations can be carried out, unless they are deviated from the spirit of the invention. These embodiments and the modifications thereof are included in the scope or spirit of the invention, and are also included in the invention according to the claims and the scope equivalent thereto.

The invention claimed is:
1. A compound represented by formula (I):

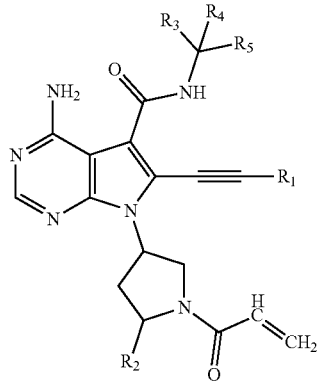

or a pharmaceutically acceptable salt, stereoisomer, or tautomer thereof,
wherein:
- $R_1$ represents $C_1$-$C_4$ alkyl or $C_3$-$C_4$ cycloalkyl, wherein the $C_1$-$C_4$ alkyl is optionally substituted with 1 $OC_1$—$C_4$ alkyl substituent;
- $R_2$ represents hydrogen, halogen, $C_1$-$C_6$ alkyl, or $OC_1$—$C_6$ alkyl, wherein the $C_1$-$C_6$ alkyl is optionally substituted with 1, 2, 3, 4, or 5 substituents independently selected from the group consisting of fluoro and $OC_1$—$C_4$ alkyl;
- $R_3$ represents hydrogen or $C_1$-$C_4$ alkyl, wherein the $C_1$-$C_4$ alkyl is optionally substituted with 1, 2, 3, 4, or 5 fluoro substituents;
- $R_4$ represents hydrogen or $C_1$-$C_4$ alkyl; and
- $R_5$ represents phenyl, wherein the phenyl is optionally substituted with 1, 2, or 3 substituents independently selected from the group consisting of fluoro and chloro.

2. The compound according to claim 1, or a stereoisomer thereof, wherein the compound, or stereoisomer thereof, is represented by formula (II):

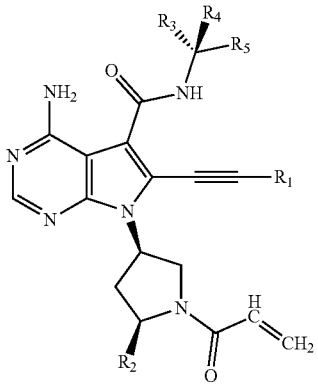

or a pharmaceutically acceptable salt or tautomer thereof.

3. The compound according to claim 1, or a pharmaceutically acceptable salt, stereoisomer, or tautomer thereof, wherein $R_1$ represents methyl, tert-butyl, or cyclopropyl.

4. The compound according to claim 1, or a pharmaceutically acceptable salt, stereoisomer, or tautomer thereof, wherein $R_2$ represents $C_1$-$C_6$ alkyl, wherein the $C_1$-$C_6$ alkyl is optionally substituted with 1, 2, 3, 4, or 5 independently selected $OC_1$—$C_4$ alkyl substituents.

5. The compound according to claim 1, or a pharmaceutically acceptable salt, stereoisomer, or tautomer thereof, wherein $R_2$ represents methyl, ethyl, methoxymethyl, or ethoxymethyl.

6. The compound according to claim 1, or a pharmaceutically acceptable salt, stereoisomer, or tautomer thereof, wherein $R_3$ represents $C_1$-$C_4$ alkyl, wherein the $C_1$-$C_4$ alkyl is optionally substituted with 1, 2, 3, 4, or 5 fluoro substituents.

7. The compound according to claim 1, or a pharmaceutically acceptable salt, stereoisomer, or tautomer thereof, wherein $R_3$ represents methyl.

8. The compound according to claim 1, or a pharmaceutically acceptable salt, stereoisomer, or tautomer thereof, wherein $R_4$ represents hydrogen.

9. The compound according to claim 1, or a pharmaceutically acceptable salt, stereoisomer, or tautomer thereof, wherein $R_5$ represents phenyl, wherein the phenyl is optionally substituted with 1 or 2 substituents independently selected from the group consisting of fluoro and chloro.

10. The compound according to claim 1, or a pharmaceutically acceptable salt, stereoisomer, or tautomer thereof, wherein $R_5$ represents phenyl.

11. The compound according to claim 1, or a stereoisomer thereof, wherein the compound, or stereoisomer thereof, is selected from the group consisting of:

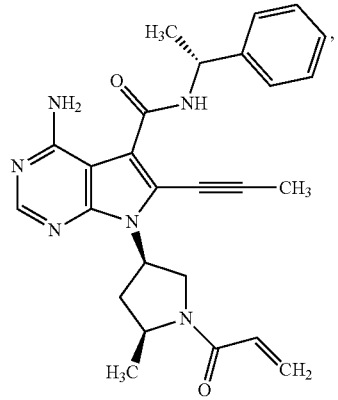 [SMILES: C=CC(=O)N1C[C@H](n2c(C#CC)c(C(=O)N[C@H](C)c3ccccc3)c3c(N)ncnc32)C[C@@H]1C]

-continued

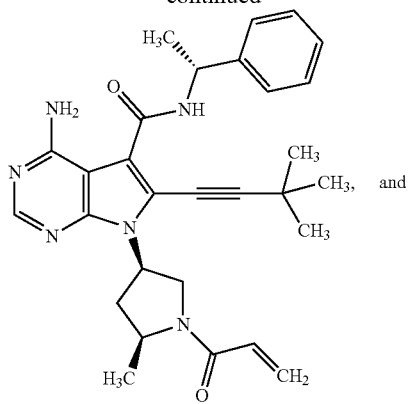

and

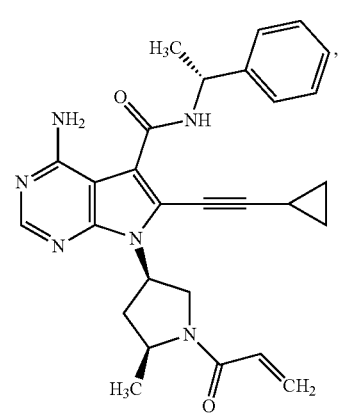

or a pharmaceutically acceptable salt or tautomer thereof.

12. A pharmaceutical composition comprising a pharmaceutically acceptable carrier and the compound according to claim 1, or a pharmaceutically acceptable salt, stereoisomer, or tautomer thereof.

13. The pharmaceutical composition according to claim 12, wherein the pharmaceutical composition is formulated for oral administration.

14. A method for treating a tumor in a subject, comprising administering to a subject in need thereof a therapeutically effective amount of the compound according to claim 1, or a pharmaceutically acceptable salt, stereoisomer, or tautomer thereof.

15. A method for treating a tumor in a subject, comprising administering to a subject in need thereof a therapeutically effective amount of the compound, or a stereoisomer thereof, according to claim 2, or a pharmaceutically acceptable salt or tautomer thereof.

16. A method for treating a tumor in a subject, comprising orally administering to a subject in need thereof a therapeutically effective amount of the compound according to claim 1, or a pharmaceutically acceptable salt, stereoisomer, or tautomer thereof.

17. The compound:

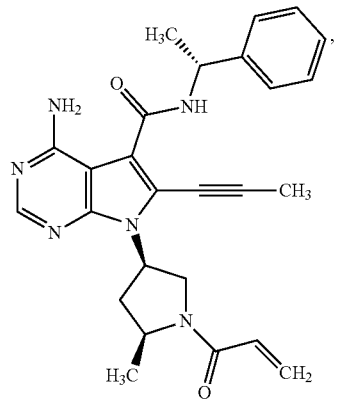

or a pharmaceutically acceptable salt or tautomer thereof.

18. The compound:

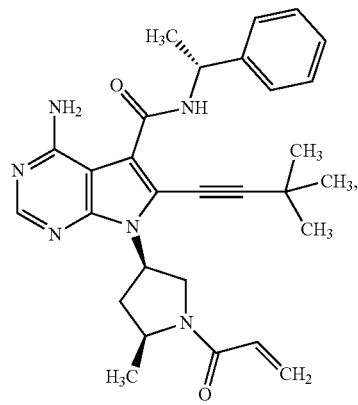 [SMILES: C=CC(=O)N1C[C@H](n2c(C#CC(C)(C)C)c(C(=O)N[C@H](C)c3ccccc3)c3c(N)ncnc32)C[C@@H]1C]

or a pharmaceutically acceptable salt or tautomer thereof.

19. The compound:

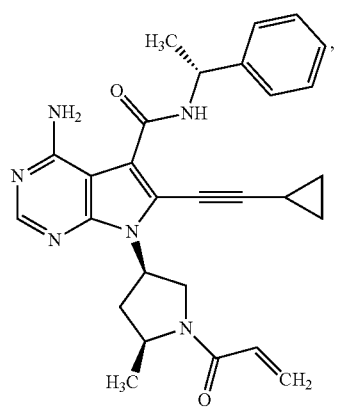 [SMILES: C=CC(=O)N1C[C@H](n2c(C#CC3CC3)c(C(=O)N[C@H](C)c3ccccc3)c3c(N)ncnc32)C[C@@H]1C]

or a pharmaceutically acceptable salt or tautomer thereof.

* * * * *

SEQUENCE LISTING

<160> NUMBER OF SEQ ID NOS: 7

<210> SEQ ID NO 1
<211> LENGTH: 4664
<212> TYPE: DNA
<213> ORGANISM: Homo sapiens

<400> SEQUENCE: 1
gcttgctccc aatcacagga gaaggaggag gtggaggagg agggctgctt gaggaagtat    60

| | |
|---|---|
| aagaatgaag ttgtgaagct gagattcccc tccattggga ccggagaaac caggggagcc | 120 |
| ccccgggcag ccgcgcgccc cttcccacgg ggcccttac tgcgccgcgc gcccggcccc | 180 |
| caccccctcgc agcaccccgc gccccgcgcc ctcccagccg ggtccagccg gagccatggg | 240 |
| gccggagccg cagtgagcac catggagctg gcggccttgt gccgctgggg gctcctcctc | 300 |
| gccctcttgc cccccggagc cgcgagcacc caagtgtgca ccggcacaga catgaagctg | 360 |
| cggctccctg ccagtcccga gacccacctg gacatgctcc gccacctcta ccagggctgc | 420 |
| caggtggtgc agggaaacct ggaactcacc tacctgccca ccaatgccag cctgtccttc | 480 |
| ctgcaggata tccaggaggt gcagggctac gtgctcatcg ctcacaacca agtgaggcag | 540 |
| gtcccactgc agaggctgcg gattgtgcga ggcacccagc tctttgagga caactatgcc | 600 |
| ctggccgtgc tagacaatgg agacccgctg aacaatacca cccctgtcac aggggcctcc | 660 |
| ccaggaggcc tgcgggagct gcagcttcga agcctcacag agatcttgaa aggagggggtc | 720 |
| ttgatccagc ggaaccccca gctctgctac caggacacga ttttgtggaa ggacatcttc | 780 |
| cacaagaaca accagctggc tctcacactg atagacacca accgctctcg ggcctgccac | 840 |
| ccctgttctc cgatgtgtaa gggctcccgc tgctggggag agagttctga ggattgtcag | 900 |
| agcctgacgg gcactgtctg tgccggtggc tgtgcccgct gcaaggggcc actgcccact | 960 |
| gactgctgcc atgagcagtg tgctgccggc tgcacgggcc ccaagcactc tgactgcctg | 1020 |
| gcctgcctcc acttcaacca cagtggcatc tgtgagctgc actgcccagc cctggtcacc | 1080 |
| tacaacacag acacgtttga gtccatgccc aatcccgagg gccggtatac attcggcgcc | 1140 |
| agctgtgtga ctgcctgtcc ctacaactac ctttctacgg acgtgggatc ctgcacccctc | 1200 |
| gtctgccccc tgcacaacca agaggtgaca gcagaggatg aaacacagcg gtgtgagaag | 1260 |
| tgcagcaagc cctgtgcccg agtgtgctat ggtctgggca tggagcactt gcgagaggtg | 1320 |
| agggcagtta ccagtgccaa tatccaggag tttgctggct gcaagaagat ctttgggagc | 1380 |
| ctggcatttc tgccggagag ctttgatggg acccagcct ccaacactgc cccgctccag | 1440 |
| ccagagcagc tccaagtgtt tgagactctg gaagagatca caggttacct atacatctca | 1500 |
| gcatggccgg acagcctgcc tgacctcagc gtcttccaga acctgcaagt aatccgggga | 1560 |
| cgaattctgc acaatggcgc ctactcgctg accctgcaag ggctgggcat cagctggctg | 1620 |
| gggctgcgct cactgaggga actgggcagt ggactggccc tcatccacca taacacccac | 1680 |
| ctctgcttcg tgcacacggt gccctgggac cagctctttc ggaacccgca ccaagctctg | 1740 |
| ctccacactg ccaaccggcc agaggacgag tgtgtgggcg agggcctggc ctgccaccag | 1800 |
| ctgtgcgccc gagggcactg ctggggtcca gggcccaccc agtgtgtcaa ctgcagccag | 1860 |
| ttccttcggg gccaggagtg cgtggaggaa tgccgagtac tgcagggggct ccccaggag | 1920 |
| tatgtgaatg ccaggcactg ttgccgtgc caccctgagt gtcagcccca gaatggctca | 1980 |
| gtgacctgtt ttggaccgga ggctgaccag tgtgtggcct gtgccactca taaggaccct | 2040 |
| cccttctgcg tggcccgctg ccccagcggt gtgaaacctg acctctccta catgcccatc | 2100 |
| tggaagtttc cagatgagga gggcgcatgc cagccttgcc ccatcaactg caccccactcc | 2160 |
| tgtgtggacc tggatgacaa gggctgcccc gccgagcaga gagccagccc tctgacgtcc | 2220 |
| atcatctctg cggtggttgg cattctgctg gtcgtggtct tggggtggt cttgggatc | 2280 |
| ctcatcaagc gacggcagca gaagatccgg aagtacacga tgcggagact gctgcaggaa | 2340 |
| acggagctgg tggagccgct gacacctagc ggagcgatgc caaccaggc gcagatgcgg | 2400 |
| atcctgaaag agacggagct gaggaaggtg aaggtgcttg gatctggcgc ttttggcaca | 2460 |

```
gtctacaagg gcatctggat ccctgatggg gagaatgtga aaattccagt ggccatcaaa      2520
gtgttgaggg aaaacacatc ccccaaagcc aacaaagaaa tcttagacga agcatacgtg      2580
atggctggtg tgggctcccc atatgtctcc cgccttctgg gcatctgcct gacatccacg      2640
gtgcagctgg tgacacagct tatgccctat ggctgcctct tagaccatgt ccgggaaaac      2700
cgcggacgcc tgggctccca ggacctgctg aactggtgta tgcagattgc caaggggatg      2760
agctacctgg aggatgtgcg gctcgtacac agggacttgg ccgctcggaa cgtgctggtc      2820
aagagtccca accatgtcaa aattacagac ttcgggctgg ctcggctgct ggacattgac      2880
gagacagagt accatgcaga tggggggcaag gtgcccatca gtggatggc gctggagtcc      2940 attctccgcc ggcggttcac ccaccagagt gatgtgtgga gttatggtgt gactgtgtgg      3000
gagctgatga cttttggggc caaaccttac gatgggatcc cagcccggga gatccctgac      3060
ctgctggaaa aggggagcg gctgccccag cccccatct gcaccattga tgtctacatg      3120
atcatggtca aatgttggat gattgactct gaatgtcggc caagattccg ggagttggtg      3180
tctgaattct cccgcatggc cagggacccc cagcgctttg tggtcatcca gaatgaggac      3240
ttgggcccag ccagtccctt ggacagcacc ttctaccgct cactgctgga ggacgatgac      3300 atggggggacc tggtggatgc tgaggagtat ctggtacccc agcagggctt cttctgtcca      3360
gaccctgccc cggcgctgg gggcatggtc caccacaggc accgcagctc atctaccagg      3420
agtggcggtg gggacctgac actagggctg gagccctctg aagaggaggc ccccaggtct      3480
ccactggcac cctccgaagg ggctggctcc gatgtatttg atggtgacct gggaatgggg      3540
gcagccaagg ggctgcaaag cctccccaca catgacccca gccctctaca gcggtacagt      3600
gaggacccca cagtacccct gccctctgag actgatggct acgttgcccc cctgacctgc      3660 agccccagc ctgaatatgt gaaccagcca gatgttcggc cccagccccc ttcgccccga      3720
gagggccctc tgcctgctgc ccgacctgct ggtgccactc tggaaaggcc caagactctc      3780
tccccaggga agaatgggt cgtcaaagac gttttttgcct ttggggggtgc cgtggagaac      3840 cccgagtact tgacacccca gggaggagct gcccctcagc cccacctccc tcctgccttc      3900
agcccagcct tcgacaacct ctattactgg gaccaggacc caccagagcg ggggggctcca      3960 cccagcacct tcaaagggac acctacggca gagaacccag agtacctggg tctggacgtg      4020
ccagtgtgaa ccagaaggcc aagtccgcag aagccctgat gtgtcctcag ggagcaggga      4080
aggcctgact tctgctggca tcaagaggtg gagggccct ccgaccactt ccaggggaac      4140
ctgccatgcc aggaacctgt cctaaggaac cttccttcct gcttgagttc ccagatggct      4200
ggaaggggtc cagcctcgtt ggaagaggaa cagcactggg gagtctttgt ggattctgag      4260
gccctgccca atgagactct agggtccagt ggatgccaca gcccagcttg ccctttcct      4320 tccagatcct gggtactgaa agccttaggg aagctggcct gagagggaa gcggccctaa      4380 gggagtgtct aagaacaaaa gcgacccatt cagagactgt ccctgaaacc tagtactgcc      4440
ccccatgagg aaggaacagc aatggtgtca gtatccaggc tttgtacaga gtgcttttct      4500 gtttagttt tactttttt gttttgtttt tttaaagatg aaataaagac ccaggggggag      4560 aatgggtgtt gtatggggag gcaagtgtgg gggtccttc tccacaccca ctttgtccat      4620
ttgcaaatat attttggaaa acagctaaaa aaaaaaaaaa aaaa                      4664
```

<210> SEQ ID NO 2
<211> LENGTH: 1255
<212> TYPE: PRT

<213> ORGANISM: Homo sapiens

<400> SEQUENCE: 2

```
Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400
```

```
Glu Thr Leu Glu Glu Ile Thr Gly Tyr Leu Tyr Ile Ser Ala Trp Pro
                405                 410                 415
Asp Ser Leu Pro Asp Leu Ser Val Phe Gln Asn Leu Gln Val Ile Arg
            420                 425                 430
Gly Arg Ile Leu His Asn Gly Ala Tyr Ser Leu Thr Leu Gln Gly Leu
        435                 440                 445
Gly Ile Ser Trp Leu Gly Leu Arg Ser Leu Arg Glu Leu Gly Ser Gly
    450                 455                 460
Leu Ala Leu Ile His His Asn Thr His Leu Cys Phe Val His Thr Val
465                 470                 475                 480
Pro Trp Asp Gln Leu Phe Arg Asn Pro His Gln Ala Leu Leu His Thr
                485                 490                 495
Ala Asn Arg Pro Glu Asp Glu Cys Val Gly Glu Gly Leu Ala Cys His
            500                 505                 510
Gln Leu Cys Ala Arg Gly His Cys Trp Gly Pro Gly Pro Thr Gln Cys
        515                 520                 525
Val Asn Cys Ser Gln Phe Leu Arg Gly Gln Glu Cys Val Glu Glu Cys
    530                 535                 540
Arg Val Leu Gln Gly Leu Pro Arg Glu Tyr Val Asn Ala Arg His Cys
545                 550                 555                 560
Leu Pro Cys His Pro Glu Cys Gln Pro Gln Asn Gly Ser Val Thr Cys
                565                 570                 575
Phe Gly Pro Glu Ala Asp Gln Cys Val Ala Cys Ala His Tyr Lys Asp
            580                 585                 590
Pro Pro Phe Cys Val Ala Arg Cys Pro Ser Gly Val Lys Pro Asp Leu
        595                 600                 605
Ser Tyr Met Pro Ile Trp Lys Phe Pro Asp Glu Glu Gly Ala Cys Gln
    610                 615                 620
Pro Cys Pro Ile Asn Cys Thr His Ser Cys Val Asp Leu Asp Asp Lys
625                 630                 635                 640
Gly Cys Pro Ala Glu Gln Arg Ala Ser Pro Leu Thr Ser Ile Ile Ser
                645                 650                 655
Ala Val Val Gly Ile Leu Leu Val Val Val Leu Gly Val Val Phe Gly
            660                 665                 670
Ile Leu Ile Lys Arg Arg Gln Gln Lys Ile Arg Lys Tyr Thr Met Arg
        675                 680                 685
Arg Leu Leu Gln Glu Thr Glu Leu Val Glu Pro Leu Thr Pro Ser Gly
    690                 695                 700
Ala Met Pro Asn Gln Ala Gln Met Arg Ile Leu Lys Glu Thr Glu Leu
705                 710                 715                 720
Arg Lys Val Lys Val Leu Gly Ser Gly Ala Phe Gly Thr Val Tyr Lys
                725                 730                 735
Gly Ile Trp Ile Pro Asp Gly Glu Asn Val Lys Ile Pro Val Ala Ile
            740                 745                 750
Lys Val Leu Arg Glu Asn Thr Ser Pro Lys Ala Asn Lys Glu Ile Leu
        755                 760                 765
Asp Glu Ala Tyr Val Met Ala Gly Val Gly Ser Pro Tyr Val Ser Arg
    770                 775                 780
Leu Leu Gly Ile Cys Leu Thr Ser Thr Val Gln Leu Val Thr Gln Leu
785                 790                 795                 800
Met Pro Tyr Gly Cys Leu Leu Asp His Val Arg Glu Asn Arg Gly Arg
                805                 810                 815
Leu Gly Ser Gln Asp Leu Leu Asn Trp Cys Met Gln Ile Ala Lys Gly
```

-continued

```
                820                 825                 830
Met Ser Tyr Leu Glu Asp Val Arg Leu Val His Arg Asp Leu Ala Ala
                    835                 840                 845
Arg Asn Val Leu Val Lys Ser Pro Asn His Val Lys Ile Thr Asp Phe
    850                 855                 860
Gly Leu Ala Arg Leu Leu Asp Ile Asp Glu Thr Glu Tyr His Ala Asp
865                 870                 875                 880
Gly Gly Lys Val Pro Ile Lys Trp Met Ala Leu Glu Ser Ile Leu Arg
                885                 890                 895
Arg Arg Phe Thr His Gln Ser Asp Val Trp Ser Tyr Gly Val Thr Val
            900                 905                 910
Trp Glu Leu Met Thr Phe Gly Ala Lys Pro Tyr Asp Gly Ile Pro Ala
        915                 920                 925
Arg Glu Ile Pro Asp Leu Leu Glu Lys Gly Arg Leu Pro Gln Pro
    930                 935                 940
Pro Ile Cys Thr Ile Asp Val Tyr Met Ile Met Val Lys Cys Trp Met
945                 950                 955                 960
Ile Asp Ser Glu Cys Arg Pro Arg Phe Arg Glu Leu Val Ser Glu Phe
                965                 970                 975
Ser Arg Met Ala Arg Asp Pro Gln Arg Phe Val Val Ile Gln Asn Glu
            980                 985                 990
Asp Leu Gly Pro Ala Ser Pro Leu Asp Ser Thr Phe Tyr Arg Ser Leu
            995                 1000                1005
Leu Glu Asp Asp Asp Met Gly Asp Leu Val Asp Ala Glu Glu Tyr
    1010                1015                1020
Leu Val Pro Gln Gln Gly Phe Phe Cys Pro Asp Pro Ala Pro Gly
    1025                1030                1035
Ala Gly Gly Met Val His His Arg His Arg Ser Ser Ser Thr Arg
    1040                1045                1050
Ser Gly Gly Gly Asp Leu Thr Leu Gly Leu Glu Pro Ser Glu Glu
    1055                1060                1065
Glu Ala Pro Arg Ser Pro Leu Ala Pro Ser Glu Gly Ala Gly Ser
    1070                1075                1080
Asp Val Phe Asp Gly Asp Leu Gly Met Gly Ala Ala Lys Gly Leu
    1085                1090                1095
Gln Ser Leu Pro Thr His Asp Pro Ser Pro Leu Gln Arg Tyr Ser
    1100                1105                1110
Glu Asp Pro Thr Val Pro Leu Pro Ser Glu Thr Asp Gly Tyr Val
    1115                1120                1125
Ala Pro Leu Thr Cys Ser Pro Gln Pro Glu Tyr Val Asn Gln Pro
    1130                1135                1140
Asp Val Arg Pro Gln Pro Pro Ser Pro Arg Glu Gly Pro Leu Pro
    1145                1150                1155
Ala Ala Arg Pro Ala Gly Ala Thr Leu Glu Arg Pro Lys Thr Leu
    1160                1165                1170
Ser Pro Gly Lys Asn Gly Val Val Lys Asp Val Phe Ala Phe Gly
    1175                1180                1185
Gly Ala Val Glu Asn Pro Glu Tyr Leu Thr Pro Gln Gly Gly Ala
    1190                1195                1200
Ala Pro Gln Pro His Pro Pro Pro Ala Phe Ser Pro Ala Phe Asp
    1205                1210                1215
Asn Leu Tyr Tyr Trp Asp Gln Asp Pro Pro Glu Arg Gly Ala Pro
    1220                1225                1230
```

Pro Ser Thr Phe Lys Gly Thr Pro Thr Ala Glu Asn Pro Glu Tyr
   1235                1240                1245

Leu Gly Leu Asp Val Pro Val
   1250                1255

<210> SEQ ID NO 3
<211> LENGTH: 4940
<212> TYPE: DNA
<213> ORGANISM: Homo sapiens

<400> SEQUENCE: 3

| | | | | | |
|---|---|---|---|---|---|
| aagttcctgt | gttctttatt | ctactctccg | ctgaagtcca | cacagtttaa | attaaagttc | 60 |
| ccggattttt | gtgggcgcct | gccccgcccc | tcgtccccct | gctgtgtcca | tatatcgagg | 120 |
| cgatagggtt | aagggaaggc | ggacgcctga | tgggttaatg | agcaaactga | agtgttttcc | 180 |
| atgatctttt | ttgagtcgca | attgaagtac | cacctcccga | gggtgattgc | ttccccatgc | 240 |
| ggggtagaac | ctttgctgtc | ctgttcacca | ctctacctcc | agcacagaat | ttggcttatg | 300 |
| cctactcaat | gtgaagatga | tgaggatgaa | aacctttgtg | atgatccact | tccacttaat | 360 |
| gaatggtggc | aaagcaaagc | tatattcaag | accacatgca | aagctactcc | ctgagcaaag | 420 |
| agtcacagat | aaaacggggg | caccagtaga | atggccagga | caaacgcagt | gcagcacaga | 480 |
| gactcagacc | ctggcagcca | tgcctgcgca | ggcagtgatg | agagtgacat | gtactgttgt | 540 |
| ggacatgcac | aaaagtgaga | tacttcaaag | attccagaag | atatgccccg | ggggtcctgg | 600 |
| aagccacaag | tgtgcaccgg | cacagacatg | aagctgcggc | tccctgccag | tcccgagacc | 660 |
| cacctggaca | tgctccgcca | cctctaccag | ggctgccagg | tggtgcaggg | aaacctggaa | 720 |
| ctcacctacc | tgcccaccaa | tgccagcctg | tccttcctgc | aggatatcca | ggaggtgcag | 780 |
| ggctacgtgc | tcatcgctca | caaccaagtg | aggcaggtcc | cactgcagag | gctgcggatt | 840 |
| gtgcgaggca | cccagctctt | tgaggacaac | tatgccctgg | ccgtgctaga | caatggagac | 900 |
| ccgctgaaca | ataccacccc | tgtcacaggg | gcctcccag | gaggcctgcg | ggagctgcag | 960 |
| cttcgaagcc | tcacagagat | cttgaaagga | ggggtcttga | tccagcggaa | ccccagctc | 1020 |
| tgctaccagg | acacgatttt | gtggaaggac | atcttccaca | gaacaaccca | gctggctctc | 1080 |
| acactgatag | acaccaaccg | ctctcggggcc | tgccacccct | gttctccgat | gtgtaagggc | 1140 |
| tcccgctgct | ggggagagag | ttctgaggat | tgtcagagcc | tgacgcgcac | tgtctgtgcc | 1200 |
| ggtggctgtg | cccgctgcaa | ggggccactg | cccactgact | gctgccatga | gcagtgtgct | 1260 |
| gccggctgca | cgggccccaa | gcactctgac | tgcctggcct | gcctccactt | caaccacagt | 1320 |
| ggcatctgtg | agctgcactg | cccagccctg | gtcacctaca | acacagacac | gtttgagtcc | 1380 |
| atgcccaatc | ccgagggccg | gtatacattc | ggcgccagct | gtgtgactgc | ctgtccctac | 1440 |
| aactaccttt | ctacggacgt | gggatcctgc | accctcgtct | gccccctgca | caaccaagag | 1500 |
| gtgacagcag | aggatggaac | acagcggtgt | gagaagtgca | gcaagccctg | tgcccgagtg | 1560 |
| tgctatggtc | tgggcatgga | gcacttgcga | gaggtgaggg | cagttaccag | tgccaatatc | 1620 |
| caggagtttg | ctggctgcaa | gaagatcttt | gggagcctgg | catttctgcc | ggagagcttt | 1680 |
| gatgggacc | agcctccaa | cactgccccg | ctccagccaa | agcagctcca | agtgtttgag | 1740 |
| actctggaag | agatcacagg | ttacctatac | atctcagcat | ggccggacag | cctgcctgac | 1800 |
| ctcagcgtct | tccagaacct | gcaagtaatc | cgggacgaa | ttctgcacaa | tggcgcctac | 1860 |
| tcgctgaccc | tgcaagggct | gggcatcagc | tggctggggc | tgcgctcact | gagggaactg | 1920 |

-continued

```
ggcagtggac tggccctcat ccaccataac acccacctct gcttcgtgca cacggtgccc    1980
tgggaccagc tctttcggaa cccgcaccaa gctctgctcc acactgccaa ccggccagag    2040
gacgagtgtg tgggcgaggg cctggcctgc caccagctgt gcgcccgagg gcactgctgg    2100 ggtccaggc ccacccagtg tgtcaactgc agccagttcc ttcggggcca ggagtgcgtg     2160
gaggaatgcc gagtactgca ggggctcccc agggagtatg tgaatgccag gcactgtttg    2220
ccgtgccacc ctgagtgtca gccccagaat ggctcagtga cctgttttgg accggaggct    2280
gaccagtgtg tggcctgtgc ccactataag gaccctccct tctgcgtggc ccgctgcccc    2340
agcggtgtga aacctgacct ctcctacatg cccatctgga gtttccaga tgaggagggc     2400 gcatgccagc cttgccccat caactgcacc cactcctgtg tggacctgga tgacaagggc    2460
tgccccgccg agcagagagc cagccctctg acgtccatca tctctgcggt ggttggcatt    2520
ctgctggtcg tggtcttggg ggtggtcttt gggatcctca tcaagcgacg gcagcagaag    2580
atccggaagt acacgatgcg gagactgctg caggaaacgg agctggtgga gccgctgaca    2640
cctagcggag cgatgcccaa ccaggcgcag atgcggatcc tgaaagagac ggagctgagg    2700
aaggtgaagg tgcttggatc tggcgctttt ggcacagtct acaagggcat ctggatccct    2760
gatggggaga atgtgaaaat tccagtggcc atcaaagtgt tgagggaaaa cacatccccc    2820
aaagccaaca agaaatcttt agacgaagca tacgtgatgg ctggtgtggg ctccccatat    2880
gtctcccgcc ttctgggcat ctgcctgaca tccacggtgc agctggtgac acagcttatg    2940
ccctatggct gcctcttaga ccatgtccgg gaaaaccgcg gacgcctggg ctcccaggac    3000
ctgctgaact ggtgtatgca gattgccaag gggatgagct acctggagga tgtgcggctc    3060
gtacacaggg acttggccgc tcggaacgtg ctggtcaaga gtcccaacca tgtcaaaatt    3120
acagacttcg gcctggctcg gctgctggac attgacgaga cagagtacca tgcagatggg    3180
ggcaaggtgc ccatcaagtg gatggcgctg gagtccattc tccgccggcg gttcacccac    3240
cagagtgatg tgtggagtta tggtgtgact gtgtgggagc tgatgacttt tggggccaaa    3300
ccttacgatg ggatcccagc ccgggagatc cctgacctgc tggaaaaggg ggagcggctg    3360
ccccagcccc ccatctgcac cattgatgtc tacatgatca tggtcaaatg ttggatgatt    3420
gactctgaat gtcggccaag attccgggag ttggtgtctg aattctcccg catggccagg    3480 gaccccagc gctttgtggt catccagaat gaggacttgg gcccagccag tcccttggac    3540
agcaccttct accgctcact gctggaggac gatgacatgg gggacctggt ggatgctgag    3600
gagtatctgg tacccagca gggcttcttc tgtccagacc ctgcccccgg cgctgggggc    3660
atggtccacc acaggcaccg cagctcatct accaggagtg gcggtgggga cctgacacta    3720
gggctggagc cctctgaaga ggaggccccc aggtctccac tggcaccctc cgaagggggct    3780 ggctccgatg tatttgatgg tgacctggga atgggggcag ccaaggggct gcaaagcctc    3840
cccacacatg accccagccc tctacagcgg tacagtgagg accccacagt acccctgccc    3900
tctgagactg atggctacgt tgccccccctg acctgcagcc cccagcctga atatgtgaac    3960
cagccagatg ttcggccccca gcccccttcg ccccgagagg gccctctgcc tgctgcccga    4020
cctgctggtg ccactctgga aaggcccaag actctctccc cagggaagaa tggggtcgtc    4080
aaagacgttt ttgcctttgg gggtgccgtg gagaacccccg agtacttgac ccccaggga    4140 ggagctgccc ctcagcccca ccctcctcct gccttcagcc cagccttcga caacctctat    4200
tactgggacc aggacccacc agagcggggg gctccaccca gcaccttcaa agggacacct    4260
acggcagaga acccagagta cctgggtctg gacgtgccag tgtgaaccag aaggccaagt    4320
```

-continued

```
ccgcagaagc cctgatgtgt cctcagggag cagggaaggc ctgacttctg ctggcatcaa    4380
gaggtgggag ggccctccga ccacttccag gggaacctgc catgccagga acctgtccta    4440
aggaaccttc cttcctgctt gagttccag atggctggaa ggggtccagc ctcgttggaa     4500
gaggaacagc actggggagt ctttgtggat tctgaggccc tgcccaatga gactctaggg    4560
tccagtggat gccacagccc agcttggccc tttccttcca gatcctgggt actgaaagcc    4620
ttagggaagc tggcctgaga ggggaagcgg ccctaaggga gtgtctaaga acaaaagcga    4680
cccattcaga gactgtccct gaaacctagt actgccccc atgaggaagg aacagcaatg     4740
gtgtcagtat ccaggctttg tacagagtgc ttttctgttt agtttttact ttttttgttt    4800
tgttttttta agatgaaat aaagacccag ggggagaatg ggtgttgtat ggggaggcaa     4860
gtgtgggggg tccttctcca cacccacttt gtccatttgc aaatatattt tggaaaacag    4920
ctaaaaaaaa aaaaaaaaa                                                 4940
```

<210> SEQ ID NO 4
<211> LENGTH: 1240
<212> TYPE: PRT
<213> ORGANISM: Homo sapiens

<400> SEQUENCE: 4

```
Met Pro Arg Gly Ser Trp Lys Pro Gln Val Cys Thr Gly Thr Asp Met
1               5                   10                  15

Lys Leu Arg Leu Pro Ala Ser Pro Glu Thr His Leu Asp Met Leu Arg
            20                  25                  30

His Leu Tyr Gln Gly Cys Gln Val Val Gln Gly Asn Leu Glu Leu Thr
        35                  40                  45

Tyr Leu Pro Thr Asn Ala Ser Leu Ser Phe Leu Gln Asp Ile Gln Glu
    50                  55                  60

Val Gln Gly Tyr Val Leu Ile Ala His Asn Gln Val Arg Gln Val Pro
65                  70                  75                  80

Leu Gln Arg Leu Arg Ile Val Arg Gly Thr Gln Leu Phe Glu Asp Asn
                85                  90                  95

Tyr Ala Leu Ala Val Leu Asp Asn Gly Asp Pro Leu Asn Asn Thr Thr
            100                 105                 110

Pro Val Thr Gly Ala Ser Pro Gly Gly Leu Arg Glu Leu Gln Leu Arg
        115                 120                 125

Ser Leu Thr Glu Ile Leu Lys Gly Gly Val Leu Ile Gln Arg Asn Pro
    130                 135                 140

Gln Leu Cys Tyr Gln Asp Thr Ile Leu Trp Lys Asp Ile Phe His Lys
145                 150                 155                 160

Asn Asn Gln Leu Ala Leu Thr Leu Ile Asp Thr Asn Arg Ser Arg Ala
                165                 170                 175

Cys His Pro Cys Ser Pro Met Cys Lys Gly Ser Arg Cys Trp Gly Glu
            180                 185                 190

Ser Ser Glu Asp Cys Gln Ser Leu Thr Arg Thr Val Cys Ala Gly Gly
        195                 200                 205

Cys Ala Arg Cys Lys Gly Pro Leu Pro Thr Asp Cys Cys His Glu Gln
    210                 215                 220

Cys Ala Ala Gly Cys Thr Gly Pro Lys His Ser Asp Cys Leu Ala Cys
225                 230                 235                 240

Leu His Phe Asn His Ser Gly Ile Cys Glu Leu His Cys Pro Ala Leu
                245                 250                 255
```

-continued

```
Val Thr Tyr Asn Thr Asp Thr Phe Glu Ser Met Pro Asn Pro Glu Gly
            260                 265                 270

Arg Tyr Thr Phe Gly Ala Ser Cys Val Thr Ala Cys Pro Tyr Asn Tyr
        275                 280                 285

Leu Ser Thr Asp Val Gly Ser Cys Thr Leu Val Cys Pro Leu His Asn
    290                 295                 300

Gln Glu Val Thr Ala Glu Asp Gly Thr Gln Arg Cys Glu Lys Cys Ser
305                 310                 315                 320

Lys Pro Cys Ala Arg Val Cys Tyr Gly Leu Gly Met Glu His Leu Arg
                325                 330                 335

Glu Val Arg Ala Val Thr Ser Ala Asn Ile Gln Glu Phe Ala Gly Cys
            340                 345                 350

Lys Lys Ile Phe Gly Ser Leu Ala Phe Leu Pro Glu Ser Phe Asp Gly
        355                 360                 365

Asp Pro Ala Ser Asn Thr Ala Pro Leu Gln Pro Glu Gln Leu Gln Val
    370                 375                 380

Phe Glu Thr Leu Glu Glu Ile Thr Gly Tyr Leu Tyr Ile Ser Ala Trp
385                 390                 395                 400

Pro Asp Ser Leu Pro Asp Leu Ser Val Phe Gln Asn Leu Gln Val Ile
                405                 410                 415

Arg Gly Arg Ile Leu His Asn Gly Ala Tyr Ser Leu Thr Leu Gln Gly
            420                 425                 430

Leu Gly Ile Ser Trp Leu Gly Leu Arg Ser Leu Arg Glu Leu Gly Ser
        435                 440                 445

Gly Leu Ala Leu Ile His His Asn Thr His Leu Cys Phe Val His Thr
    450                 455                 460

Val Pro Trp Asp Gln Leu Phe Arg Asn Pro His Gln Ala Leu Leu His
465                 470                 475                 480

Thr Ala Asn Arg Pro Glu Asp Glu Cys Val Gly Glu Gly Leu Ala Cys
                485                 490                 495

His Gln Leu Cys Ala Arg Gly His Cys Trp Gly Pro Gly Pro Thr Gln
            500                 505                 510

Cys Val Asn Cys Ser Gln Phe Leu Arg Gly Gln Glu Cys Val Glu Glu
        515                 520                 525

Cys Arg Val Leu Gln Gly Leu Pro Arg Glu Tyr Val Asn Ala Arg His
530                 535                 540

Cys Leu Pro Cys His Pro Glu Cys Gln Pro Gln Asn Gly Ser Val Thr
545                 550                 555                 560

Cys Phe Gly Pro Glu Ala Asp Gln Cys Val Ala Cys Ala His Tyr Lys
                565                 570                 575

Asp Pro Pro Phe Cys Val Ala Arg Cys Pro Ser Gly Val Lys Pro Asp
            580                 585                 590

Leu Ser Tyr Met Pro Ile Trp Lys Phe Pro Asp Glu Glu Gly Ala Cys
        595                 600                 605

Gln Pro Cys Pro Ile Asn Cys Thr His Ser Cys Val Asp Leu Asp Asp
    610                 615                 620

Lys Gly Cys Pro Ala Glu Gln Arg Ala Ser Pro Leu Thr Ser Ile Ile
625                 630                 635                 640

Ser Ala Val Val Gly Ile Leu Leu Val Val Leu Gly Val Val Phe
                645                 650                 655

Gly Ile Leu Ile Lys Arg Arg Gln Gln Lys Ile Arg Lys Tyr Thr Met
            660                 665                 670

Arg Arg Leu Leu Gln Glu Thr Glu Leu Val Glu Pro Leu Thr Pro Ser
```

```
              675                 680                 685
Gly Ala Met Pro Asn Gln Ala Gln Met Arg Ile Leu Lys Glu Thr Glu
        690                 695                 700
Leu Arg Lys Val Lys Val Leu Gly Ser Gly Ala Phe Gly Thr Val Tyr
705                 710                 715                 720
Lys Gly Ile Trp Ile Pro Asp Gly Glu Asn Val Lys Ile Pro Val Ala
                725                 730                 735
Ile Lys Val Leu Arg Glu Asn Thr Ser Pro Lys Ala Asn Lys Glu Ile
            740                 745                 750
Leu Asp Glu Ala Tyr Val Met Ala Gly Val Gly Ser Pro Tyr Val Ser
        755                 760                 765
Arg Leu Leu Gly Ile Cys Leu Thr Ser Thr Val Gln Leu Val Thr Gln
    770                 775                 780
Leu Met Pro Tyr Gly Cys Leu Leu Asp His Val Arg Glu Asn Arg Gly
785                 790                 795                 800
Arg Leu Gly Ser Gln Asp Leu Leu Asn Trp Cys Met Gln Ile Ala Lys
                805                 810                 815
Gly Met Ser Tyr Leu Glu Asp Val Arg Leu Val His Arg Asp Leu Ala
            820                 825                 830
Ala Arg Asn Val Leu Val Lys Ser Pro Asn His Val Lys Ile Thr Asp
        835                 840                 845
Phe Gly Leu Ala Arg Leu Leu Asp Ile Asp Glu Thr Glu Tyr His Ala
    850                 855                 860
Asp Gly Gly Lys Val Pro Ile Lys Trp Met Ala Leu Glu Ser Ile Leu
865                 870                 875                 880
Arg Arg Arg Phe Thr His Gln Ser Asp Val Trp Ser Tyr Gly Val Thr
                885                 890                 895
Val Trp Glu Leu Met Thr Phe Gly Ala Lys Pro Tyr Asp Gly Ile Pro
            900                 905                 910
Ala Arg Glu Ile Pro Asp Leu Leu Glu Lys Gly Glu Arg Leu Pro Gln
        915                 920                 925
Pro Pro Ile Cys Thr Ile Asp Val Tyr Met Ile Met Val Lys Cys Trp
    930                 935                 940
Met Ile Asp Ser Glu Cys Arg Pro Arg Phe Arg Glu Leu Val Ser Glu
945                 950                 955                 960
Phe Ser Arg Met Ala Arg Asp Pro Gln Arg Phe Val Val Ile Gln Asn
                965                 970                 975
Glu Asp Leu Gly Pro Ala Ser Pro Leu Asp Ser Thr Phe Tyr Arg Ser
            980                 985                 990
Leu Leu Glu Asp Asp Asp Met Gly Asp Leu Val Asp Ala Glu Glu Tyr
        995                 1000                1005
Leu Val Pro Gln Gln Gly Phe Phe Cys Pro Asp Pro Ala Pro Gly
    1010                1015                1020
Ala Gly Gly Met Val His His Arg His Arg Ser Ser Ser Thr Arg
    1025                1030                1035
Ser Gly Gly Gly Asp Leu Thr Leu Gly Leu Glu Pro Ser Glu Glu
    1040                1045                1050
Glu Ala Pro Arg Ser Pro Leu Ala Pro Ser Glu Gly Ala Gly Ser
    1055                1060                1065
Asp Val Phe Asp Gly Asp Leu Gly Met Gly Ala Ala Lys Gly Leu
    1070                1075                1080
Gln Ser Leu Pro Thr His Asp Pro Ser Pro Leu Gln Arg Tyr Ser
    1085                1090                1095
```

```
Glu  Asp  Pro  Thr  Val  Pro  Leu  Pro  Ser  Glu  Thr  Asp  Gly  Tyr  Val
     1100                1105                1110

Ala  Pro  Leu  Thr  Cys  Ser  Pro  Gln  Pro  Glu  Tyr  Val  Asn  Gln  Pro
     1115                1120                1125

Asp  Val  Arg  Pro  Gln  Pro  Pro  Ser  Pro  Arg  Glu  Gly  Pro  Leu  Pro
     1130                1135                1140

Ala  Ala  Arg  Pro  Ala  Gly  Ala  Thr  Leu  Glu  Arg  Pro  Lys  Thr  Leu
     1145                1150                1155

Ser  Pro  Gly  Lys  Asn  Gly  Val  Val  Lys  Asp  Val  Phe  Ala  Phe  Gly
     1160                1165                1170

Gly  Ala  Val  Glu  Asn  Pro  Glu  Tyr  Leu  Thr  Pro  Gln  Gly  Gly  Ala
     1175                1180                1185

Ala  Pro  Gln  Pro  His  Pro  Pro  Pro  Ala  Phe  Ser  Pro  Ala  Phe  Asp
     1190                1195                1200

Asn  Leu  Tyr  Tyr  Trp  Asp  Gln  Asp  Pro  Pro  Glu  Arg  Gly  Ala  Pro
     1205                1210                1215

Pro  Ser  Thr  Phe  Lys  Gly  Thr  Pro  Thr  Ala  Glu  Asn  Pro  Glu  Tyr
     1220                1225                1230

Leu  Gly  Leu  Asp  Val  Pro  Val
     1235                1240

<210> SEQ ID NO 5
<211> LENGTH: 4889
<212> TYPE: DNA
<213> ORGANISM: Homo sapiens

<400> SEQUENCE: 5
aagttcctgt gttctttatt ctactctccg ctgaagtcca cacagtttaa attaaagttc    60
ccggattttt gtgggcgcct gccccgcccc tcgtccccct gctgtgtcca tatatcgagg   120
cgatagggtt aagggaaggc ggacgcctga tgggttaatg agcaaactga agtgttttcc   180
atgatctttt ttgagtcgca attgaagtac cacctcccga gggtgattgc ttccccatgc   240
ggggtagaac ctttgctgtc ctgttcacca ctctacctcc agcacagaat ttggcttatg   300
cctactcaat gtgaagatga tgaggatgaa acctttgtg atgatccact tccacttaat    360
gaatggtggc aaagcaaagc tatattcaag accacatgca agctactcc ctgagcaaag    420 agtcacagat aaaacggggg caccagtaga atggccagga caaacgcagt gcagcacaga   480
gactcagacc ctggcagcca tgcctgcgca ggcagtgatg agagtgacat gtactgttgt   540
ggacatgcac aaaagtgagt gtgcaccggc acagacatga agctgcggct ccctgccagt   600
cccgagaccc acctggacat gctccgccac tctaccagg gctgccaggt ggtgcaggga    660
aacctggaac tcacctacct gcccaccaat gccagcctgt ccttcctgca ggatatccag   720
gaggtgcagg gctacgtgct catcgctcac aaccaagtga ggcaggtccc actgcagagg   780
ctgcggattg tgcgaggcac ccagctcttt gaggacaact atgccctggc cgtgctagac   840
aatggagacc cgctgaacaa taccaccct gtcacagggg cctccccagg aggcctgcgg    900
gagctgcagc ttcgaagcct cacagagatc ttgaaaggag gggtcttgat ccagcggaac   960
ccccagctct gctaccagga cacgattttg tggaaggaca tcttccacaa gaacaaccag  1020
ctggctctca cactgataga caccaaccgc tctcgggcct gccaccctg ttctccgatg   1080 tgtaagggct cccgctgctg gggagagagt tctgaggatt gtcagagcct gacgcgcact  1140
gtctgtgccg gtggctgtgc ccgctgcaag gggccactgc ccactgactg ctgccatgag  1200
```

```
cagtgtgctg ccggctgcac gggcccaag cactctgact gcctggcctg cctccacttc    1260
aaccacagtg gcatctgtga gctgcactgc ccagccctgg tcacctacaa cacagacacg    1320
tttgagtcca tgcccaatcc cgagggccgg tatacattcg gcgccagctg tgtgactgcc    1380
tgtccctaca actacctttc tacgacgtg ggatcctgca ccctcgtctg ccccctgcac    1440
aaccaagagg tgacagcaga ggatggaaca cagcggtgtg agaagtgcag caagccctgt    1500
gcccgagtgt gctatggtct gggcatggag cacttgcgag aggtgagggc agttaccagt    1560
gccaatatcc aggagtttgc tggctgcaag aagatctttg ggagcctggc atttctgccg    1620
gagagctttg atggggaccc agcctccaac actgccccgc tccagccaga gcagctccaa    1680
gtgtttgaga ctctggaaga gatcacaggt tacctataca tctcagcatg gccggacagc    1740
ctgcctgacc tcagcgtctt ccagaacctg caagtaatcc ggggacgaat tctgcacaat    1800
ggcgcctact cgctgaccct gcaagggctg gcatcagct ggctgggct gcgctcactg     1860 agggaactgg gcagtggact ggccctcatc caccataaca cccacctctg cttcgtgcac    1920
acggtgccct gggaccagct ctttcggaac ccgcaccaag ctctgctcca cactgccaac    1980
cggccagagg acgagtgtgt gggcgagggc ctggcctgcc accagctgtg cgcccgaggg    2040
cactgctggg gtccagggcc cacccagtgt gtcaactgca gccagttcct tcggggccag    2100
gagtgcgtgg aggaatgccg agtactgcag gggctcccca gggagtatgt gaatgccagg    2160
cactgtttgc cgtgccaccc tgagtgtcag ccccagaatg gctcagtgac ctgtttggga    2220
ccggaggctg accagtgtgt ggcctgtgcc cactataagg accctccctt ctgcgtggcc    2280
cgctgcccca gcggtgtgaa acctgacctc tcctacatgc ccatctggaa gtttccagat    2340
gaggagggcg catgccagcc ttgccccatc aactgcaccc actcctgtgt ggacctggat    2400
gacaagggct gccccgccga gcagagagcc agccctctga cgtccatcat ctctgcggtg    2460
gttggcattc tgctggtcgt ggtcttgggg gtggtctttg ggatcctcat caagcgacgg    2520
cagcagaaga tccggaagta cacgatgcgg agactgctgc aggaaacgga gctggtggag    2580
ccgctgacac ctagcggagc gatgcccaac caggcgcaga tgcggatcct gaaagagacg    2640
gagctgagga aggtgaaggt gcttggatct ggcgcttttg gcacagtcta caagggcatc    2700
tggatccctg atggggagaa tgtgaaaatt ccagtggcca tcaaagtgtt gagggaaaac    2760
acatccccca agccaacaa agaaatctta gacgaagcat acgtgatggc tggtgtgggc    2820
tccccatatg tctcccgcct tctgggcatc tgcctgacat ccacggtgca gctggtgaca    2880
cagcttatgc cctatggctg cctcttagac catgtccggg aaaaccgcgg acgcctgggc    2940
tcccaggacc tgctgaactg gtgtatgcag attgccaagg ggatgagcta cctggaggat    3000
gtgcggctcg tacacaggga cttggccgct cggaacgtgc tggtcaagag tcccaaccat    3060
gtcaaaatta cagacttcgg gctggctcgg ctgctggaca ttgacgagac agagtaccat    3120
gcagatgggg gcaaggtgcc catcaagtgg atggcgctgg agtccattct ccgccggcgg    3180
ttcacccacc agagtgatgt gtggagttat ggtgtgactg tgtgggagct gatgactttt    3240
ggggccaaac cttacgatgg gatcccagcc cgggagatcc ctgacctgct ggaaaagggg    3300
gagcggctgc cccagccccc catctgcacc attgatgtct acatgatcat ggtcaaatgt    3360
tggatgattg actctgaatg tcggccaaga ttccgggagt tggtgtctga attctcccgc    3420
atggccaggg accccagcg ctttgtggtc atccagaatg aggacttggg ccagccagt    3480 cccttggaca gcaccttcta ccgctcactg ctggaggacg atgacatggg ggacctggtg    3540
gatgctgagg agtatctggt accccagcag ggcttcttct gtccagaccc tgccccgggc    3600
```

```
gctgggggca tggtccacca caggcaccgc agctcatcta ccaggagtgg cggtggggac    3660
ctgacactag ggctggagcc ctctgaagag gaggccccca ggtctccact ggcaccctcc    3720 gaagggctg gctccgatgt atttgatggt gacctgggaa tgggggcagc caaggggctg    3780
caaagcctcc ccacacatga ccccagccct ctacagcgt acagtgagga ccccacagta    3840
cccctgccct ctgagactga tggctacgtt gccccctga cctgcagccc ccagcctgaa    3900
tatgtgaacc agccagatgt tcggcccag cccccttcgc cccagagggg ccctctgcct    3960
gctgcccgac ctgctggtgc cactctggaa aggcccaaga ctctctcccc agggaagaat    4020
ggggtcgtca agacgtttt tgcctttggg ggtgccgtgg agaacccga gtacttgaca    4080 ccccagggag gagctgcccc tcagccccac cctcctcctg ccttcagccc agccttcgac    4140
aacctctatt actgggacca ggacccacca gagcgggggg ctccacccag caccttcaaa    4200
gggacaccta cggcagagaa cccagagtac ctgggtctgg acgtgccagt gtgaaccaga    4260
aggccaagtc cgcagaagcc ctgatgtgtc ctcaggagc agggaaggcc tgacttctgc    4320
tggcatcaag aggtgggagg gccctccgac cacttccagg ggaacctgcc atgccaggaa    4380
cctgtcctaa ggaaccttcc ttcctgcttg agttcccaga tggctggaag gggtccagcc    4440
tcgttggaag aggaacagca ctggggagtc tttgtggatt ctgaggccct gcccaatgag    4500
actctagggt ccagtggatg ccacagccca gcttggccct ttccttccag atcctggta    4560 ctgaaagcct tagggaagct ggcctgagag gggaagcggc cctaagggag tgtctaagaa    4620
caaaagcgac ccattcagag actgtccctg aaacctagta ctgcccccca tgaggaagga    4680
acagcaatgg tgtcagtatc caggctttgt acagagtgct tttctgttta gttttacttt    4740 ttttgtttt gtttttttaa agatgaaata aagacccagg gggagaatgg gtgttgtatg    4800
gggaggcaag tgtgggggt ccttctccac acccactttg tccatttgca aatatatttt    4860
ggaaaacagc taaaaaaaaa aaaaaaaaa                                      4889
```

<210> SEQ ID NO 6
<211> LENGTH: 1225
<212> TYPE: PRT
<213> ORGANISM: Homo sapiens

<400> SEQUENCE: 6

```
Met Lys Leu Arg Leu Pro Ala Ser Pro Glu Thr His Leu Asp Met Leu
1               5                   10                  15

Arg His Leu Tyr Gln Gly Cys Gln Val Val Gln Gly Asn Leu Glu Leu
            20                  25                  30

Thr Tyr Leu Pro Thr Asn Ala Ser Leu Ser Phe Leu Gln Asp Ile Gln
        35                  40                  45

Glu Val Gln Gly Tyr Val Leu Ile Ala His Asn Gln Val Arg Gln Val
    50                  55                  60

Pro Leu Gln Arg Leu Arg Ile Val Arg Gly Thr Gln Leu Phe Glu Asp
65                  70                  75                  80

Asn Tyr Ala Leu Ala Val Leu Asp Asn Gly Asp Pro Leu Asn Asn Thr
                85                  90                  95

Thr Pro Val Thr Gly Ala Ser Pro Gly Gly Leu Arg Glu Leu Gln Leu
            100                 105                 110

Arg Ser Leu Thr Glu Ile Leu Lys Gly Gly Val Leu Ile Gln Arg Asn
        115                 120                 125

Pro Gln Leu Cys Tyr Gln Asp Thr Ile Leu Trp Lys Asp Ile Phe His
    130                 135                 140
```

```
Lys Asn Asn Gln Leu Ala Leu Thr Leu Ile Asp Thr Asn Arg Ser Arg
145                 150                 155                 160

Ala Cys His Pro Cys Ser Pro Met Cys Lys Gly Ser Arg Cys Trp Gly
            165                 170                 175

Glu Ser Ser Glu Asp Cys Gln Ser Leu Thr Arg Thr Val Cys Ala Gly
            180                 185                 190

Gly Cys Ala Arg Cys Lys Gly Pro Leu Pro Thr Asp Cys Cys His Glu
            195                 200                 205

Gln Cys Ala Ala Gly Cys Thr Gly Pro Lys His Ser Asp Cys Leu Ala
210                 215                 220

Cys Leu His Phe Asn His Ser Gly Ile Cys Glu Leu His Cys Pro Ala
225                 230                 235                 240

Leu Val Thr Tyr Asn Thr Asp Thr Phe Glu Ser Met Pro Asn Pro Glu
            245                 250                 255

Gly Arg Tyr Thr Phe Gly Ala Ser Cys Val Thr Ala Cys Pro Tyr Asn
            260                 265                 270

Tyr Leu Ser Thr Asp Val Gly Ser Cys Thr Leu Val Cys Pro Leu His
            275                 280                 285

Asn Gln Glu Val Thr Ala Glu Asp Gly Thr Gln Arg Cys Glu Lys Cys
290                 295                 300

Ser Lys Pro Cys Ala Arg Val Cys Tyr Gly Leu Gly Met Glu His Leu
305                 310                 315                 320

Arg Glu Val Arg Ala Val Thr Ser Ala Asn Ile Gln Glu Phe Ala Gly
            325                 330                 335

Cys Lys Lys Ile Phe Gly Ser Leu Ala Phe Leu Pro Glu Ser Phe Asp
            340                 345                 350

Gly Asp Pro Ala Ser Asn Thr Ala Pro Leu Gln Pro Glu Gln Leu Gln
            355                 360                 365

Val Phe Glu Thr Leu Glu Glu Ile Thr Gly Tyr Leu Tyr Ile Ser Ala
            370                 375                 380

Trp Pro Asp Ser Leu Pro Asp Leu Ser Val Phe Gln Asn Leu Gln Val
385                 390                 395                 400

Ile Arg Gly Arg Ile Leu His Asn Gly Ala Tyr Ser Leu Thr Leu Gln
            405                 410                 415

Gly Leu Gly Ile Ser Trp Leu Gly Leu Arg Ser Leu Arg Glu Leu Gly
            420                 425                 430

Ser Gly Leu Ala Leu Ile His His Asn Thr His Leu Cys Phe Val His
            435                 440                 445

Thr Val Pro Trp Asp Gln Leu Phe Arg Asn Pro His Gln Ala Leu Leu
            450                 455                 460

His Thr Ala Asn Arg Pro Glu Asp Glu Cys Val Gly Glu Gly Leu Ala
465                 470                 475                 480

Cys His Gln Leu Cys Ala Arg Gly His Cys Trp Gly Pro Gly Pro Thr
            485                 490                 495

Gln Cys Val Asn Cys Ser Gln Phe Leu Arg Gly Gln Glu Cys Val Glu
            500                 505                 510

Glu Cys Arg Val Leu Gln Gly Leu Pro Arg Glu Tyr Val Asn Ala Arg
            515                 520                 525

His Cys Leu Pro Cys His Pro Glu Cys Gln Pro Gln Asn Gly Ser Val
            530                 535                 540

Thr Cys Phe Gly Pro Glu Ala Asp Gln Cys Val Ala Cys Ala His Tyr
545                 550                 555                 560
```

-continued

```
Lys Asp Pro Pro Phe Cys Val Ala Arg Cys Pro Ser Gly Val Lys Pro
                565                 570                 575
Asp Leu Ser Tyr Met Pro Ile Trp Lys Phe Pro Asp Glu Glu Gly Ala
            580                 585                 590
Cys Gln Pro Cys Pro Ile Asn Cys Thr His Ser Cys Val Asp Leu Asp
        595                 600                 605
Asp Lys Gly Cys Pro Ala Glu Gln Arg Ala Ser Pro Leu Thr Ser Ile
    610                 615                 620
Ile Ser Ala Val Val Gly Ile Leu Leu Val Val Leu Gly Val Val
625                 630                 635                 640
Phe Gly Ile Leu Ile Lys Arg Arg Gln Gln Lys Ile Arg Lys Tyr Thr
                645                 650                 655
Met Arg Arg Leu Leu Gln Glu Thr Glu Leu Val Glu Pro Leu Thr Pro
            660                 665                 670
Ser Gly Ala Met Pro Asn Gln Ala Gln Met Arg Ile Leu Lys Glu Thr
        675                 680                 685
Glu Leu Arg Lys Val Lys Val Leu Gly Ser Gly Ala Phe Gly Thr Val
    690                 695                 700
Tyr Lys Gly Ile Trp Ile Pro Asp Gly Glu Asn Val Lys Ile Pro Val
705                 710                 715                 720
Ala Ile Lys Val Leu Arg Glu Asn Thr Ser Pro Lys Ala Asn Lys Glu
                725                 730                 735
Ile Leu Asp Glu Ala Tyr Val Met Ala Gly Val Gly Ser Pro Tyr Val
            740                 745                 750
Ser Arg Leu Leu Gly Ile Cys Leu Thr Ser Thr Val Gln Leu Val Thr
        755                 760                 765
Gln Leu Met Pro Tyr Gly Cys Leu Leu Asp His Val Arg Glu Asn Arg
    770                 775                 780
Gly Arg Leu Gly Ser Gln Asp Leu Leu Asn Trp Cys Met Gln Ile Ala
785                 790                 795                 800
Lys Gly Met Ser Tyr Leu Glu Asp Val Arg Leu Val His Arg Asp Leu
                805                 810                 815
Ala Ala Arg Asn Val Leu Val Lys Ser Pro Asn His Val Lys Ile Thr
            820                 825                 830
Asp Phe Gly Leu Ala Arg Leu Leu Asp Ile Asp Glu Thr Glu Tyr His
        835                 840                 845
Ala Asp Gly Gly Lys Val Pro Ile Lys Trp Met Ala Leu Glu Ser Ile
    850                 855                 860
Leu Arg Arg Arg Phe Thr His Gln Ser Asp Val Trp Ser Tyr Gly Val
865                 870                 875                 880
Thr Val Trp Glu Leu Met Thr Phe Gly Ala Lys Pro Tyr Asp Gly Ile
                885                 890                 895
Pro Ala Arg Glu Ile Pro Asp Leu Leu Glu Lys Gly Glu Arg Leu Pro
            900                 905                 910
Gln Pro Pro Ile Cys Thr Ile Asp Val Tyr Met Ile Met Val Lys Cys
        915                 920                 925
Trp Met Ile Asp Ser Glu Cys Arg Pro Arg Phe Arg Glu Leu Val Ser
    930                 935                 940
Glu Phe Ser Arg Met Ala Arg Asp Pro Gln Arg Phe Val Val Ile Gln
945                 950                 955                 960
Asn Glu Asp Leu Gly Pro Ala Ser Pro Leu Asp Ser Thr Phe Tyr Arg
                965                 970                 975
Ser Leu Leu Glu Asp Asp Asp Met Gly Asp Leu Val Asp Ala Glu Glu
```

Tyr Leu Val Pro Gln Gln Gly Phe Phe Cys Pro Asp Pro Ala Pro Gly
            980                 985                 990
                    995                 1000                1005

Ala Gly Gly Met Val His His Arg His Arg Ser Ser Ser Thr Arg
    1010                1015                1020

Ser Gly Gly Gly Asp Leu Thr Leu Gly Leu Glu Pro Ser Glu Glu
    1025                1030                1035

Glu Ala Pro Arg Ser Pro Leu Ala Pro Ser Glu Gly Ala Gly Ser
    1040                1045                1050

Asp Val Phe Asp Gly Asp Leu Gly Met Gly Ala Ala Lys Gly Leu
    1055                1060                1065

Gln Ser Leu Pro Thr His Asp Pro Ser Pro Leu Gln Arg Tyr Ser
    1070                1075                1080

Glu Asp Pro Thr Val Pro Leu Pro Ser Glu Thr Asp Gly Tyr Val
    1085                1090                1095

Ala Pro Leu Thr Cys Ser Pro Gln Pro Glu Tyr Val Asn Gln Pro
    1100                1105                1110

Asp Val Arg Pro Gln Pro Pro Ser Pro Arg Glu Gly Pro Leu Pro
    1115                1120                1125

Ala Ala Arg Pro Ala Gly Ala Thr Leu Glu Arg Pro Lys Thr Leu
    1130                1135                1140

Ser Pro Gly Lys Asn Gly Val Val Lys Asp Val Phe Ala Phe Gly
    1145                1150                1155

Gly Ala Val Glu Asn Pro Glu Tyr Leu Thr Pro Gln Gly Gly Ala
    1160                1165                1170

Ala Pro Gln Pro His Pro Pro Ala Phe Ser Pro Ala Phe Asp
    1175                1180                1185

Asn Leu Tyr Tyr Trp Asp Gln Asp Pro Pro Glu Arg Gly Ala Pro
    1190                1195                1200

Pro Ser Thr Phe Lys Gly Thr Pro Thr Ala Glu Asn Pro Glu Tyr
    1205                1210                1215

Leu Gly Leu Asp Val Pro Val
    1220                1225

<210> SEQ ID NO 7
<211> LENGTH: 1259
<212> TYPE: PRT
<213> ORGANISM: Artificial Sequence
<220> FEATURE:
<223> OTHER INFORMATION: Synthetic construct

<400> SEQUENCE: 7

Met Glu Leu Ala Ala Leu Cys Arg Trp Gly Leu Leu Ala Leu Leu
1               5                   10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr

```
            100                 105                 110
Ala Leu Ala Val Leu Asp Asn Gly Asp Pro Leu Asn Asn Thr Thr Pro
            115                 120             125
Val Thr Gly Ala Ser Pro Gly Gly Leu Arg Glu Leu Gln Leu Arg Ser
            130                 135         140
Leu Thr Glu Ile Leu Lys Gly Gly Val Leu Ile Gln Arg Asn Pro Gln
145                 150                 155                 160
Leu Cys Tyr Gln Asp Thr Ile Leu Trp Lys Asp Ile Phe His Lys Asn
                165                 170                 175
Asn Gln Leu Ala Leu Thr Leu Ile Asp Thr Asn Arg Ser Arg Ala Cys
            180                 185                 190
His Pro Cys Ser Pro Met Cys Lys Gly Ser Arg Cys Trp Gly Glu Ser
        195                 200                 205
Ser Glu Asp Cys Gln Ser Leu Thr Arg Thr Val Cys Ala Gly Gly Cys
        210                 215                 220
Ala Arg Cys Lys Gly Pro Leu Pro Thr Asp Cys Cys His Glu Gln Cys
225                 230                 235                 240
Ala Ala Gly Cys Thr Gly Pro Lys His Ser Asp Cys Leu Ala Cys Leu
                245                 250                 255
His Phe Asn His Ser Gly Ile Cys Glu Leu His Cys Pro Ala Leu Val
                260                 265                 270
Thr Tyr Asn Thr Asp Thr Phe Glu Ser Met Pro Asn Pro Glu Gly Arg
            275                 280                 285
Tyr Thr Phe Gly Ala Ser Cys Val Thr Ala Cys Pro Tyr Asn Tyr Leu
        290                 295                 300
Ser Thr Asp Val Gly Ser Cys Thr Leu Val Cys Pro Leu His Asn Gln
305                 310                 315                 320
Glu Val Thr Ala Glu Asp Gly Thr Gln Arg Cys Glu Lys Cys Ser Lys
                325                 330                 335
Pro Cys Ala Arg Val Cys Tyr Gly Leu Gly Met Glu His Leu Arg Glu
                340                 345                 350
Val Arg Ala Val Thr Ser Ala Asn Ile Gln Glu Phe Ala Gly Cys Lys
            355                 360                 365
Lys Ile Phe Gly Ser Leu Ala Phe Leu Pro Glu Ser Phe Asp Gly Asp
        370                 375                 380
Pro Ala Ser Asn Thr Ala Pro Leu Gln Pro Glu Gln Leu Gln Val Phe
385                 390                 395                 400
Glu Thr Leu Glu Glu Ile Thr Gly Tyr Leu Tyr Ile Ser Ala Trp Pro
                405                 410                 415
Asp Ser Leu Pro Asp Leu Ser Val Phe Gln Asn Leu Gln Val Ile Arg
                420                 425                 430
Gly Arg Ile Leu His Asn Gly Ala Tyr Ser Leu Thr Leu Gln Gly Leu
            435                 440                 445
Gly Ile Ser Trp Leu Gly Leu Arg Ser Leu Arg Glu Leu Gly Ser Gly
        450                 455                 460
Leu Ala Leu Ile His His Asn Thr His Leu Cys Phe Val His Thr Val
465                 470                 475                 480
Pro Trp Asp Gln Leu Phe Arg Asn Pro His Gln Ala Leu Leu His Thr
                485                 490                 495
Ala Asn Arg Pro Glu Asp Glu Cys Val Gly Glu Gly Leu Ala Cys His
            500                 505                 510
Gln Leu Cys Ala Arg Gly His Cys Trp Gly Pro Gly Pro Thr Gln Cys
        515                 520                 525
```

```
Val Asn Cys Ser Gln Phe Leu Arg Gly Gln Glu Cys Val Glu Glu Cys
530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Leu Gly Val Val Phe Gly
                660                 665                 670

Ile Leu Ile Lys Arg Arg Gln Gln Lys Ile Arg Lys Tyr Thr Met Arg
            675                 680                 685

Arg Leu Leu Gln Glu Thr Glu Leu Val Glu Pro Leu Thr Pro Ser Gly
        690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Tyr Val Met Ala Gly Val Gly Ser Pro
770                 775                 780

Tyr Val Ser Arg Leu Leu Gly Ile Cys Leu Thr Ser Thr Val Gln Leu
785                 790                 795                 800

Val Thr Gln Leu Met Pro Tyr Gly Cys Leu Leu Asp His Val Arg Glu
                805                 810                 815

Asn Arg Gly Arg Leu Gly Ser Gln Asp Leu Leu Asn Trp Cys Met Gln
            820                 825                 830

Ile Ala Lys Gly Met Ser Tyr Leu Glu Asp Val Arg Leu Val His Arg
        835                 840                 845

Asp Leu Ala Ala Arg Asn Val Leu Val Lys Ser Pro Asn His Val Lys
850                 855                 860

Ile Thr Asp Phe Gly Leu Ala Arg Leu Leu Asp Ile Asp Glu Thr Glu
865                 870                 875                 880

Tyr His Ala Asp Gly Gly Lys Val Pro Ile Lys Trp Met Ala Leu Glu
                885                 890                 895

Ser Ile Leu Arg Arg Arg Phe Thr His Gln Ser Asp Val Trp Ser Tyr
            900                 905                 910
```

```
Gly Val Thr Val Trp Glu Leu Met Thr Phe Gly Ala Lys Pro Tyr Asp
        915                 920                 925

Gly Ile Pro Ala Arg Glu Ile Pro Asp Leu Leu Glu Lys Gly Glu Arg
        930                 935             940

Leu Pro Gln Pro Pro Ile Cys Thr Ile Asp Val Tyr Met Ile Met Val
945                 950                 955                 960

Lys Cys Trp Met Ile Asp Ser Glu Cys Arg Pro Arg Phe Arg Glu Leu
                965                 970                 975

Val Ser Glu Phe Ser Arg Met Ala Arg Asp Pro Gln Arg Phe Val Val
            980                 985                 990

Ile Gln Asn Glu Asp Leu Gly Pro  Ala Ser Pro Leu Asp  Ser Thr Phe
        995                 1000                1005

Tyr Arg  Ser Leu Leu Glu Asp  Asp Asp Met Gly Asp  Leu Val Asp
    1010                 1015                1020

Ala Glu  Glu Tyr Leu Val Pro  Gln Gln Gly Phe Phe  Cys Pro Asp
    1025                1030                1035

Pro Ala  Pro Gly Ala Gly Gly  Met Val His His Arg  His Arg Ser
    1040                1045                1050

Ser Ser  Thr Arg Ser Gly Gly  Gly Asp Leu Thr Leu  Gly Leu Glu
    1055                1060                1065

Pro Ser  Glu Glu Glu Ala Pro  Arg Ser Pro Leu Ala  Pro Ser Glu
    1070                1075                1080

Gly Ala  Gly Ser Asp Val Phe  Asp Gly Asp Leu Gly  Met Gly Ala
    1085                1090                1095

Ala Lys  Gly Leu Gln Ser Leu  Pro Thr His Asp Pro  Ser Pro Leu
    1100                1105                1110

Gln Arg  Tyr Ser Glu Asp Pro  Thr Val Pro Leu Pro  Ser Glu Thr
    1115                1120                1125

Asp Gly  Tyr Val Ala Pro Leu  Thr Cys Ser Pro Gln  Pro Glu Tyr
    1130                1135                1140

Val Asn  Gln Pro Asp Val Arg  Pro Gln Pro Pro Ser  Pro Arg Glu
    1145                1150                1155

Gly Pro  Leu Pro Ala Ala Arg  Pro Ala Gly Ala Thr  Leu Glu Arg
    1160                1165                1170

Pro Lys  Thr Leu Ser Pro Gly  Lys Asn Gly Val Val  Lys Asp Val
    1175                1180                1185

Phe Ala  Phe Gly Gly Ala Val  Glu Asn Pro Glu Tyr  Leu Thr Pro
    1190                1195                1200

Gln Gly  Gly Ala Ala Pro Gln  Pro His Pro Pro Ala  Phe Ser
    1205                1210                1215

Pro Ala  Phe Asp Asn Leu Tyr  Tyr Trp Asp Gln Asp  Pro Pro Glu
    1220                1225                1230

Arg Gly  Ala Pro Pro Ser Thr  Phe Lys Gly Thr Pro  Thr Ala Glu
    1235                1240                1245

Asn Pro  Glu Tyr Leu Gly Leu  Asp Val Pro Val
    1250                1255
```